US009441238B2

(12) United States Patent
Champagne et al.

(10) Patent No.: US 9,441,238 B2
(45) Date of Patent: Sep. 13, 2016

(54) COMPOSITIONS AND METHODS FOR MODULATING THE SENSITIVITY OF CELLS TO AHAS INHIBITORS

(71) Applicant: SYNTHETIC GENOMICS, INC., La Jolla, CA (US)

(72) Inventors: Michele M. Champagne, San Diego, CA (US); Jun Urano, Irvine, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 315 days.

(21) Appl. No.: 13/871,737

(22) Filed: Apr. 26, 2013

(65) Prior Publication Data

US 2013/0288377 A1 Oct. 31, 2013

Related U.S. Application Data

(60) Provisional application No. 61/639,727, filed on Apr. 27, 2012.

(51) Int. Cl.
 C12N 15/82 (2006.01)
 C12N 9/10 (2006.01)
 C12N 15/79 (2006.01)

(52) U.S. Cl.
 CPC ......... *C12N 15/8274* (2013.01); *C12N 9/1022* (2013.01); *C12N 15/79* (2013.01); *C12N 15/8214* (2013.01); *C12N 15/8278* (2013.01); *C12Y 202/01006* (2013.01)

(58) Field of Classification Search
 CPC .................................. C12N 15/82; C12N 9/10
 See application file for complete search history.

(56) References Cited

U.S. PATENT DOCUMENTS

| 6,025,541 A | 2/2000 | Dietrich et al. | |
|---|---|---|---|
| 7,083,967 B1 * | 8/2006 | Kakefuda et al. | ... C12N 9/0004 435/232 |
| 2007/0118916 A1 | 5/2007 | Puzio et al. | |
| 2007/0243543 A1 | 10/2007 | Song et al. | |
| 2011/0053777 A1 | 3/2011 | Oard et al. | |

FOREIGN PATENT DOCUMENTS

| WO | WO 2006/069610 A2 | 7/2006 | |
|---|---|---|---|
| WO | WO 2007/136428 A2 | 11/2007 | |
| WO | WO2010078156 | * 7/2010 | ............. A01H 13/00 |

OTHER PUBLICATIONS

Evertsz, E. M., et al. "Research Report Hybridization Cross-Reactivity within Homologous Gene Families on Glass cDNA Microarrays." Biotechniques 31.5 (2001): 1182-1192.*

(Continued)

*Primary Examiner* — Russell Kallis
*Assistant Examiner* — Weihua Fan
(74) *Attorney, Agent, or Firm* — DLA Piper LLP (US)

(57) ABSTRACT

Methods and materials useful for modulating the sensitivity of cells to an inhibitor of acetohydroxyacid synthase (AHAS) are disclosed. For example, nucleic acid molecules encoding AHAS large subunits are disclosed as well as methods for using such nucleic acid molecules to transform microbial cells and plant cells, and to confer modulated sensitivity to AHAS-inhibiting compounds onto such cells. Further provided are materials and methods useful for modulating growth, development, activity, and characteristics of host cells and organisms.

23 Claims, 4 Drawing Sheets

(56) References Cited

OTHER PUBLICATIONS

Duggleby, Ronald G., Jennifer A. McCourt, and Luke W. Guddat. "Structure and mechanism of inhibition of plant acetohydroxyacid synthase." Plant Physiology and Biochemistry 46.3 (2008): 309-324.*

Saurabh, Satyajit, Ambarish S. Vidyarthi, and Dinesh Prasad. "RNA interference: concept to reality in crop improvement." Planta 239.3 (2014): 543-564.*

Pan et al.: "*Nuclear Monoploidy and Asexual Propagation of Nannochloropsis Oceanica (Eustigmatophyceae) As Revealed by Its Genome Sequence*" J. Phycol. 47, pp. 1425-1432 (2011).

International Search Report Regarding PCT/US2013/038517.

Chipman, David et al.: "*Biosynthesis of 2-aceto-2-hydroxy acids: acetolactate synthases and acetohydroxyacid synthases*"; Biochimica Et Biophysica Acta, vol. 1385, No. 2, Jun. 16, 1998, pp. 401-419.

Lapidot, Miri et al.: "*Stable chloroplast transformation of the unicellular red alga Porphyridium species*"; Plant Physiology, vol. 129, No. 1, May 1, 2002, pp. 7-12.

Mc Court, Jennifer A. et al.: "*Herbicide-binding sites revealed in the structure of plant acetohydroxyacid synthase*"; PNAS, vol. 103, No. 3, Jan. 17, 2006, pp. 569-573.

XP002744698: "*RecName: Full=Acetolactate synthase ECO:0000256:RuleBase:RU003591); EC=2.2.1.6 {ECO:00002561RuleBase:RU003591};*" Database UniProt [Online], Jul. 1, 2008, retrieved from EBI accession No. UNIPROT:B2XT40, Database accession No. B2XT40.

XP002744699: "*RecName: Full=Acetolactate synthase {ECO:00002561RuleBase:RU003591}; EC=2.2.1.6 {ECO:0000256:RuleBase:RU003591.1}*", Database UniProt [Online], Sep. 1, 2009, retrieved from EBI accession No. UNIPROT:C6KIX7, Database accession No. C6KIX7.

XP002744700: "*RecName: Full=Acetolactate synthaseECO:0000256:RuleBase:RU003591); EC=2.2.1.6 {ECO:0000256:RuleBase:RU0035911};*"Database UniProt [Online], Sep. 1, 2009, retrieved from EBI accession No. UNIPROT:C6KIN9, Database accession No. C6KIN9.

Extended European Search Report issued Sep. 30, 2015, regarding EP 13782158.3.

* cited by examiner

SEQUENCE LISTING

<160> NUMBER OF SEQ ID NOS: 34

<210> SEQ ID NO 1

```
<211> LENGTH: 592
<212> TYPE: PRT
<213> ORGANISM: Nannochloropsis gaditana
<220> FEATURE:
<221> NAME/KEY: misc_feature
<223> OTHER INFORMATION: SGI peptide ID Ng12345
<220> FEATURE:
<221> NAME/KEY: misc_feature
<223> OTHER INFORMATION: acetohydroxyacid synthase
<220> FEATURE:
<221> NAME/KEY: misc_feature
<222> LOCATION: (33)..(36)
<223> OTHER INFORMATION: substantially conserved sub-sequence A
<220> FEATURE:
<221> NAME/KEY: misc_feature
<222> LOCATION: (111)..(114)
<223> OTHER INFORMATION: substantially conserved sub-sequence B
<220> FEATURE:
<221> NAME/KEY: misc_feature
<222> LOCATION: (118)..(125)
<223> OTHER INFORMATION: substantially conserved sub-sequence C
<220> FEATURE:
<221> NAME/KEY: misc_feature
<222> LOCATION: (172)..(174)
<223> OTHER INFORMATION: substantially conserved sub-sequence D
<220> FEATURE:
<221> NAME/KEY: misc_feature
<222> LOCATION: (266)..(271)
<223> OTHER INFORMATION: substantially conserved sub-sequence G
<220> FEATURE:
<221> NAME/KEY: misc_feature
<222> LOCATION: (294)..(298)
<223> OTHER INFORMATION: substantially conserved sub-sequence E
<220> FEATURE:
<221> NAME/KEY: misc_feature
<222> LOCATION: (489)..(498)
<223> OTHER INFORMATION: substantially conserved sub-sequence F

<400> SEQUENCE: 1

Val Lys Ile Lys Lys Gln Thr Arg Arg Ile His Thr Gly Ala Phe Ala
1               5                   10                  15

Leu Ile Asp Ser Leu Val Arg Asn Gly Gly Lys Thr Ile Phe Gly Tyr
            20                  25                  30

Pro Gly Gly Ala Ile Leu Pro Ile Tyr Asp Glu Leu Tyr Leu Trp Glu
        35                  40                  45

Glu Gly Leu Ile Glu His Ile Leu Val Arg His Glu Gln Gly Ala
50                  55                  60

Ala His Ala Ala Asp Ala Tyr Ala Arg Ala Ser Gly Lys Val Gly Ile
65                  70                  75                  80

Cys Phe Ala Thr Ser Gly Pro Gly Ala Thr Asn Leu Val Thr Gly Ile
                85                  90                  95

Ala Thr Ala Asp Met Asp Ser Ile Pro Met Ile Leu Ile Thr Gly Gln
            100                 105                 110

Val Gly Arg Ala Phe Ile Gly Thr Asp Ala Phe Gln Glu Val Asp Ile
        115                 120                 125

Tyr Asn Ile Thr Lys Pro Ile Val Lys Ala Ser Tyr Val Val Asn Asp
    130                 135                 140

Ala Ser Met Ile Pro Glu Ile Val Ser Glu Ala Phe Tyr Leu Ala Lys
145                 150                 155                 160

Asn Gly Arg Pro Gly Pro Val Leu Ile Asp Ile Pro Lys Asp Val Gly
                165                 170                 175

Leu Glu Glu Ile Val Gln Tyr Val Pro Ile Tyr Gln Gln Glu Thr Thr
            180                 185                 190

Lys Asn Lys Arg Tyr Glu Phe Leu Phe Gln Thr Pro Phe Asp Gln Ile
        195                 200                 205
```

```
Arg Ser Ala Leu Thr Leu Ile Lys Gln Ser Ser Gln Pro Leu Phe Tyr
210                 215                 220

Val Gly Gly Ala Val Leu Ala Glu Ala Arg Gln Glu Leu Leu Ala
225                 230                 235                 240

Leu Ala Glu Thr Phe Glu Ile Pro Val Thr Thr Leu Met Gly Lys
            245                 250                 255

Gly Ala Phe His Glu Asn His Arg Leu Tyr Leu Gly Met Leu Gly Met
                260                 265                 270

His Gly Thr Gly Tyr Ala Asn Phe Ala Val Ser Glu Cys Asp Leu Leu
            275                 280                 285

Ile Ala Ile Gly Ala Arg Phe Asp Asp Arg Val Thr Gly Lys Leu Glu
290                 295                 300

Asp Phe Ala Ser Gln Ala Gln Ile Leu Gln Ile Asp Ile Asp Pro Asn
305                 310                 315                 320

Glu Ile Gly Lys Asn Lys Ile Pro His Leu Ala Ile Ile Gly Asp Ile
                325                 330                 335

Lys Lys Val Leu Gln Gln Leu Leu Lys His Ser Asn Ser Val Thr Pro
            340                 345                 350

Leu Tyr Asp Ala Thr Gln Thr Arg Phe Trp Arg Glu Arg Ile Leu Lys
            355                 360                 365

Trp Lys Glu Arg Tyr Pro Leu Ile Ile Pro Asn Val Asp Ser Gly Leu
370                 375                 380

Ser Pro Gln Gln Ile Val Asn Arg Leu Ala Glu Leu Leu Pro Asn Ala
385                 390                 395                 400

Tyr Phe Thr Thr Asp Val Gly Gln His Gln Met Trp Ala Ala Gln Phe
                405                 410                 415

Leu Lys Cys Asn Leu Arg Lys Trp Met Ser Ser Ala Gly Leu Gly Thr
            420                 425                 430

Met Gly Tyr Gly Leu Pro Ala Ala Ile Gly Val Gln Leu Ala Phe Pro
            435                 440                 445

Asn Ser Asn Val Ile Cys Ile Ser Gly Asp Ala Ser Phe Gln Met Asn
            450                 455                 460

Leu Gln Glu Leu Gly Thr Ile Ala Gln Tyr Asn Leu Pro Ile Lys Ile
465                 470                 475                 480

Phe Ile Leu Asn Asn Arg Trp Gln Gly Met Val Arg Gln Trp Gln Gln
                485                 490                 495

Ser Phe Tyr Asp Glu Arg Tyr Ser His Ser Ser Met Lys Asp Gly Met
            500                 505                 510

Pro Asp Phe Val Lys Leu Ala Glu Ser Tyr Gly Ile Lys Gly Cys Arg
            515                 520                 525

Ile Lys Thr Val Glu Glu Phe Leu Lys Ile Glu Asn Asp Ile Val Leu
530                 535                 540

Ala Asn Gln Pro Leu Leu Ile Asp Phe Asp Val Thr Glu Thr Glu Asn
545                 550                 555                 560

Cys Tyr Pro Met Val Ala Pro Gly Lys Ser Ser Gln Met Ile Gly
                565                 570                 575

Leu Ser Asn Glu Ser Ser Leu Gln Thr Thr Thr Lys Lys Ile Phe Val
            580                 585                 590

<210> SEQ ID NO 2
<211> LENGTH: 2823
<212> TYPE: DNA
<213> ORGANISM: Nannochloropsis gaditana
<220> FEATURE:
<221> NAME/KEY: misc_feature
```

<223> OTHER INFORMATION: SGI Gene ID Ng12345
<220> FEATURE:
<221> NAME/KEY: misc_feature
<223> OTHER INFORMATION: acetohydroxyacid synthase
<220> FEATURE:
<221> NAME/KEY: misc_feature
<223> OTHER INFORMATION: encodes the peptide sequence at SEQ ID NO 1
     (503..2281)

<400> SEQUENCE: 2

| | | | | | |
|---|---|---|---|---|---|
| agagtggctc | ccaacatatc | cttttgcaag | ccctaagatt | ttttttctag | attttctagc | 60 |
| tatatttcct | cttttaacac | gtatcatttt | attttatctc | attttaattg | ttaaagaact | 120 |
| tttttactgt | taatttttca | gtattcccta | cagtaatagt | agaacaaagc | cttctttttc | 180 |
| tagaagaaga | ttttttttgt | aataaatggc | ctttaaaggc | tttttttcta | atgaaatttt | 240 |
| tatttgccgt | ttgtttatat | cttttaccg | ctgattttct | tgttttagat | ttattcataa | 300 |
| aataactctt | cgatttgttc | gtaaaatagt | ataaaatatt | gtacaattaa | aagagataaa | 360 |
| aaacaagcaa | ttcttaacta | aacgtattaa | gtttgattaa | cttcttaaat | gttttaattt | 420 |
| ttaataaaaa | taaattaatc | aaagttttgt | atttttttaag | cagatcaaaa | tttaattta | 480 |
| aaaaattgaa | aaaggtgaat | aagtgaaaat | caagaaacaa | actcgaagaa | tacatacagg | 540 |
| agcatttgca | ttaattgata | gtttagtgcg | taatggtgga | aaaacaattt | ttggttaccc | 600 |
| gggtggggca | attctaccta | tttatgatga | attataccct | tgggaagaag | aaggtttaat | 660 |
| tgaacatatt | ttagttagac | acgaacaagg | tgcagcccat | gcagcggatg | cttatgctcg | 720 |
| tgcaagcgga | aagtaggaa | tttgttttgc | aacttcaggc | ccgggagcaa | caaatttagt | 780 |
| tactggaatt | gcaaccgctg | atatggattc | tataccaatg | attttaatta | ctggtcaggt | 840 |
| aggtagagca | tttattggaa | cagatgcttt | tcaagaagtt | gatatctata | acataactaa | 900 |
| accaattgta | aaggcttcgt | atgttgtaaa | tgatgcaagt | atgattccag | aaatcgtttc | 960 |
| tgaagccttt | tacttggcaa | aaaatggtcg | tcctggtcca | gttttaattg | atattccaaa | 1020 |
| agatgtaggg | ttagaagaaa | tagttcagta | tgtacctata | tatcaacagg | aaactactaa | 1080 |
| aaataaacga | tatgaatttt | tatttcaaac | tcccttgat | caaattcgtt | ccgctttaac | 1140 |
| attaataaaa | caatcatcac | aaccgttgtt | ttatgtcggt | ggaggagctg | ttttagctga | 1200 |
| agctcgccaa | gaactttag | ctttagcaga | aacatttgaa | attcctgtta | caacaacatt | 1260 |
| aatgggaaaa | ggagctttc | atgaaaacca | tcgtttatat | ttaggaatgc | taggtatgca | 1320 |
| tggtacaggt | tatgctaatt | ttgcagtaag | tgagtgtgat | ttacttatag | caataggtgc | 1380 |
| aagatttgat | gatcgggtta | ctggtaaact | tgaagatttc | gcctctcaag | cacaaattct | 1440 |
| ccaaattgat | attgatccaa | atgaaattgg | aaaaaataag | atacctcatt | tagctattat | 1500 |
| tggagatata | aaaaaagttt | tacaacaatt | gttaaaacat | tcaaattcag | taactccttt | 1560 |
| atatgacgca | acacaaacca | gattttggcg | agaaagaatc | ttaaaatgga | agagcgtta | 1620 |
| tccattaatt | attccaaacg | tagatagcgg | tttatcacct | cagcaaattg | taatcgtttt | 1680 |
| agctgaactt | cttccaaatg | cctattttac | tacagacgtt | ggtcagcatc | aaatgtgggc | 1740 |
| agcccaattt | ctaaaatgta | atcttagaaa | atggatgtca | agtgctgggt | taggcactat | 1800 |
| gggttatggt | ttaccagcag | caataggagt | tcaattagca | tttcccaatt | caaatgtaat | 1860 |
| ttgtattagt | ggagatgcta | gttttcaaat | gaatcttcaa | gagttaggaa | caatagcaca | 1920 |
| gtataatcta | cccattaaaa | tctttatttt | aaataatcgt | tggcaaggta | tggtacgaca | 1980 |
| atggcaacag | tctttttatg | atgaaagata | ttcacattca | tctatgaaag | atggtatgcc | 2040 |

```
agattttgtt aaacttgctg agtcttatgg aattaaaggg tgccgtataa aaacagttga    2100
agaatttcta aaaatagaaa atgatattgt tttagcaaat caaccattat tgattgactt    2160
tgatgtaacc gaaactgaaa attgttatcc aatggttgca ccaggtaaaa gtaattcaca    2220
aatgatcgga ttaagtaatg aatcatctct gcagactact actaaaaaaa tatttgttta    2280
aataggccga gttggatttg aaccaacgta ggctgagcca gcggatttac agtccgcccc    2340
ctttaaccac tcgggcatcg accctacttt tattaaatta tgcactaaac caatatattt    2400
ataaatctaa tgctttaagc attagattta taaatatgtc gaataaagag ctataccaat    2460
tgctgctaca atgctaccaa ttaaaccacc actaaagaag ccttctgaaa attttttgcca   2520 gcctaaaata gtatctagtt cgcttgttcc tttaatttga ggtaattctt gtgttttttc    2580
tgaacctacc atttgtcgta caagtttaac aataagagcg ttatcataaa cgtcataagt    2640
aacttggccg taaattgata atcctacagt taaaattaat aataacgtta tagcagcaag    2700
aagacctgca gctaacgaag taagtgaaaa ttctgcggag cgcaatggac cataagtgta    2760
aaacggtcct ataagaaagt aaccatgtgt aaaaccaatt tcagctcctc ttgaaagtgg    2820
tgt                                                                  2823
```

```
<210> SEQ ID NO 3
<211> LENGTH: 592
<212> TYPE: PRT
<213> ORGANISM: Nannochloropsis salina
<220> FEATURE:
<221> NAME/KEY: misc_feature
<223> OTHER INFORMATION: SGI peptide ID Ns12345
<220> FEATURE:
<221> NAME/KEY: misc_feature
<223> OTHER INFORMATION: acetohydroxyacid synthase
<220> FEATURE:
<221> NAME/KEY: misc_feature
<222> LOCATION: (33)..(36)
<223> OTHER INFORMATION: substantially conserved sub-sequence A
<220> FEATURE:
<221> NAME/KEY: misc_feature
<222> LOCATION: (111)..(114)
<223> OTHER INFORMATION: substantially conserved sub-sequence B
<220> FEATURE:
<221> NAME/KEY: misc_feature
<222> LOCATION: (118)..(125)
<223> OTHER INFORMATION: substantially conserved sub-sequence C
<220> FEATURE:
<221> NAME/KEY: misc_feature
<222> LOCATION: (172)..(174)
<223> OTHER INFORMATION: substantially conserved sub-sequence D
<220> FEATURE:
<221> NAME/KEY: misc_feature
<222> LOCATION: (266)..(271)
<223> OTHER INFORMATION: substantially conserved sub-sequence G
<220> FEATURE:
<221> NAME/KEY: misc_feature
<222> LOCATION: (294)..(298)
<223> OTHER INFORMATION: substantially conserved sub-sequence E
<220> FEATURE:
<221> NAME/KEY: misc_feature
<222> LOCATION: (489)..(498)
<223> OTHER INFORMATION: substantially conserved sub-sequence F

<400> SEQUENCE: 3

Val Lys Ile Lys Lys Gln Thr Arg Arg Ile His Thr Gly Ala Phe Ala
1               5                   10                  15

Leu Ile Asp Ser Leu Val Arg Asn Gly Gly Lys Thr Ile Phe Gly Tyr
                20                  25                  30

Pro Gly Gly Ala Ile Leu Pro Ile Tyr Asp Glu Leu Tyr Leu Trp Glu
            35                  40                  45
```

-continued

Glu Glu Gly Leu Ile Glu His Ile Leu Val Arg His Glu Gln Gly Ala
    50              55                  60

Ala His Ala Ala Asp Ala Tyr Ala Arg Ala Ser Gly Lys Val Gly Ile
65              70                  75                  80

Cys Phe Ala Thr Ser Gly Pro Ala Thr Asn Leu Val Thr Gly Ile
                85                  90                  95

Ala Thr Ala Asp Met Asp Ser Ile Pro Met Ile Leu Ile Thr Gly Gln
            100                 105                 110

Val Gly Arg Ala Phe Ile Gly Thr Asp Ala Phe Gln Glu Val Asp Ile
        115                 120                 125

Tyr Asn Ile Thr Lys Pro Ile Val Lys Ala Ser Tyr Val Val Asn Asp
    130                 135                 140

Ala Ser Met Ile Pro Glu Ile Val Ser Glu Ala Phe Tyr Leu Ala Lys
145                 150                 155                 160

Asn Gly Arg Pro Gly Pro Val Leu Ile Asp Ile Pro Lys Asp Val Gly
                165                 170                 175

Leu Glu Glu Ile Thr Gln Tyr Val Pro Ile Tyr Gln Gln Glu Thr Thr
            180                 185                 190

Lys Asn Lys Arg Tyr Glu Phe Leu Phe Gln Thr Pro Phe Asp Gln Ile
        195                 200                 205

Arg Ser Ala Leu Thr Leu Ile Lys Gln Ser Ser Gln Pro Leu Phe Tyr
    210                 215                 220

Val Gly Gly Gly Ala Val Leu Ala Glu Ala Arg Gln Glu Leu Leu Ala
225                 230                 235                 240

Leu Ala Glu Thr Phe Glu Ile Pro Val Thr Thr Thr Leu Met Gly Lys
                245                 250                 255

Gly Ala Phe His Glu Asn His Arg Leu Tyr Leu Gly Met Leu Gly Met
            260                 265                 270

His Gly Thr Gly Tyr Ala Asn Phe Ala Val Ser Glu Cys Asp Leu Leu
        275                 280                 285

Ile Ala Ile Gly Ala Arg Phe Asp Asp Arg Val Thr Gly Lys Leu Glu
    290                 295                 300

Asp Phe Ala Ser Gln Ala Gln Ile Leu Gln Ile Asp Ile Asp Pro Asn
305                 310                 315                 320

Glu Ile Gly Lys Asn Lys Ile Pro His Leu Ala Ile Ile Gly Asp Ile
                325                 330                 335

Lys Lys Val Leu Gln Gln Leu Leu Lys His Ser Asn Ser Val Thr Pro
            340                 345                 350

Leu Tyr Asp Ala Thr Gln Thr Arg Phe Trp Arg Glu Arg Ile Leu Lys
        355                 360                 365

Trp Lys Glu Arg Tyr Pro Leu Ile Ile Pro Asn Val Asp Thr Gly Leu
    370                 375                 380

Ser Pro Gln Gln Ile Val Asn Arg Leu Ala Glu Leu Leu Pro Asn Ala
385                 390                 395                 400

Tyr Phe Thr Thr Asp Val Gly Gln His Gln Met Trp Ala Ala Gln Phe
                405                 410                 415

Leu Lys Cys Asn Leu Arg Lys Trp Met Ser Ser Ala Gly Leu Gly Thr
            420                 425                 430

Met Gly Tyr Gly Leu Pro Ala Ala Ile Gly Val Gln Leu Ala Phe Pro
        435                 440                 445

Asn Ser Asn Val Val Cys Ile Ser Gly Asp Ala Ser Phe Gln Met Asn
450                 455                 460

Leu Gln Glu Leu Gly Thr Ile Ala Gln Tyr Asn Leu Pro Ile Lys Ile

```
            465                 470                 475                 480
      Phe Ile Leu Asn Asn Arg Trp Gln Gly Met Val Arg Gln Trp Gln Gln
                        485                 490                 495
      Ser Phe Tyr Asp Glu Arg Tyr Ser His Ser Ser Met Lys Asp Gly Met
                        500                 505                 510
      Pro Asp Phe Val Lys Leu Ala Glu Ser Tyr Gly Ile Lys Gly Cys Arg
                        515                 520                 525
      Ile Lys Thr Val Glu Glu Phe Gln Lys Ile Glu Asn Asp Ile Val Leu
                        530                 535                 540
      Ala Asn Gln Pro Leu Leu Ile Asp Phe Asp Val Thr Glu Thr Glu Asn
      545                 550                 555                 560
      Cys Tyr Pro Met Val Ala Pro Gly Lys Ser Asn Ser Gln Met Ile Gly
                        565                 570                 575
      Leu Ser Asn Glu Ser Ser Leu Gln Thr Thr Thr Lys Lys Ile Phe Ile
                        580                 585                 590

<210> SEQ ID NO 4
<211> LENGTH: 2780
<212> TYPE: DNA
<213> ORGANISM: Nannochloropsis salina
<220> FEATURE:
<221> NAME/KEY: misc_feature
<223> OTHER INFORMATION: SGI Gene ID Ns12345
<220> FEATURE:
<221> NAME/KEY: misc_feature
<223> OTHER INFORMATION: acetohydroxyacid synthase
<220> FEATURE:
<221> NAME/KEY: misc_feature
<223> OTHER INFORMATION: encodes the peptide sequence at SEQ ID NO 3

<400> SEQUENCE: 4
cttttgcaag ccctaagact ttttttctag attttctagc tatatttcct cttctaacac     60
gtatcatttt actttatctc attttaattg ttaaagaact tttttactgt taattttttca   120
gtatttccta cagtaatagt agaacaaagt cttcttttc tagaagaaga ttttttttgt      180
aataaatggc ctttaaaggc ttttttttcta atgaaatttt tatttgctgt ttgtttatat    240
cttttttaccg ccgatttttct tgttttagat ttattcataa aataactctt cgatttgttc    300
gtaaaatagt ataaaatact atacaattaa aagagataaa aaacaagcaa ttcttgacta    360
aacgtattaa gttgattaa cttcttaaat gttttaattt ttaataaaaa taaattaatc     420
aaagtttttgt atttttttaag cagatcaaaa tttaatttta aaaaattgaa aaaggtgaat    480
aagtgaaaat caagaaacaa actcgaagaa tacatacagg agcattcgca ttaattgata    540
gtttagtgcg taatggtgga aaaacaattt ttggttaccc gggtggggca attctaccta    600
tttatgatga attataccct tgggaagaag aaggtttaat tgaacatatt ttagttagac    660
acgaacaagg tgcagcccat gcagcggatg cttatgctcg tgcaagcgga aaggtaggga    720
tttgttttgc aacttcaggt ccgggagcaa caaatttagt tactggaatt gcaaccgctg    780
atatggattc tataccaatg attttaatta ctggtcaggt aggtagagca tttattggaa    840
cagatgcttt tcaagaagtt gatatctaca acataactaa accaattgta aaggcttcgt    900
atgttgtaaa tgatgcaagt atgattccag aaatcgtttc tgaagccttt tacttggcaa    960
aaaatggtcg tcctggtcca gttttaattg acattcccaa agatgtagga ttagaagaaa   1020
taactcagta tgtacctata tatcaacaag aaactactaa aaataaacga tatgaatttt   1080
tatttcaaac tccctttgat caaattcgtt ccgctttaac attaataaaa caatcatcac   1140
aaccgttgtt ttatgttggt ggaggagctg ttttagctga agctcgccaa gaacttttag   1200
```

```
ctttagcaga aacatttgaa attcctgtta caacaacatt aatgggaaaa ggagcttttc    1260
atgaaaacca tcgtttatat ttaggaatgc tgggtatgca tggtacaggt tatgctaatt    1320
ttgcagtaag tgagtgtgat ttacttatag caataggtgc aagatttgat gatcgggtta    1380
ctggtaaact tgaagatttc gcctctcaag cacaaattct tcaaattgat attgatccaa    1440
atgaaattgg aaaaaataag atacctcatt tagctattat tggagatata aaaaagtttt    1500
tacaacaatt gttaaaacat tcaaattcag taactccttt atatgacgca acacaaacta    1560
gattttggcg agaaagaatt ttaaaatgga agagcgttat ccattaatt attccaaacg     1620 tagataccgg tttatcacct cagcaaattg taaatcgttt agctgaactt cttccaaatg    1680
cctattttac tacagacgtt ggtcagcatc aaatgtgggc agcccaattt ctaaaatgta    1740
atcttagaaa atggatgtca agtgctgggt taggtactat gggttatggt ttaccagcag    1800
caataggagt tcaattagca tttcccaatt caaatgtagt ttgtattagt ggagatgcta    1860
gttttcaaat gaatcttcaa gagttaggaa aatagcaca gtataatcta cccattaaaa    1920
tctttatttt aaataatcgt tggcaaggta tggtacgaca atggcaacag tcttttttatg   1980 atgaaagata ttcacattcc tctatgaaag atggtatgcc agactttgtt aaactcgctg    2040
agtcttatgg aattaaaggg tgccgtataa aaacagttga agaatttcaa aaaatagaaa    2100
atgatattgt tttagcaaac caaccattat tgattgactt tgatgtaacc gaaactgaaa    2160
attgttatcc aatggttgca ccaggtaaaa gtaattcaca aatgatcgga ttaagtaatg    2220
aatcatctct gcagactact actaaaaaaa tatttatta aataggccga gttggatttg     2280
aaccaacgta ggctgagcca gcggatttac agtccgcccc ctttaaccac tcgggcatcg    2340
accctacttt tattaaatta tgcactaaac caatatattt ataaatctaa tgcttaaagc    2400
attagattta taaatatgtc gaataaagag ctataccaat tgctgctaca atactaccaa    2460
ttaaaccacc actaaagaag ccctctgaaa atttttgcca gcctaaaata gtatctagtt    2520
cgcttgttcc tttaatctga ggtaattctt gtgttttttc tgaacctacc atttgttgta    2580
caagtttaac aataagagcg ttatcataaa cgtcgtaagt aacttggccg taaattgata    2640
atcctacagt taaaattaat aataacgtta tagcggcaag aagacctgca gctaacgaag    2700
taagtgaaaa ttctgcagag cgcaatggac cataagtgta aacggtcct ataagaaagt     2760 aaccatgtgt aaaaccaatt                                                2780
```

<210> SEQ ID NO 5
<211> LENGTH: 592
<212> TYPE: PRT
<213> ORGANISM: Nannochloropsis oculata
<220> FEATURE:
<221> NAME/KEY: misc_feature
<223> OTHER INFORMATION: SGI peptide ID No12345
<220> FEATURE:
<221> NAME/KEY: misc_feature
<223> OTHER INFORMATION: acetohydroxyacid synthase
<220> FEATURE:
<221> NAME/KEY: misc_feature
<222> LOCATION: (48)..(50)
<223> OTHER INFORMATION: substantially conserved sub-sequence D

<400> SEQUENCE: 5

Val Lys Ile Lys Lys Gln Thr Arg Arg Ile His Thr Gly Ala Phe Ala
1               5                   10                  15

Leu Ile Asp Ser Leu Val Arg Asn Gly Gly Lys Thr Ile Phe Gly Tyr
            20                  25                  30

-continued

```
Pro Gly Gly Ala Ile Leu Pro Ile Tyr Asp Glu Leu Tyr Leu Trp Glu
             35                  40                  45

Glu Glu Gly Leu Ile Glu His Ile Leu Val Arg His Glu Gln Gly Ala
 50                  55                  60

Ala His Ala Ala Asp Ala Tyr Ser Arg Ala Ser Gly Lys Val Gly Ile
 65                  70                  75                  80

Cys Phe Ala Thr Ser Gly Pro Gly Ala Thr Asn Leu Val Thr Gly Ile
                 85                  90                  95

Ala Thr Ala Asp Met Asp Ser Ile Pro Met Ile Val Ile Thr Gly Gln
            100                 105                 110

Val Gly Arg Ala Phe Ile Gly Thr Asp Ala Phe Gln Glu Val Asp Ile
        115                 120                 125

Tyr Asn Ile Thr Lys Pro Ile Val Lys Ala Ser Tyr Val Ile Asn Asp
130                 135                 140

Val Ser Thr Ile Ala Glu Ile Val Ser Glu Ala Phe Tyr Leu Ala Lys
145                 150                 155                 160

Asn Gly Arg Pro Gly Pro Val Leu Ile Asp Ile Pro Lys Asp Val Gly
                165                 170                 175

Leu Glu Glu Ile Asn Gln Tyr Leu Pro Ile Tyr Gln Gln Glu Thr Thr
            180                 185                 190

Lys Asn Lys Arg Tyr Glu Phe Leu Phe Gln Thr Pro Phe Ala Gln Ile
        195                 200                 205

Arg Ser Ala Leu Thr Leu Met Arg Gln Ser Ser Gln Pro Leu Leu Tyr
210                 215                 220

Val Gly Gly Gly Ala Val Leu Ala Glu Ala Arg Gln Glu Leu Leu Ala
225                 230                 235                 240

Leu Ala Glu Thr Phe Glu Ile Pro Val Thr Thr Thr Leu Met Gly Lys
                245                 250                 255

Gly Ala Phe His Glu Asn His Arg Leu Tyr Leu Gly Met Leu Gly Met
            260                 265                 270

His Gly Thr Gly Tyr Ala Asn Phe Ala Val Ser Glu Cys Asp Leu Leu
        275                 280                 285

Ile Ala Ile Gly Ala Arg Phe Asp Asp Arg Val Thr Gly Lys Leu Glu
290                 295                 300

Asp Phe Ala Ser Gln Ala Gln Ile Leu Gln Ile Asp Ile Asp Pro Asn
305                 310                 315                 320

Glu Ile Gly Lys Asn Lys Ile Pro His Leu Ala Ile Gly Asp Ile
                325                 330                 335

Lys Lys Val Leu His Gln Leu Leu Lys His Ser Ser Thr Ile Thr Pro
            340                 345                 350

Ser Tyr Asp Ala Thr Gln Thr Arg Phe Trp Arg Glu Arg Ile Val Lys
        355                 360                 365

Trp Lys Glu Arg Tyr Pro Leu Ile Ile Pro Ser Ile Pro Leu Gly Leu
370                 375                 380

Ser Pro Gln Gln Ile Val Asn Arg Val Ala Glu Leu Leu Pro Asn Ala
385                 390                 395                 400

Tyr Phe Thr Thr Asp Val Gly Gln His Gln Met Trp Ala Ala Gln Phe
                405                 410                 415

Leu Lys Cys Asn Ile Thr Lys Trp Met Ser Ser Ala Gly Leu Gly Thr
            420                 425                 430

Met Gly Tyr Gly Leu Pro Ala Ala Ile Gly Ala Gln Leu Ala Phe Ser
        435                 440                 445

Asn Ser Asn Val Ile Cys Ile Thr Gly Asp Ala Ser Phe Gln Met Asn
```

Ile Gln Glu Leu Gly Thr Ile Ala Gln Tyr Asn Leu Pro Ile Lys Ile
465                 470                 475                 480

Leu Ile Leu Asn Asn Arg Trp Gln Gly Met Val Arg Gln Trp Gln Gln
            485                 490                 495

Ser Phe Tyr Asp Glu Arg Tyr Ser His Ser Ser Met Lys Asp Gly Met
            500                 505                 510

Pro Asp Phe Val Lys Leu Ala Glu Ser Tyr Gly Ile Lys Gly Tyr Arg
            515                 520                 525

Ile Lys Thr Pro Glu Glu Phe Ala Glu Ile Glu Asn Glu Ile Val Ser
            530                 535                 540

Thr Asn Gln Ala Met Leu Ile Asp Phe Glu Val Asn Glu Thr Glu Asn
545                 550                 555                 560

Cys Tyr Pro Met Val Ala Pro Gly Lys Ser Asn Ser Gln Met Ile Gly
            565                 570                 575

Leu Ser Ala Glu Ser Ser Val His Ser Thr Thr Lys Lys Thr Phe Ser
            580                 585                 590

<210> SEQ ID NO 6
<211> LENGTH: 2463
<212> TYPE: DNA
<213> ORGANISM: Nannochloropsis oculata
<220> FEATURE:
<221> NAME/KEY: misc_feature
<223> OTHER INFORMATION: SGI Gene ID No12345
<220> FEATURE:
<221> NAME/KEY: misc_feature
<223> OTHER INFORMATION: acetohydroxyacid synthase
<220> FEATURE:
<221> NAME/KEY: misc_feature
<223> OTHER INFORMATION: encodes the peptide sequence at SEQ ID NO 5

<400> SEQUENCE: 6
ctgattttct tgttttagat ttattcataa aataactctt cgatttgttc ctaaaatagt      60
ataaaatact atacaattaa aagagataaa aaacaagtaa ttcttaactg cttatgttaa     120
gtttaattaa cttttaaagt attttaattt ttagtaaaaa taaataaatc aaaattttat     180
gttttttgaa atagcaattc aaaatttaat tttataaaaa agttgaaaag gtaaataagt     240
gaaaatcaag aaacaaactc gaagaataca cactggtgca ttcgcattaa ttgatagttt     300
agtacgtaat ggtggaaaaa cgatctttgg ttatccaggt ggtgcaattt tacctattta     360
tgacgagtta tacctttggg aagaagaagg actaattgaa catatttag tccgacatga     420 acaaggtgct gcgcatgccg ctgatgccta ttctcgtgca agtggtaagg taggtatttg     480
ttttgcaact tcaggtccgg gagcaacaaa cttagttact ggaattgcaa ctgccgatat     540
ggactcaatt ccaatgattg taattactgg tcaggtaggt cgagcattca ttggaacgga     600
tgcatttcaa gaagtagaca tttacaatat aacaaaacca attgtaaaag cttcttacgt     660
tattaatgat gtaagtacta ttgcagaaat tgtgtcagaa gccttttatt tagcaaaaaa     720
cggtcgtcct ggccctgttt taattgatat acctaaggac gtaggattag aagaaataaa     780
tcagtattta cccatttatc aacaggagac aacaaaaaat aagcgttatg aatttttatt     840
tcaaactcct tttgctcaaa ttcgttcagc cttaacattg atgagacaat cttctcaacc     900
tttattatat gtaggaggag gagccgtttt agctgaagct agacaagaac tattagcttt     960
agctgaaaca tttgaaatac cggtaacaac cacactaatg ggaaaaggtg cttttcatga    1020
aaaccaccgt ttatatttag gaatgttagg tatgcacggt actggatatg ctaatttcgc    1080

-continued

```
agtaagtgaa tgtgatttac ttatagccat tggagcgaga tttgatgata gggttactgg    1140
taaacttgaa gattttgctt cacaagcaca aattcttcaa attgatatag acccaaatga    1200
aataggtaaa aataaaattc cacatttagc tattattggt gatattaaaa aagttttaca    1260
ccagttgtta aaacattcaa gtacgataac accttcatac gatgctacac aaacaagatt    1320
ttggcgagaa cgaatagtaa aatggaaaga gcgctatccc ttaattattc ctagtatacc    1380
tttaggttta tctcctcaac aaattgttaa tcgtgttgct gaacttcttc caaatgcata    1440
ttttactacg gatgttggac agcatcaaat gtgggcggct caattttaa aatgtaatat     1500 tacaaaatgg atgtcaagcg ccggtttagg tactatggga tatggtttac ctgctgcaat    1560
aggtgcacaa ttagcttttt ctaattcaaa cgtaatttgt attacgggag acgctagttt    1620
tcaaatgaat atacaagaac ttggaactat agcacaatat aatttaccaa tcaaaattct    1680
tatcttaaat aatcgctggc aaggtatggt acgtcaatgg caacaatcct tttatgatga    1740
gcgttattca cattcttcta tgaaagatgg aatgcctgat tttgttaaac ttgcagagtc    1800
atatggtatt aagggttacc gaataaaaac tcctgaagaa tttgccgaaa tagaaaatga    1860
gattgtttca acaaatcaag caatgttaat tgattttgaa gtaaatgaaa ctgaaaattg    1920
ttacccaatg gttgcacctg gtaaaagtaa ttctcaaatg attggtttaa gtgcagagtc    1980
ttctgtacat agcaccacta aaaaaacttt ttcataaata ggccgagttg gatttgaacc    2040
aacgtaggct gagccagcgg atttacagtc cgcccccttt aaccactcgg gcatcgaccc    2100
tattctttat tagattatgc aataatttag aatatttata aatctaatgc tttaagcatt    2160
agatttataa gtacgttgag tataaagcta taccaactgc agcaacgatg ctaccgatta    2220
gtccaccact aaagaatccc tcagagaatt tttgccaacc tagaacagta tctagttcgc    2280
ttgttccttt aatttgaggt aagtcttgtg tttttttctga tcctaccatt tgacgtacaa    2340
gttttacgat aagagcatta tcataaacat cataagtaac ctgtccataa atcgataatc    2400
ctactgttaa aattaatagt agagttattg cagcaagtag acctgcagct aatgacgtaa    2460
gtg                                                                  2463
```

<210> SEQ ID NO 7
<211> LENGTH: 587
<212> TYPE: PRT
<213> ORGANISM: Porphyridium sp.
<220> FEATURE:
<221> NAME/KEY: misc_feature
<223> OTHER INFORMATION: acetohydroxyacid synthase

<400> SEQUENCE: 7

```
Met Thr His Ile Glu Lys Ser Asn Tyr Gln Glu Gln Thr Gly Ala Phe
1               5                   10                  15

Ala Leu Leu Asp Ser Leu Val Arg His Lys Val Lys His Ile Phe Gly
            20                  25                  30

Tyr Pro Gly Gly Ala Ile Leu Pro Ile Tyr Asp Glu Leu Tyr Lys Trp
        35                  40                  45

Glu Glu Gln Gly Tyr Ile Lys His Ile Leu Val Arg His Glu Gln Gly
    50                  55                  60

Ala Ala His Ala Ala Asp Gly Tyr Ala Arg Ala Thr Gly Glu Val Gly
65                  70                  75                  80

Val Cys Phe Ala Thr Ser Gly Pro Gly Ala Thr Asn Leu Val Thr Gly
                85                  90                  95

Ile Ala Thr Ala His Met Asp Ser Ile Pro Ile Val Ile Ile Thr Gly
            100                 105                 110
```

-continued

```
Gln Val Gly Arg Ser Phe Ile Gly Thr Asp Ala Phe Gln Glu Val Asp
            115                 120                 125
Ile Phe Gly Ile Thr Leu Pro Ile Val Lys His Ser Tyr Val Ile Arg
        130                 135                 140
Asp Pro Arg Asp Ile Pro Arg Ile Val Ala Glu Ala Phe Ser Ile Ala
145                 150                 155                 160
Lys Gln Gly Arg Pro Gly Pro Val Leu Ile Asp Val Pro Lys Asp Val
                165                 170                 175
Gly Leu Glu Thr Phe Glu Tyr Gln Tyr Val Asn Pro Gly Glu Ala Arg
            180                 185                 190
Ile Pro Gly Phe Arg Asp Leu Val Ala Pro Ser Ser Arg Gln Ile Ile
        195                 200                 205
His Ser Ile Gln Leu Ile Gln Glu Ala Asn Gln Pro Leu Leu Tyr Val
    210                 215                 220
Gly Gly Gly Ala Ile Thr Ser Gly Ala His Asp Leu Ile Tyr Lys Leu
225                 230                 235                 240
Val Asn Gln Tyr Lys Ile Pro Ile Thr Thr Thr Leu Met Gly Lys Gly
                245                 250                 255
Ile Ile Asp Glu Gln Asn Pro Leu Ala Leu Gly Met Leu Gly Met His
            260                 265                 270
Gly Thr Ala Tyr Ala Asn Phe Ala Val Ser Glu Cys Asp Leu Leu Ile
        275                 280                 285
Thr Leu Gly Ala Arg Phe Asp Asp Arg Val Thr Gly Lys Leu Asp Glu
    290                 295                 300
Phe Ala Cys Asn Ala Lys Val Ile His Val Asp Ile Asp Pro Ala Glu
305                 310                 315                 320
Val Gly Lys Asn Arg Ile Pro Gln Val Ala Ile Val Gly Asp Ile Ser
                325                 330                 335
Leu Val Leu Glu Gln Trp Leu Leu Tyr Leu Asp Arg Asn Leu Gln Leu
            340                 345                 350
Asp Asp Ser His Leu Arg Ser Trp His Glu Arg Ile Phe Arg Trp Arg
        355                 360                 365
Gln Glu Tyr Pro Leu Ile Val Pro Lys Leu Val Gln Thr Leu Ser Pro
    370                 375                 380
Gln Glu Ile Ile Ala Asn Ile Ser Gln Ile Met Pro Asp Ala Tyr Phe
385                 390                 395                 400
Ser Thr Asp Val Gly Gln His Gln Met Trp Ala Ala Gln Phe Val Lys
                405                 410                 415
Thr Leu Pro Arg Arg Trp Leu Ser Ser Gly Leu Gly Thr Met Gly
            420                 425                 430
Tyr Gly Leu Pro Ala Ala Ile Gly Ala Lys Ile Ala Tyr Pro Glu Ser
        435                 440                 445
Pro Val Val Cys Ile Thr Gly Asp Ser Ser Phe Gln Met Asn Ile Gln
    450                 455                 460
Glu Leu Gly Thr Ile Ala Gln Tyr Lys Leu Asp Ile Lys Ile Ile Ile
465                 470                 475                 480
Ile Asn Asn Lys Trp Gln Gly Met Val Arg Gln Trp Gln Gln Ala Phe
                485                 490                 495
Tyr Gly Ala Arg Tyr Ser His Ser Arg Met Glu Asp Gly Ala Pro Asn
            500                 505                 510
Phe Val Ala Leu Ala Lys Ser Phe Gly Ile Asp Gly Gln Ser Ile Ser
        515                 520                 525
```

```
Thr Arg Gln Glu Met Asp Ser Leu Phe Asn Thr Ile Ile Lys Tyr Lys
        530                 535                 540

Gly Pro Met Val Ile Asp Cys Lys Val Ile Glu Asp Glu Asn Cys Tyr
545                 550                 555                 560

Pro Met Val Ala Pro Gly Lys Ser Asn Ala Gln Met Ile Gly Leu Asp
                565                 570                 575

Lys Ser Asn Asn Glu Ile Ile Lys Ile Lys Glu
                580                 585

<210> SEQ ID NO 8
<211> LENGTH: 670
<212> TYPE: PRT
<213> ORGANISM: Arabidopsis thaliana
<220> FEATURE:
<221> NAME/KEY: misc_feature
<223> OTHER INFORMATION: acetohydroxyacid synthase

<400> SEQUENCE: 8

Met Ala Ala Thr Thr Thr Thr Thr Ser Ser Ser Ile Ser Phe
1               5                   10                  15

Ser Thr Lys Pro Ser Pro Ser Ser Lys Ser Pro Leu Pro Ile Ser
                20                  25                  30

Arg Phe Ser Leu Pro Phe Ser Leu Asn Pro Asn Lys Ser Ser Ser Ser
                35                  40                  45

Ser Arg Arg Arg Gly Ile Lys Ser Ser Pro Ser Ser Ile Ser Ala
50                  55                  60

Val Leu Asn Thr Thr Thr Asn Val Thr Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala Asp Ile Leu Val Glu Ala Leu Glu Arg Gln Gly Val
                100                 105                 110

Glu Thr Val Phe Ala Tyr Pro Gly Gly Ala Ser Met Glu Ile His Gln
                115                 120                 125

Ala Leu Thr Arg Ser Ser Ser Ile Arg Asn Val Leu Pro Arg His Glu
                130                 135                 140

Gln Gly Gly Val Phe Ala Ala Glu Gly Tyr Ala Arg Ser Ser Gly Lys
145                 150                 155                 160

Pro Gly Ile Cys Ile Ala Thr Ser Gly Pro Gly Ala Thr Asn Leu Val
                165                 170                 175

Ser Gly Leu Ala Asp Ala Leu Leu Asp Ser Val Pro Leu Val Ala Ile
                180                 185                 190

Thr Gly Gln Val Pro Arg Arg Met Ile Gly Thr Asp Ala Phe Gln Glu
                195                 200                 205

Thr Pro Ile Val Glu Val Thr Arg Ser Ile Thr Lys His Asn Tyr Leu
                210                 215                 220

Val Met Asp Val Glu Asp Ile Pro Arg Ile Ile Glu Glu Ala Phe Phe
225                 230                 235                 240

Leu Ala Thr Ser Gly Arg Pro Gly Pro Val Leu Val Asp Val Pro Lys
                245                 250                 255

Asp Ile Gln Gln Gln Leu Ala Ile Pro Asn Trp Glu Gln Ala Met Arg
                260                 265                 270

Leu Pro Gly Tyr Met Ser Arg Met Pro Lys Pro Pro Glu Asp Ser His
                275                 280                 285

Leu Glu Gln Ile Val Arg Leu Ile Ser Glu Ser Lys Lys Pro Val Leu
                290                 295                 300
```

Tyr Val Gly Gly Gly Cys Leu Asn Ser Ser Asp Glu Leu Gly Arg Phe
305                 310                 315                 320

Val Glu Leu Thr Gly Ile Pro Val Ala Ser Thr Leu Met Gly Leu Gly
            325                 330                 335

Ser Tyr Pro Cys Asp Asp Glu Leu Ser Leu His Met Leu Gly Met His
            340                 345                 350

Gly Thr Val Tyr Ala Asn Tyr Ala Val Glu His Ser Asp Leu Leu Leu
            355                 360                 365

Ala Phe Gly Val Arg Phe Asp Asp Arg Val Thr Gly Lys Leu Glu Ala
370                 375                 380

Phe Ala Ser Arg Ala Lys Ile Val His Ile Asp Ile Asp Ser Ala Glu
385                 390                 395                 400

Ile Gly Lys Asn Lys Thr Pro His Val Ser Val Cys Gly Asp Val Lys
            405                 410                 415

Leu Ala Leu Gln Gly Met Asn Lys Val Leu Glu Asn Arg Ala Glu Glu
            420                 425                 430

Leu Lys Leu Asp Phe Gly Val Trp Arg Asn Glu Leu Asn Val Gln Lys
435                 440                 445

Gln Lys Phe Pro Leu Ser Phe Lys Thr Phe Gly Glu Ala Ile Pro Pro
450                 455                 460

Gln Tyr Ala Ile Lys Val Leu Asp Glu Leu Thr Asp Gly Lys Ala Ile
465                 470                 475                 480

Ile Ser Thr Gly Val Gly Gln His Gln Met Trp Ala Ala Gln Phe Tyr
            485                 490                 495

Asn Tyr Lys Lys Pro Arg Gln Trp Leu Ser Ser Gly Gly Leu Gly Ala
            500                 505                 510

Met Gly Phe Gly Leu Pro Ala Ala Ile Gly Ala Ser Val Ala Asn Pro
            515                 520                 525

Asp Ala Ile Val Val Asp Ile Asp Gly Asp Gly Ser Phe Ile Met Asn
530                 535                 540

Val Gln Glu Leu Ala Thr Ile Arg Val Glu Asn Leu Pro Val Lys Val
545                 550                 555                 560

Leu Leu Leu Asn Asn Gln His Leu Gly Met Val Met Gln Trp Glu Asp
            565                 570                 575

Arg Phe Tyr Lys Ala Asn Arg Ala His Thr Phe Leu Gly Asp Pro Ala
            580                 585                 590

Gln Glu Asp Glu Ile Phe Pro Asn Met Leu Leu Phe Ala Ala Ala Cys
            595                 600                 605

Gly Ile Pro Ala Ala Arg Val Thr Lys Lys Ala Asp Leu Arg Glu Ala
610                 615                 620

Ile Gln Thr Met Leu Asp Thr Pro Gly Pro Tyr Leu Leu Asp Val Ile
625                 630                 635                 640

Cys Pro His Gln Glu His Val Leu Pro Met Ile Pro Ser Gly Gly Thr
            645                 650                 655

Phe Asn Asp Val Ile Thr Glu Gly Asp Gly Arg Ile Lys Tyr
            660                 665                 670

<210> SEQ ID NO 9
<211> LENGTH: 686
<212> TYPE: PRT
<213> ORGANISM: Saccharomyces cerevisiae
<220> FEATURE:
<221> NAME/KEY: misc_feature
<223> OTHER INFORMATION: acetohydroxyacid synthase

```
<400> SEQUENCE: 9

Met Ile Arg Gln Ser Thr Leu Lys Asn Phe Ala Ile Lys Arg Cys Phe
1               5                   10                  15

Gln His Ile Ala Tyr Arg Asn Thr Pro Ala Met Arg Ser Val Ala Leu
            20                  25                  30

Ala Gln Arg Phe Tyr Ser Ser Ser Arg Tyr Tyr Ser Ala Ser Pro
        35                  40                  45

Leu Pro Ala Ser Lys Arg Pro Glu Pro Ala Pro Ser Phe Asn Val Asp
    50                  55                  60

Pro Leu Glu Gln Pro Ala Glu Pro Ser Lys Leu Ala Lys Lys Leu Arg
65                  70                  75                  80

Ala Glu Pro Asp Met Asp Thr Ser Phe Val Gly Leu Thr Gly Gly Gln
                85                  90                  95

Ile Phe Asn Glu Met Met Ser Arg Gln Asn Val Asp Thr Val Phe Gly
            100                 105                 110

Tyr Pro Gly Gly Ala Ile Leu Pro Val Tyr Asp Ala Ile His Asn Ser
        115                 120                 125

Asp Lys Phe Asn Phe Val Leu Pro Lys His Glu Gln Gly Ala Gly His
    130                 135                 140

Met Ala Glu Gly Tyr Ala Arg Ala Ser Gly Lys Pro Gly Val Val Leu
145                 150                 155                 160

Val Thr Ser Gly Pro Gly Ala Thr Asn Val Val Thr Pro Met Ala Asp
                165                 170                 175

Ala Phe Ala Asp Gly Ile Pro Met Val Val Phe Thr Gly Gln Val Pro
            180                 185                 190

Thr Ser Ala Ile Gly Thr Asp Ala Phe Gln Glu Ala Asp Val Val Gly
        195                 200                 205

Ile Ser Arg Ser Cys Thr Lys Trp Asn Val Met Val Lys Ser Val Glu
    210                 215                 220

Glu Leu Pro Leu Arg Ile Asn Glu Ala Phe Glu Ile Ala Thr Ser Gly
225                 230                 235                 240

Arg Pro Gly Pro Val Leu Val Asp Leu Pro Lys Asp Val Thr Ala Ala
                245                 250                 255

Ile Leu Arg Asn Pro Ile Pro Thr Lys Thr Thr Leu Pro Ser Asn Ala
            260                 265                 270

Leu Asn Gln Leu Thr Ser Arg Ala Gln Asp Glu Phe Val Met Gln Ser
        275                 280                 285

Ile Asn Lys Ala Ala Asp Leu Ile Asn Leu Ala Lys Lys Pro Val Leu
    290                 295                 300

Tyr Val Gly Ala Gly Ile Leu Asn His Ala Asp Gly Pro Arg Leu Leu
305                 310                 315                 320

Lys Glu Leu Ser Asp Arg Ala Gln Ile Pro Val Thr Thr Thr Leu Gln
                325                 330                 335

Gly Leu Gly Ser Phe Asp Gln Glu Asp Pro Lys Ser Leu Asp Met Leu
            340                 345                 350

Gly Met His Gly Cys Ala Thr Ala Asn Leu Ala Val Gln Asn Ala Asp
        355                 360                 365

Leu Ile Ile Ala Val Gly Ala Arg Phe Asp Asp Arg Val Thr Gly Asn
    370                 375                 380

Ile Ser Lys Phe Ala Pro Glu Ala Arg Arg Ala Ala Ala Glu Gly Arg
385                 390                 395                 400

Gly Gly Ile Ile His Phe Glu Val Ser Pro Lys Asn Ile Asn Lys Val
                405                 410                 415
```

Val Gln Thr Gln Ile Ala Val Glu Gly Asp Ala Thr Thr Asn Leu Gly
              420                 425                 430

Lys Met Met Ser Lys Ile Phe Pro Val Lys Glu Arg Ser Glu Trp Phe
              435                 440                 445

Ala Gln Ile Asn Lys Trp Lys Lys Glu Tyr Pro Tyr Ala Tyr Met Glu
        450                 455                 460

Glu Thr Pro Gly Ser Lys Ile Lys Pro Gln Thr Val Ile Lys Lys Leu
465                 470                 475                 480

Ser Lys Val Ala Asn Asp Thr Gly Arg His Val Ile Val Thr Thr Gly
                485                 490                 495

Val Gly Gln His Gln Met Trp Ala Ala Gln His Trp Thr Trp Arg Asn
            500                 505                 510

Pro His Thr Phe Ile Thr Ser Gly Leu Gly Thr Met Gly Tyr Gly
            515                 520                 525

Leu Pro Ala Ala Ile Gly Ala Gln Val Ala Lys Pro Glu Ser Leu Val
            530                 535                 540

Ile Asp Ile Asp Gly Asp Ala Ser Phe Asn Met Thr Leu Thr Glu Leu
545                 550                 555                 560

Ser Ser Ala Val Gln Ala Gly Thr Pro Val Lys Ile Leu Ile Leu Asn
                565                 570                 575

Asn Glu Glu Gln Gly Met Val Thr Gln Trp Gln Ser Leu Phe Tyr Glu
            580                 585                 590

His Arg Tyr Ser His Thr His Gln Leu Asn Pro Asp Phe Ile Lys Leu
            595                 600                 605

Ala Glu Ala Met Gly Leu Lys Gly Leu Arg Val Lys Lys Gln Glu Glu
        610                 615                 620

Leu Asp Ala Lys Leu Lys Glu Phe Val Ser Thr Lys Gly Pro Val Leu
625                 630                 635                 640

Leu Glu Val Glu Val Asp Lys Lys Val Pro Val Leu Pro Met Val Ala
                645                 650                 655

Gly Gly Ser Gly Leu Asp Glu Phe Ile Asn Phe Asp Pro Glu Val Glu
            660                 665                 670

Arg Gln Gln Thr Glu Leu Arg His Lys Arg Thr Gly Gly Lys
        675                 680                 685

<210> SEQ ID NO 10
<211> LENGTH: 683
<212> TYPE: PRT
<213> ORGANISM: Chlamydomonas reinhardtii
<220> FEATURE:
<221> NAME/KEY: misc_feature
<223> OTHER INFORMATION: acetohydroxyacid synthase

<400> SEQUENCE: 10

Met Lys Ala Leu Arg Ser Gly Thr Ala Val Ala Arg Gly Gln Ala Gly
1               5                   10                  15

Cys Val Ser Pro Ala Pro Arg Pro Val Pro Met Ser Ser Gln Thr Met
                20                  25                  30

Ile Pro Ser Thr Ser Ser Pro Ala Thr Arg Ala Pro Ala Arg Ser Gly
            35                  40                  45

Arg Arg Ala Leu Ala Val Ser Ala Lys Leu Ala Asp Gly Ser Arg Arg
        50                  55                  60

Met Gln Ser Glu Glu Val Arg Arg Ala Lys Glu Val Ala Gln Ala Ala
65                  70                  75                  80

Leu Ala Lys Asp Ser Pro Ala Asp Trp Val Asp Arg Tyr Gly Ser Glu

```
                   85                  90                  95

Pro Arg Lys Gly Ala Asp Ile Leu Val Gln Ala Leu Glu Arg Glu Gly
            100                 105                 110

Val Asp Ser Val Phe Ala Tyr Pro Gly Gly Ala Ser Met Glu Ile His
            115                 120                 125

Gln Ala Leu Thr Arg Ser Asp Arg Ile Thr Asn Val Leu Cys Arg His
            130                 135                 140

Glu Gln Gly Glu Ile Phe Ala Ala Glu Gly Tyr Ala Lys Ala Ala Gly
145                 150                 155                 160

Arg Val Gly Val Cys Ile Ala Thr Ser Gly Pro Gly Ala Thr Asn Leu
                165                 170                 175

Val Thr Gly Leu Ala Asp Ala Met Met Asp Ser Ile Pro Leu Val Ala
                180                 185                 190

Ile Thr Gly Gln Val Pro Arg Arg Met Ile Gly Thr Asp Ala Phe Gln
                195                 200                 205

Glu Thr Pro Ile Val Glu Val Thr Arg Ala Ile Thr Lys His Asn Tyr
            210                 215                 220

Leu Val Leu Asp Ile Lys Asp Leu Pro Arg Val Ile Lys Glu Ala Phe
225                 230                 235                 240

Tyr Leu Ala Arg Thr Gly Arg Pro Gly Pro Val Leu Val Asp Val Pro
                245                 250                 255

Lys Asp Ile Gln Gln Leu Ala Val Pro Asp Trp Glu Ala Pro Met
                260                 265                 270

Ser Ile Thr Gly Tyr Ile Ser Arg Leu Pro Pro Val Glu Glu Ser
                275                 280                 285

Gln Val Leu Pro Val Leu Arg Ala Leu Gln Gly Ala Ala Lys Pro Val
290                 295                 300

Ile Tyr Tyr Gly Gly Gly Cys Leu Asp Ala Gln Ala Glu Leu Arg Glu
305                 310                 315                 320

Phe Ala Ala Arg Thr Gly Ile Pro Leu Ala Ser Thr Phe Met Gly Leu
                325                 330                 335

Gly Val Val Pro Ser Thr Asp Pro Asn His Leu Gln Met Leu Gly Met
                340                 345                 350

His Gly Thr Val Phe Ala Asn Tyr Ala Val Asp Gln Ala Asp Leu Leu
            355                 360                 365

Val Ala Leu Gly Val Arg Phe Asp Asp Arg Val Thr Gly Lys Leu Asp
370                 375                 380

Ala Phe Ala Ala Arg Ala Arg Ile Val His Ile Asp Ile Asp Ala Ala
385                 390                 395                 400

Glu Ile Ser Lys Asn Lys Thr Ala His Val Pro Val Cys Gly Asp Val
                405                 410                 415

Lys Gln Ala Leu Ser His Leu Asn Arg Leu Leu Ala Ala Glu Pro Leu
                420                 425                 430

Pro Ala Asp Lys Trp Ala Gly Trp Arg Ala Glu Leu Ala Ala Lys Arg
                435                 440                 445

Ala Glu Phe Pro Met Arg Tyr Pro Gln Arg Asp Asp Ala Ile Val Pro
            450                 455                 460

Gln His Ala Ile Gln Val Leu Gly Glu Glu Thr Gln Gly Glu Ala Ile
465                 470                 475                 480

Ile Thr Thr Gly Val Gly Gln His Gln Met Trp Ala Ala Gln Trp Tyr
                485                 490                 495

Pro Tyr Lys Glu Thr Arg Arg Trp Ile Ser Ser Gly Gly Leu Gly Ser
                500                 505                 510
```

Met Gly Phe Gly Leu Pro Ala Ala Leu Gly Ala Ala Val Ala Phe Asp
        515                 520                 525

Gly Lys Asn Gly Arg Pro Lys Lys Thr Val Val Asp Ile Asp Gly Asp
        530                 535                 540

Gly Ser Phe Leu Met Asn Val Gln Glu Leu Ala Thr Ile Phe Ile Glu
545                 550                 555                 560

Lys Leu Asp Val Lys Val Met Leu Leu Asn Asn Gln His Leu Gly Met
                565                 570                 575

Val Val Gln Trp Glu Asp Arg Phe Tyr Lys Ala Asn Arg Ala His Thr
                580                 585                 590

Tyr Leu Gly Lys Arg Glu Ser Glu Trp His Ala Thr Gln Asp Glu Glu
        595                 600                 605

Asp Ile Tyr Pro Asn Phe Val Asn Met Ala Gln Ala Phe Gly Val Pro
        610                 615                 620

Ser Arg Arg Val Ile Val Lys Glu Gln Leu Arg Gly Ala Ile Arg Thr
625                 630                 635                 640

Met Leu Asp Thr Pro Gly Pro Tyr Leu Leu Glu Val Met Val Pro His
                645                 650                 655

Ile Glu His Val Leu Pro Met Ile Pro Gly Gly Ala Ser Phe Lys Asp
                660                 665                 670

Ile Ile Thr Glu Gly Asp Gly Thr Val Lys Tyr
        675                 680

<210> SEQ ID NO 11
<211> LENGTH: 502
<212> TYPE: DNA
<213> ORGANISM: Nannochloropsis gaditana
<220> FEATURE:
<221> NAME/KEY: misc_feature
<223> OTHER INFORMATION: SGI Gene ID Ng12345
<220> FEATURE:
<221> NAME/KEY: misc_feature
<223> OTHER INFORMATION: acetohydroxyacid synthase promoter region
<220> FEATURE:
<221> NAME/KEY: misc_feature
<223> OTHER INFORMATION: portion of SEQ ID NO 2

<400> SEQUENCE: 11
agagtggctc ccaacatatc cttttgcaag ccctaagatt ttttttctag attttctagc      60
tatatttcct cttttaacac gtatcatttt attttatctc attttaattg ttaaagaact     120
tttttactgt taattttttca gtattcccta cagtaatagt agaacaaagc cttcttttc     180 tagaagaaga ttttttttgt aataaatggc ctttaaaggc ttttttttcta atgaaatttt    240 tatttgccgt tgtttatat cttttttaccg ctgattttct tgtttagat ttattcataa     300 aataactctt cgatttgttc gtaaaatagt ataaaatatt gtacaattaa aagagataaa     360
aaacaagcaa ttcttaacta aacgtattaa gtttgattaa cttcttaaat gttttaattt     420
ttaataaaaa taaattaatc aaagttttgt attttttaag cagatcaaaa tttaattta     480 aaaaattgaa aaaggtgaat aa                                              502

<210> SEQ ID NO 12
<211> LENGTH: 482
<212> TYPE: DNA
<213> ORGANISM: Nannochloropsis salina
<220> FEATURE:
<221> NAME/KEY: misc_feature
<223> OTHER INFORMATION: SGI Gene ID Ns12345
<220> FEATURE:
<221> NAME/KEY: misc_feature
<223> OTHER INFORMATION: acetohydroxyacid synthase promoter region
<220> FEATURE:
<221> NAME/KEY: misc_feature
<223> OTHER INFORMATION: portion of SEQ ID NO 4

<400> SEQUENCE: 12
cttttgcaag ccctaagact ttttttctag attttctagc tatatttcct cttctaacac     60
gtatcatttt actttatctc attttaattg ttaaagaact ttttactgt taattttca     120 gtatttccta cagtaatagt agaacaaagt cttctttttc tagaagaaga tttttttgt     180 aataaatggc ctttaaaggc tttttttcta atgaaatttt tatttgctgt tgtttatat     240 cttttaccg ccgatttct tgttttagat ttattcataa aataactctt cgatttgttc     300
gtaaaatagt ataaaatact atacaattaa aagagataaa aaacaagcaa ttcttgacta     360
aacgtattaa gttgattaa cttcttaaat gttttaattt ttaataaaaa taaattaatc     420
aaagttttgt attttttaag cagatcaaaa tttaattta aaaaattgaa aaaggtgaat     480
aa                                                                   482

<210> SEQ ID NO 13
<211> LENGTH: 238
<212> TYPE: DNA
<213> ORGANISM: Nannochloropsis oculata
<220> FEATURE:
<221> NAME/KEY: misc_feature
<223> OTHER INFORMATION: SGI Gene ID No12345
<220> FEATURE:
<221> NAME/KEY: misc_feature
<223> OTHER INFORMATION: acetohydroxyacid synthase promoter region
<220> FEATURE:
<221> NAME/KEY: misc_feature
<223> OTHER INFORMATION: portion of SEQ ID NO 6

<400> SEQUENCE: 13
ctgattttct tgttttagat ttattcataa aataactctt cgatttgttc ctaaaatagt     60
ataaaatact atacaattaa aagagataaa aaacaagtaa ttcttaactg cttatgttaa    120
gtttaattaa cttttaaagt attttaattt ttagtaaaaa taaataaatc aaaattttat    180
gttttttgaa atagcaattc aaaatttaat tttataaaaa agttgaaaag gtaaataa     238

<210> SEQ ID NO 14
<211> LENGTH: 37
<212> TYPE: DNA
<213> ORGANISM: Artificial Sequence
<220> FEATURE:
<223> OTHER INFORMATION: Primer oSGI-JU-75

<400> SEQUENCE: 14
cttctaaccc tacatcagtt ggaatatcaa ttaaaac                              37

<210> SEQ ID NO 15
<211> LENGTH: 37
<212> TYPE: DNA
<213> ORGANISM: Artificial Sequence
<220> FEATURE:
<223> OTHER INFORMATION: Primer oSGI-JU-76

<400> SEQUENCE: 15
gatattccaa ctgatgtagg gttagaagaa atagttc                              37

<210> SEQ ID NO 16
<211> LENGTH: 22
<212> TYPE: DNA
<213> ORGANISM: Artificial Sequence

```
<220> FEATURE:
<223> OTHER INFORMATION: Primer oSGI-JU-77

<400> SEQUENCE: 16
gcgtcatata aaggagttac tg                                              22

<210> SEQ ID NO 17
<211> LENGTH: 36
<212> TYPE: DNA
<213> ORGANISM: Artificial Sequence
<220> FEATURE:
<223> OTHER INFORMATION: Primer oSGI-JU-78

<400> SEQUENCE: 17
cggtacccgg ggatccagag tggctcccaa catatc                               36

<210> SEQ ID NO 18
<211> LENGTH: 35
<212> TYPE: DNA
<213> ORGANISM: Artificial Sequence
<220> FEATURE:
<223> OTHER INFORMATION: Primer oSGI-JU-79

<400> SEQUENCE: 18
cgactctaga ggatcacacc actttcaaga ggagc                                35

<210> SEQ ID NO 19
<211> LENGTH: 20
<212> TYPE: DNA
<213> ORGANISM: Artificial Sequence
<220> FEATURE:
<223> OTHER INFORMATION: Primer oSGI-JU-80

<400> SEQUENCE: 19
aaatggtcgt cctggtccag                                                 20

<210> SEQ ID NO 20
<211> LENGTH: 20
<212> TYPE: DNA
<213> ORGANISM: Artificial Sequence
<220> FEATURE:
<223> OTHER INFORMATION: Primer oSGI-JU-81

<400> SEQUENCE: 20
cgcctctcaa gcacaaattc                                                 20

<210> SEQ ID NO 21
<211> LENGTH: 22
<212> TYPE: DNA
<213> ORGANISM: Artificial Sequence
<220> FEATURE:
<223> OTHER INFORMATION: Primer oSGI-JU-84

<400> SEQUENCE: 21
acaccacttt caagaggagc tg                                              22

<210> SEQ ID NO 22
<211> LENGTH: 24
<212> TYPE: DNA
<213> ORGANISM: Artificial Sequence
<220> FEATURE:
<223> OTHER INFORMATION: Primer oSGI-JU-85

<400> SEQUENCE: 22
aaacaagcaa ttcttaacta aacg                                            24
```

```
<210> SEQ ID NO 23
<211> LENGTH: 26
<212> TYPE: DNA
<213> ORGANISM: Artificial Sequence
<220> FEATURE:
<223> OTHER INFORMATION: Primer oSGI-JU-108

<400> SEQUENCE: 23
tacctgacca gtaattaaaa tcattg                                                26

<210> SEQ ID NO 24
<211> LENGTH: 41
<212> TYPE: DNA
<213> ORGANISM: Artificial Sequence
<220> FEATURE:
<223> OTHER INFORMATION: Primer oSGI-JU-109

<400> SEQUENCE: 24
attactggtc aggtatcgag agcatttatt ggaacagatg c                               41

<210> SEQ ID NO 25
<211> LENGTH: 23
<212> TYPE: DNA
<213> ORGANISM: Artificial Sequence
<220> FEATURE:
<223> OTHER INFORMATION: Primer oSGI-JU-110

<400> SEQUENCE: 25
ttgtcgtacc ataccttgcc aac                                                   23

<210> SEQ ID NO 26
<211> LENGTH: 41
<212> TYPE: DNA
<213> ORGANISM: Artificial Sequence
<220> FEATURE:
<223> OTHER INFORMATION: Primer oSGI-JU-111

<400> SEQUENCE: 26
ggtatggtac gacaactgca acagtctttt tatgatgaaa g                               41

<210> SEQ ID NO 27
<211> LENGTH: 41
<212> TYPE: DNA
<213> ORGANISM: Artificial Sequence
<220> FEATURE:
<223> OTHER INFORMATION: Primer oSGI-JU-112

<400> SEQUENCE: 27
ggtatggtac gacaatcgca acagtctttt tatgatgaaa g                               41

<210> SEQ ID NO 28
<211> LENGTH: 23
<212> TYPE: DNA
<213> ORGANISM: Artificial Sequence
<220> FEATURE:
<223> OTHER INFORMATION: Primer oSGI-JU-113
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
```

<400> SEQUENCE: 28
athggnacng aygcnttcca aga					23

<210> SEQ ID NO 29
<211> LENGTH: 23
<212> TYPE: DNA
<213> ORGANISM: Artificial Sequence
<220> FEATURE:
<223> OTHER INFORMATION: Primer oSGI-JU-115
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 29
athggnacng aygcntttca aga					23

<210> SEQ ID NO 30
<211> LENGTH: 23
<212> TYPE: DNA
<213> ORGANISM: Artificial Sequence
<220> FEATURE:
<223> OTHER INFORMATION: Primer oSGI-JU-117
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 30
athggnacng aygcntttca aga					23

<210> SEQ ID NO 31
<211> LENGTH: 23
<212> TYPE: DNA
<213> ORGANISM: Artificial Sequence
<220> FEATURE:
<223> OTHER INFORMATION: Primer oSGI-JU-150

<400> SEQUENCE: 31
atcaaatctt gcacctattg cta					23

<210> SEQ ID NO 32
<211> LENGTH: 40
<212> TYPE: DNA
<213> ORGANISM: Artificial Sequence
<220> FEATURE:
<223> OTHER INFORMATION: Primer oSGI-JU-151

<400> SEQUENCE: 32
ggtgcaagat ttgataaccg ggttactggt aaacttgaag					40

<210> SEQ ID NO 33

```
<211> LENGTH: 492
<212> TYPE: PRT
<213> ORGANISM: Artificial Sequence
<220> FEATURE:
<223> OTHER INFORMATION: Synthetic construct: Consensus sequence from
      Figure 1

<400> SEQUENCE: 33
```

| | | | | | | | | | | | | | | | |
|---|---|---|---|---|---|---|---|---|---|---|---|---|---|---|---|
| Ile | Lys | Lys | Thr | Thr | Gly | Ala | Phe | Ala | Leu | Ile | Asp | Ser | Leu | Val | Arg |
| 1 | | | | 5 | | | | | 10 | | | | | 15 | |
| Asn | Gly | Val | Lys | Thr | Ile | Phe | Gly | Tyr | Pro | Gly | Gly | Ala | Ile | Leu | Pro |
| | | | 20 | | | | | 25 | | | | | 30 | | |
| Ile | Tyr | Asp | Glu | Leu | Tyr | Trp | Glu | Glu | Gly | Ile | His | Ile | Leu | Val | Arg |
| | | | 35 | | | | | 40 | | | | | 45 | | |
| His | Glu | Gln | Gly | Ala | Ala | His | Ala | Ala | Asp | Gly | Tyr | Ala | Arg | Ala | Ser |
| | 50 | | | | | 55 | | | | | 60 | | | | |
| Gly | Lys | Val | Gly | Ile | Cys | Phe | Ala | Thr | Ser | Gly | Pro | Gly | Ala | Thr | Asn |
| 65 | | | | | 70 | | | | | 75 | | | | | 80 |
| Leu | Val | Thr | Gly | Ile | Ala | Thr | Ala | Met | Asp | Ser | Ile | Pro | Met | Val | Leu |
| | | | | 85 | | | | | 90 | | | | | 95 | |
| Ile | Thr | Gly | Gln | Val | Gly | Arg | Ala | Phe | Ile | Gly | Thr | Asp | Ala | Phe | Gln |
| | | | 100 | | | | | 105 | | | | | 110 | | |
| Glu | Val | Asp | Ile | Tyr | Ile | Thr | Lys | Pro | Ile | Val | Lys | Ser | Tyr | Val | Val |
| | | 115 | | | | | 120 | | | | | 125 | | | |
| Asp | Val | Asp | Ile | Pro | Ile | Val | Ser | Glu | Ala | Phe | Tyr | Leu | Ala | Lys | Asn |
| | 130 | | | | | 135 | | | | | 140 | | | | |
| Gly | Arg | Pro | Gly | Pro | Val | Leu | Ile | Asp | Ile | Pro | Lys | Asp | Val | Gly | Leu |
| 145 | | | | | 150 | | | | | 155 | | | | | 160 |
| Glu | Ile | Gln | Val | Pro | Thr | Thr | Arg | Tyr | Leu | Gln | Ile | Ala | Leu | Leu | Ile |
| | | | | 165 | | | | | 170 | | | | | 175 | |
| Ser | Ser | Gln | Pro | Leu | Leu | Tyr | Val | Gly | Gly | Ala | Leu | Ala | Ala | Glu |
| | | | 180 | | | | | 185 | | | | | 190 | | |
| Leu | Leu | Ala | Glu | Phe | Ile | Pro | Val | Thr | Thr | Thr | Leu | Met | Gly | Lys | Gly |
| | | | 195 | | | | | 200 | | | | | 205 | | |
| Ala | Phe | Glu | Asn | Leu | Tyr | Leu | Gly | Met | Leu | Gly | Met | His | Gly | Thr | Gly |
| | 210 | | | | | 215 | | | | | 220 | | | | |
| Tyr | Ala | Asn | Phe | Ala | Val | Ser | Glu | Cys | Asp | Leu | Leu | Ile | Ala | Ile | Gly |
| 225 | | | | | 230 | | | | | 235 | | | | | 240 |
| Ala | Arg | Phe | Asp | Asp | Arg | Val | Thr | Gly | Lys | Leu | Glu | Asp | Phe | Ala | Ser |
| | | | | 245 | | | | | 250 | | | | | 255 | |
| Gln | Ala | Lys | Ile | Leu | His | Ile | Asp | Ile | Asp | Pro | Glu | Ile | Gly | Lys | Asn |
| | | | 260 | | | | | 265 | | | | | 270 | | |
| Lys | Ile | Pro | His | Leu | Ala | Ile | Ile | Gly | Asp | Ile | Lys | Val | Leu | Gln | Leu |
| | | 275 | | | | | 280 | | | | | 285 | | | |
| Leu | His | Thr | Pro | Leu | Tyr | Asp | Ala | Arg | Trp | Arg | Glu | Arg | Ile | Lys | Trp |
| | 290 | | | | | 295 | | | | | 300 | | | | |
| Lys | Arg | Tyr | Pro | Leu | Ile | Ile | Pro | Val | Gly | Leu | Ser | Pro | Gln | Ile | Ile |
| 305 | | | | | 310 | | | | | 315 | | | | | 320 |
| Asn | Arg | Leu | Ala | Glu | Leu | Leu | Pro | Ala | Tyr | Phe | Thr | Thr | Asp | Val | Gly |
| | | | | 325 | | | | | 330 | | | | | 335 | |
| Gln | His | Gln | Met | Trp | Ala | Ala | Gln | Phe | Leu | Lys | Arg | Lys | Trp | Met | Ser |
| | | | 340 | | | | | 345 | | | | | 350 | | |
| Ser | Ala | Gly | Leu | Gly | Thr | Met | Gly | Tyr | Gly | Leu | Pro | Ala | Ala | Ile | Gly |
| | | 355 | | | | | 360 | | | | | 365 | | | |
| Ala | Gln | Leu | Ala | Phe | Pro | Ser | Val | Val | Cys | Ile | Ser | Gly | Asp | Ala | Ser |

```
                    370                 375                 380
Phe Gln Met Asn Leu Gln Glu Leu Gly Thr Ile Ala Gln Tyr Asn Leu
385                 390                 395                 400

Pro Ile Lys Ile Leu Ile Leu Asn Asn Arg Trp Gln Gly Met Val Arg
                405                 410                 415

Gln Trp Gln Gln Ser Phe Tyr Asp Arg Tyr Ser His Ser Met Asp Gly
            420                 425                 430

Pro Asp Phe Val Lys Leu Ala Glu Ser Tyr Gly Ile Lys Gly Arg Ile
            435                 440                 445

Lys Thr Glu Glu Leu Ile Asn Asp Ile Val Thr Gly Pro Leu Leu Ile
        450                 455                 460

Asp Asp Val Glu Glu Asn Cys Tyr Pro Met Val Ala Pro Gly Lys Ser
465                 470                 475                 480

Asn Ser Gln Met Ile Gly Leu Glu Ser Thr Lys Lys
                485                 490

<210> SEQ ID NO 34
<211> LENGTH: 5
<212> TYPE: PRT
<213> ORGANISM: Artificial Sequence
<220> FEATURE:
<223> OTHER INFORMATION: Synthetic construct

<400> SEQUENCE: 34

Arg Phe Asp Asp Arg
1               5
```

COMPOSITIONS AND METHODS FOR MODULATING THE SENSITIVITY OF CELLS TO AHAS INHIBITORS

CROSS-REFERENCES TO RELATED APPLICATIONS

This application claims benefit of U.S. provisional patent application 61/639,727, filed Apr. 27, 2012, which is incorporated by reference in its entirety.

FIELD OF THE INVENTION

The present application is in the field of molecular biology and genetics. Specifically, the disclosure provides materials and methods useful for genetically engineering of cells and organisms. In particular, the disclosure provides compositions, methods and related materials useful for modulating the sensitivity of cells to chemical compounds that inhibit acetohydroxyacid synthase (AHAS) activity.

INCORPORATION OF SEQUENCE LISTING

The material in the accompanying Sequence Listing is hereby incorporated by reference into this application. The accompanying sequence listing text file, name SGI1570-1_Seq_Listing, was created on Apr. 26, 2013 and is 58 KB. The file can be assessed using Microsoft Word on a computer that uses Windows OS.

BACKGROUND OF THE INVENTION

Microalgal species of the genus *Nannochloropsis* have attracted considerable interest for various commercial applications. For example, several *Nannochloropsis* species are commonly cultivated in fish hatcheries as a food source for zooplankton production, such as rotifers and copepods, which in turn is used as feed for rearing larvae of many species of mollusks, crustaceans, and fish. Further, several *Nannochloropsis* species are well known as being capable to build up a high concentration of a range of different valuable pigments such as astaxanthin, canthaxanthin, chlorophyll a, and zeaxanthin. Additionally, many *Nannochloropsis* species are considered as promising microorganisms for industrial applications because of their ability to accumulate high levels of polyunsaturated fatty acids (PUFA), especially eicosapentaenoic acid (EPA). As a result, *Nannochloropsis* is often recognized as being potentially a good source for the dietary supplement of omega-3 fatty acids and other important PUFAs for human consumption for prevention of several diseases and medical conditions.

Moreover, *Nannochloropsis* has been increasingly considered to have good potentials as a bioreactor to carry or produce valuable heterologous protein because of the low production cost, high expression level, relatively simple culture conditions. More recently, *Nannochloropsis* has gained commercial importance as being potentially suitable for algal biofuel production, and thus has attracted considerable attention due to its relative ease of growth and high oil content (see, e.g., Radakovits et al., *Eukaryotic Cells,* 486-501, Vol. 9, No. 4, 2010). Nevertheless, optimization of culture conditions for selected *Nannochloropsis* species has been reported to be potentially a challenge, because the fatty acid content of individual species and isolates can vary considerably under different environmental conditions in the field and in laboratory culture. For example, cellular lipid content of some marine *Nannochloropsis* species has been reported to be highly affected by the availability of nitrogen sources in the growth medium. Also, the production of fatty acids in *Nannochloropsis* is often directly dependent on $CO_2$ concentration in aerated suspension cultures. Another potential challenge for the use of *Nannochloropsis* in industrial applications is that the accumulation of fatty acids including PUFA in *Nannochloropsis*, for example *Nannochloropsis limnetica*, has been reported to be highly dependent on growth phases; i.e. higher PUFA cellular content in the stationary phase of growth and even considerably higher in non-aerated cultures.

Therefore, there exists a continuing need to develop novel strains of *Nannochloropsis* that are more stable in different growth environments and thus more suitable to industrial production. When transgenic approaches are considered, there is an additional need in the art to develop new and useful tools and methods for the transformation of *Nannochloropsis* microorganisms, which in turn will facilitate the generation of novel strains with enhanced commercial value. Finally, there also exists an ongoing need to develop materials and methods for mutation or inactivation of specific genes by homologous recombination in *Nannochloropsis* microorganisms, providing a new way to alter cellular metabolism and to study the function of specific genes and biosynthetic pathways in *Nannochloropsis*.

The present application discloses materials and methods that may find uses in, for example, genetic engineering of cells and organisms. Particularly, the materials and methods disclosed herein can be used to confer the tolerance of recombinant cells to chemical inhibitors that inhibit acetohydroxyacid synthase activity such as, for example, herbicide compounds and therefore can be useful in, for example, controlling unwanted contaminant organisms that are sensitive to such herbicides.

SUMMARY OF THE INVENTION

Methods and materials useful for modulating the sensitivity of cells to an inhibitor of acetohydroxyacid synthase (AHAS) are disclosed. For example, nucleic acid molecules encoding AHAS large subunits and variants thereof with improved properties are disclosed as well as methods for using such nucleic acid molecules to transform microbial cells and plant cells, and to confer modulated sensitivity to AHAS-inhibiting compounds onto such cells. Further provided are materials and methods useful for modulating growth, development, activity, and characteristics of host cells and organisms.

In one aspect of the present invention, the disclosure provides isolated nucleic acid molecules that hybridize under high stringency conditions to a nucleotide sequence selected from the group consisting of SEQ ID NO: 2, SEQ ID NO: 4, and SEQ ID NO: 6; and complements of nucleotide sequences that hybridize under high stringency conditions to said sequences; and fragments of either. The disclosure also provides isolated nucleic acid molecules exhibiting 70% or greater or 80% or greater or 90% or greater or 95% or greater or 97% or greater or 98% or greater or 99% or greater sequence identity to a nucleotide sequence selected from the group consisting of SEQ ID NO: 2, SEQ ID NO: 4, and SEQ ID NO: 6 or complements of any of said sequences; and fragments of either. The disclosure further provides isolated nucleic acid molecules encoding polypeptides that exhibit 50% or greater or 70% or greater or 80% or greater or 90% or greater or 95% or greater or 97% or greater or 98% or greater or 99% or greater identity to an amino acid sequence selected from the group consisting of SEQ ID NO: 1, SEQ ID NO: 3, and SEQ ID NO: 5 in the Sequence Listing.

The disclosure further provides nucleotide sequences which are an interfering RNA to nucleic acid molecules that hybridize under high stringency conditions to a nucleotide sequence selected from the group consisting of SEQ ID NO: 2, SEQ ID NO: 4, and SEQ ID NO: 6; and nucleotide sequences that are interfering RNA to complements of nucleotide sequences that hybridize under high stringency conditions to said sequences; and fragments of either. The disclosure also provides nucleotide sequences that are interfering RNA to any one of the nucleic acids exhibiting 70% or greater or 80% or greater or 90% or greater or 95% or greater or 97% or greater or 98% or greater or 99% or greater sequence identity to a nucleotide sequence selected from the group consisting of SEQ ID NO: 2, SEQ ID NO: 4, and SEQ ID NO: 6 or interfering RNA to complements of any of said sequences; and interfering RNA to fragments of either. The disclosure further provides nucleotide sequences that are interfering RNA to nucleic acid molecules encoding polypeptides that exhibit 50% or greater or 70% or greater or 80% or greater or 90% or greater or 95% or greater or 97% or greater or 98% or greater or 99% or greater identity to an amino acid sequence selected from the group consisting of SEQ ID NO: 1, SEQ ID NO: 3, and SEQ ID NO: 5 in the Sequence Listing.

In some preferred embodiments of this aspect, the nucleic acid molecules disclosed herein encode an acetohydroxyacid synthase. In some other preferred embodiments, such nucleic acid molecules encode a *Nannochloropsis* acetohydroxyacid synthase. In yet other preferred embodiments, such nucleic acid molecules encode an acetohydroxyacid synthase having a reduced sensitivity to an AHAS inhibitor. In some particularly preferred embodiments, the AHAS inhibitor may be selected from the group consisting of imidazolinone-class inhibitors, pyrimidyloxybenzoates, sulfonylurea compounds, sulfonlyaminocarbonyl-triazolinones, and triazolopyrimidines.

In some embodiments of this aspect, the nucleic acid molecules disclosed herein encode polypeptides having an amino acid sequence that differs from any one of the polypeptides in the Sequence Listing by at least one amino acid substitution at a position corresponding to an amino acid residue selected from the group consisting of the amino acid residues identified in Table 1 and FIG. 1 as conserved residues, and combinations of any thereof. In some preferred embodiments, such nucleic acid molecules encode polypeptides having an amino acid sequence that differs from a polypeptide selected from the group consisting of SEQ ID NO: 1, SEQ ID NO: 3, and SEQ ID NO: 5, by at least one amino acid substitution at a position corresponding to an amino acid residue selected from the group consisting of the amino acid residues identified in Table 1 and FIG. 1 as conserved residues, and combinations of any thereof, of the corresponding polypeptide. In some particularly preferred embodiments of this aspect, the at least one amino acid substitution at a position corresponding to an amino acid residue is selected from the group consisting of R9, G35, A36, L38, I56, G114, A116, A122, I171, K173, I186, N194, A234, M272, D296, D297, P319, K337, S348, P352, F361, E364, V367, V491, W494, F498, D500, P567, G568, and combinations of any thereof, of SEQ ID NO: 1.

In another aspect of the present invention, the disclosure further provides isolated polypeptides. In some embodiments, such isolated polypeptides are encoded by nucleic acid molecules including nucleic acid sequences which hybridize under high stringency conditions to a nucleotide sequence selected from the group consisting of SEQ ID NO: 2, SEQ ID NO: 4, and SEQ ID NO: 6; complements of nucleotide sequences that hybridize under high stringency conditions to a nucleotide sequence selected from the group consisting of SEQ ID NO: 2, SEQ ID NO: 4, and SEQ ID NO: 6; or fragments of either.

The disclosure also provides isolated polypeptides that are encoded by nucleic acid molecules having a sequence identity of 70% or greater or 80% or greater or 90% or greater or 95% or greater or 97% or greater or 98% or greater or 99% or greater identity to a nucleotide sequence selected from the group consisting of SEQ ID NO: 2, SEQ ID NO: 4, and SEQ ID NO: 6 or complements thereof or fragments of any.

The disclosure further provides isolated polypeptides that are encoded by nucleotide sequences encoding an amino acid sequence that exhibits 50% or greater identity to an amino acid sequence selected from the group consisting of SEQ ID NO: 1, SEQ ID NO: 3, and SEQ ID NO: 5 in the Sequence Listing.

In another aspect, the disclosure also provides recombinant nucleic acid constructs, such as recombinant nucleic acid vectors, which include a polynucleotide of the invention that is operably linked to a heterologous nucleic acid. Particularly, in some embodiments of this aspect, the disclosure provides recombinant nucleic acid constructs that include a heterologous promoter operably linked to a nucleic acid molecule comprising a nucleic acid sequence selected from the group consisting of SEQ ID NO: 2, SEQ ID NO: 4, and SEQ ID NO: 6; a nucleic acid sequence hybridizing under high stringency conditions to a nucleic acid sequence selected from the group consisting of SEQ ID NO: 2, SEQ ID NO: 4, and SEQ ID NO: 6; a complement thereof or a fragment of either; a nucleic acid sequence exhibiting 70% or greater sequence identity to a nucleic acid sequence selected from the group consisting of SEQ ID NO: 2, SEQ ID NO: 4, and SEQ ID NO: 6; a complement thereof or a fragment of either; or a nucleic acid sequence encoding a polypeptide that exhibits 50% or greater sequence identity to an amino acid sequence selected from the group consisting of SEQ ID NO: 1, SEQ ID NO: 3, and SEQ NO: 5 in the Sequence Listing. In some preferred embodiments of this aspect, the recombinant nucleic acid constructs of the present invention further include a heterologous nucleic acid encoding a transit peptide, such as a chloroplast transit peptide.

Such recombinant vector constructs are useful for, for example, transformation and expression of the polynucleotides and polypeptides in transgenic cells and transgenic organisms that include but are not limited to transgenic plants and transgenic microorganisms.

In yet another aspect of the present invention, the disclosure further provides a host cell that includes a nucleic acid molecule described herein. In some embodiments the nucleic acid molecule is selected from the group consisting of SEQ ID NO: 2, SEQ ID NO: 4, and SEQ ID NO: 6; a nucleic acid sequence hybridizing under high stringency conditions to a nucleotide sequence selected from the group consisting of SEQ ID NO: 2, SEQ ID NO: 4, and SEQ ID NO: 6, a complement thereof or a fragment of either; a nucleic acid sequence exhibiting 70% or greater or 80% or greater or 90% or greater or 95% or greater or 97% or greater or 98% or greater or 99% or greater sequence identity to a nucleotide sequence selected from the group consisting of SEQ ID NO: 2, SEQ ID NO: 4, and SEQ ID NO: 6; a complement thereof or a fragment of either; or a nucleic acid sequence encoding a polypeptide that exhibits 50% or greater or 70% or greater or 80% or greater or 90% or greater or 95% or greater or 97% or greater or 98% or greater or 99% or greater sequence identity to an amino acid sequence selected from the group consisting of SEQ ID NO: 1, SEQ ID NO: 3, and SEQ ID NO: 5 in the Sequence Listing. The inventive nucleic acid molecule according to this aspect is operably linked to a heterologous nucleic acid molecule. In some preferred embodiments of this aspect, the host cell may be an algal cell, a bacterial cell, a fungal cell, or a plant cell. In a more preferred embodiments, the host cell is an algal cell. In a particularly preferred embodiment, the host cell is a *Nannochloropsis* cell. In certain embodiments of this aspect, the nucleic acid molecule may be integrated into the genome of the host cell via homologous recombination or ectopic insertion. In some other embodiments, the nucleic acid molecule may be integrated into a chloroplast genome or nuclear genome of the host cell. In some other embodiments, the host cell may be an algal cell, a bacterial cell, a fungal cell, or a plant cell. In yet some other embodiments, the host cell may be a *Nannochloropsis* cell. In yet other embodiments, the host cell according to this aspect of the invention may further include a second heterologous nucleic acid sequence to be expressed by the host cell.

Further provided are host organisms containing a host cell that includes a nucleic acid molecule comprising a nucleic acid sequence selected from the group consisting of SEQ ID NO: 2, SEQ ID NO: 4, and SEQ ID NO: 6; a nucleic acid sequence hybridizing under high stringency conditions to a nucleic acid sequence selected from the group consisting of SEQ ID NO: 2, SEQ ID NO: 4, and SEQ ID NO: 6; a complement thereof or a fragment of either; a nucleic acid sequence exhibiting 70% or greater sequence identity to a nucleic acid sequence selected from the group consisting of SEQ ID NO: 2, SEQ ID NO: 4, and SEQ ID NO: 6; a complement thereof or a fragment of either; or a nucleic acid sequence encoding a polypeptide that exhibits 50% or greater sequence identity to an amino acid sequence selected from the group consisting of SEQ ID NO: 1, SEQ ID NO: 3, and SEQ ID NO: 5 in the Sequence Listing. The nucleic acid molecule is operably linked to a heterologous nucleic acid molecule. In some preferred embodiments, such host organism may be an alga, a bacterium, a fungus, or a plant. In some other embodiments, the disclosure also provides the biological samples, biomass, and progeny derived from a host organism as described above. In yet other embodiments, the disclosure also provides compositions comprising biomaterial derived from a host organism as described above. The compositions may be food, feed, biofuel, cosmetic, medicinal, neutraceutical, nutritional, or pharmaceutical products that comprise biomaterial derived from a host organism as described above.

Another aspect of the present invention provides a method for modulating sensitivity of a cell to an AHAS inhibitor. The method involves introducing into a cell a nucleic acid molecule that confers a modulated sensitivity of the cell to an AHAS inhibitor as compared to a control cell. The nucleic acid molecule comprises a nucleic acid sequence selected from the group consisting of SEQ ID NO: 2, SEQ ID NO: 4, and SEQ ID NO: 6; a nucleic acid sequence hybridizing under high stringency conditions to a nucleic acid sequence selected from the group consisting of SEQ ID NO: 2, SEQ ID NO: 4, and SEQ ID NO: 6; a complement thereof or a fragment of either; a nucleic acid sequence exhibiting 70% or greater sequence identity to a nucleic acid sequence selected from the group consisting of SEQ ID NO: 2, SEQ ID NO: 4, and SEQ ID NO: 6; a complement thereof or a fragment of either; or a nucleic acid sequence encoding a polypeptide that exhibits 50% or greater sequence identity to an amino acid sequence selected from the group consisting of SEQ ID NO: 1, SEQ ID NO: 3, and SEQ ID NO: 5 in the Sequence Listing.

Implementations of the inventive method described above may include one or more of the following features. The method may further include a step of selecting cells that have been successfully transformed with a nucleic acid molecule of the present invention by culturing the cells in a growth medium containing at least one AHAS inhibitor that is inhibitory to the growth of untransformed cells. In some preferred embodiments, the at least one AHAS inhibitor that inhibits the growth of untransformed cells may be selected from the group consisting of imidazolinone-class inhibitors, pyrimidyloxybenzoates, pyrimidinylsalicylates, sulfonylurea compounds, sulfonlyaminocarbonyl-triazolinones, and triazolopyrimidines. A step of regenerating from the transformed cell a transformed organism may be included. The nucleic acid molecule may be integrated into the genome of the host cell via homologous recombination or ectopic insertion. The nucleic acid molecule may be integrated into a chloroplast genome or nuclear genome of the host cell. The host cell may be an algal cell, a bacterial cell, a fungal cell, or a plant cell. The host cell may be a *Nannochloropsis* cell.

In some further embodiments of this aspect, nucleic acid molecules that are introduced into the host cell may include a second heterologous nucleic acid sequence to be expressed by the host cell. In some preferred embodiments, the heterologous second nucleic acid sequence is operably linked to a second promoter sequence. In some other embodiments, the second heterologous nucleic acid sequence is transcribed and results in a modulation of the growth, development, activity, or characteristics of the host cell. The growth, development, activity, or characteristics of the host cell may include any one of the followings: amino acid content, carbohydrate content, fatty acid/oil content, the saturated fatty acid synthesis pathways, the polyunsaturated fatty acid synthesis pathways, the isoprenoid pathways, the activity of a polyketide synthase complex, the incorporation of fatty acids into phospholipids or triacylglycerol molecules, the carbohydrate and starch biosynthesis pathways, the synthesis of cell wall components, photosynthesis capacity, and the production of pigments. In some other embodiments, the second heterologous nucleic acid sequence is involved in the production of a vaccine.

These and other objects and features of the invention will become more fully apparent from the following detailed description of the invention and the claims

BRIEF DESCRIPTION OF THE DRAWINGS

Figure 1:
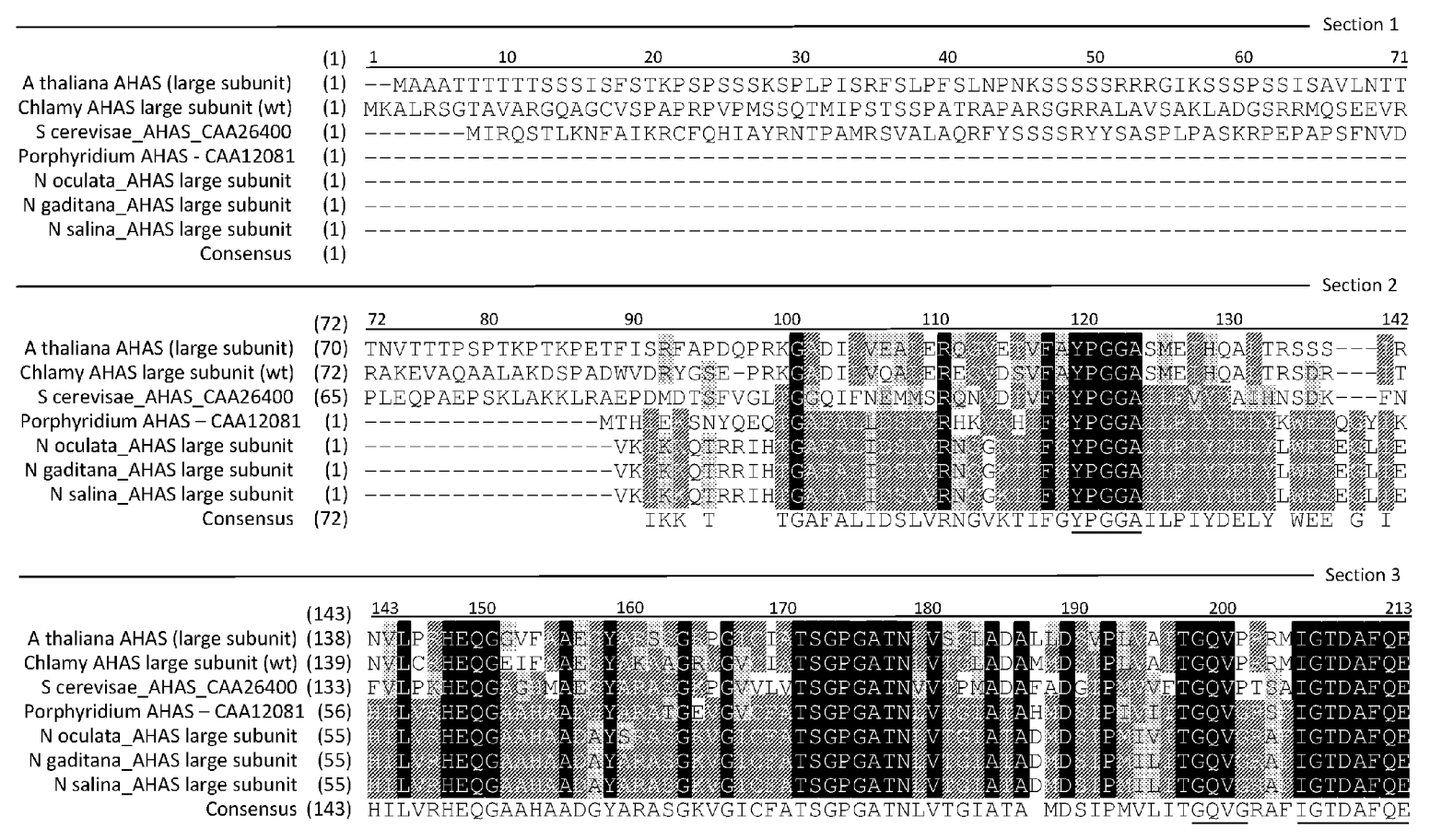
Figure 1:
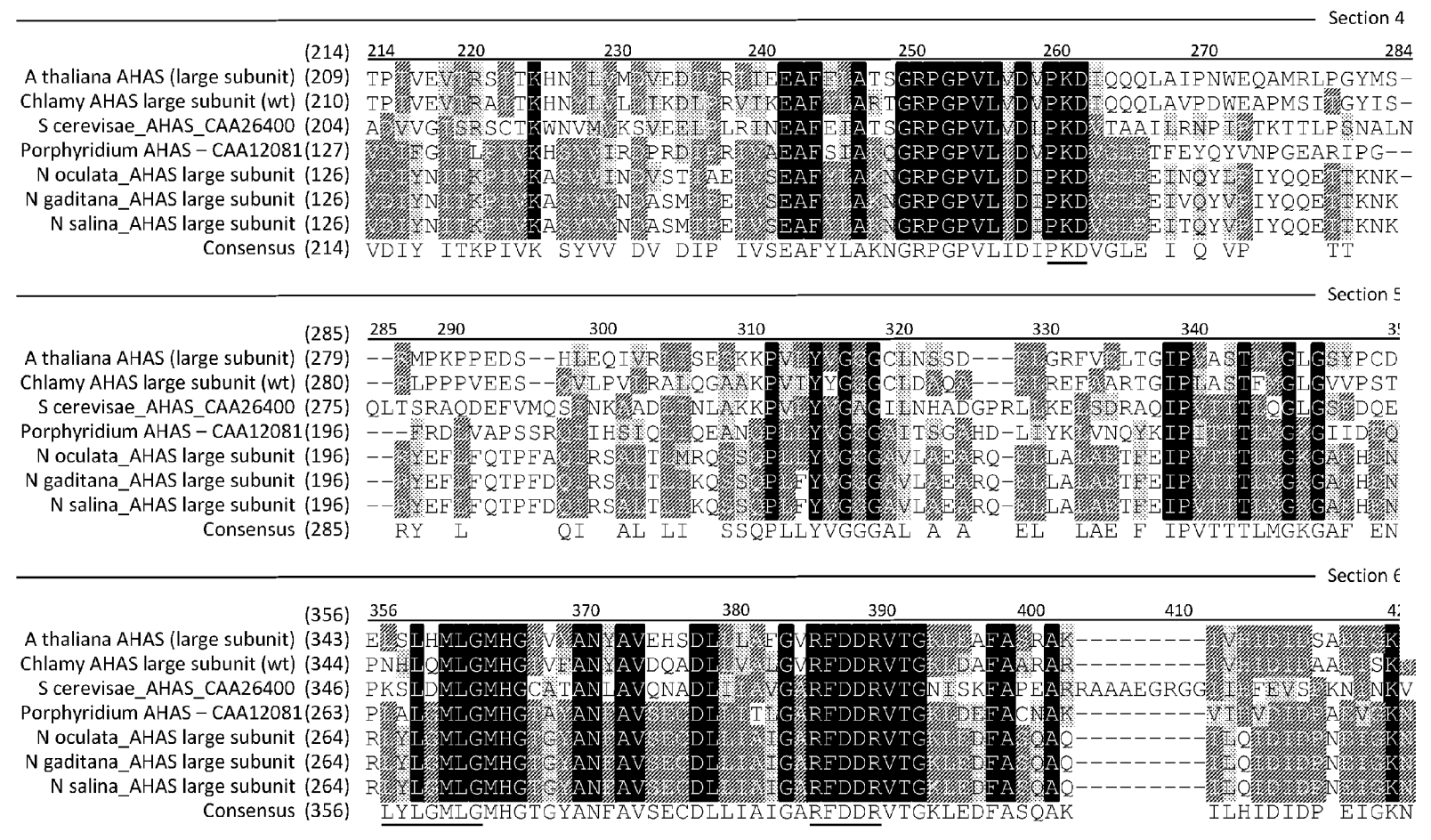
Figure 1:
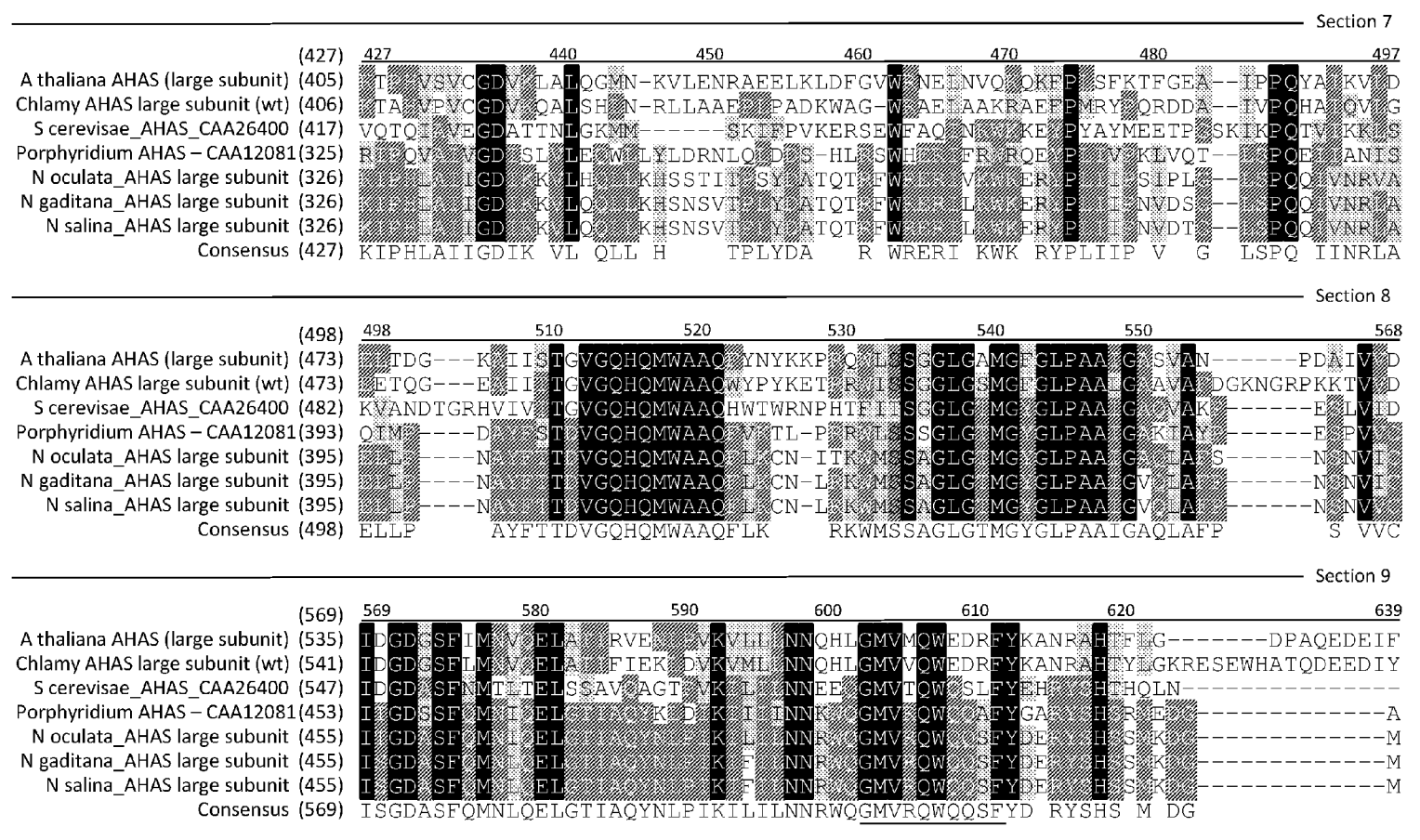
Figure 1:
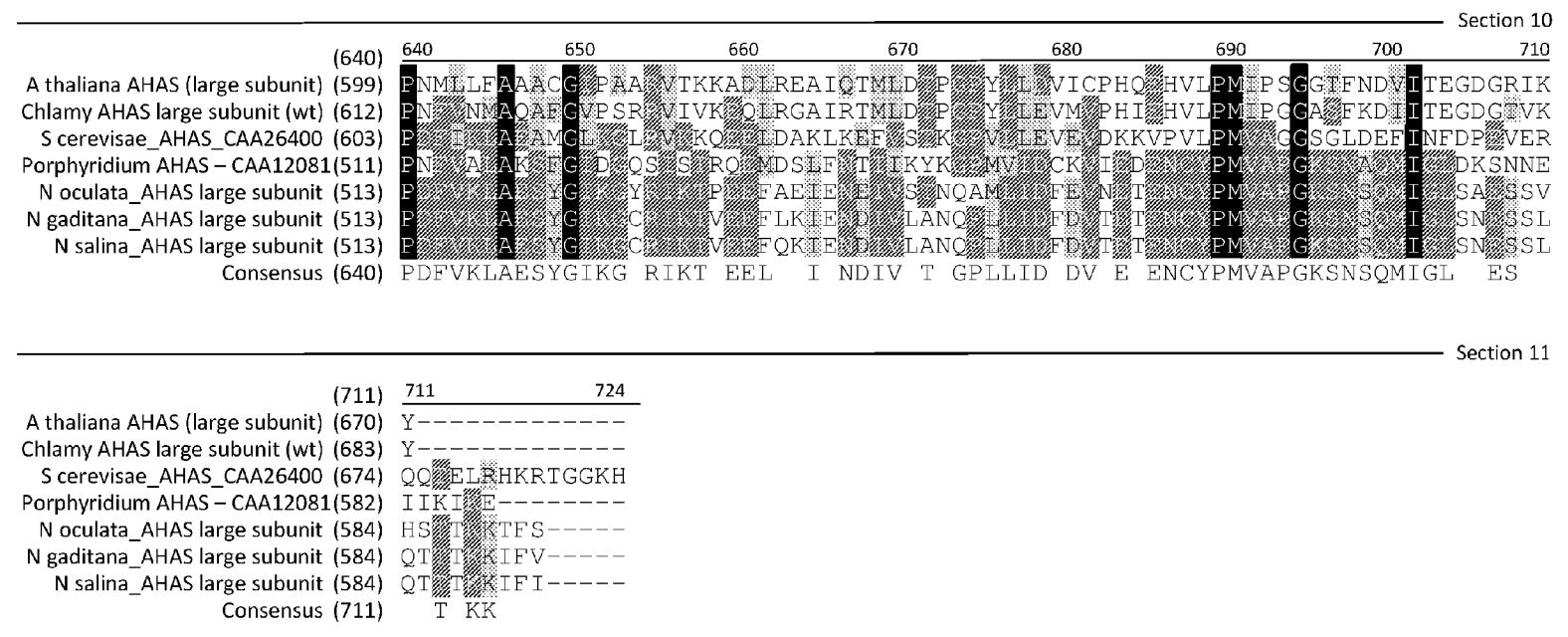

FIG. 1 is an alignment of the *Nannochloropsis gaditana* AHAS large subunit (SGI protein ID Ng110602, SEQ ID NO: 1), *Nannochloropsis oculata* AHAS large subunit (SGI protein ID No110817, SEQ ID NO: 3), *Nannochloropsis salina* AHAS large subunit (SGI protein ID Ns110809, SEQ ID NO: 5), with homologous sequences from *Arabidopsis thaliana* (SEQ ID NO: 8), *Chlamydomonas reinhardtii* (SEQ ID NO: 10), *Porphyridium* sp. (SEQ ID NO: 7), and budding yeast *Saccharomyces cerevisiae* (SEQ ID NO: 9). The sequence alignment of FIG. 1 was generated using the program AlignX of the Vector NTI Advance™ 11.5 package (Invitrogen, Carlsbad, Calif.) with default settings. As discussed in detail elsewhere herein, several polypeptide domains and motifs with high degree of conservation have been identified from this sequence comparison analysis. In the alignment figure shown herein, a dash in an aligned sequence represents a gap, i.e., a lack of an amino acid at that position. Black boxes and gray boxes identify identical amino acids and conserved amino acids, respectively, among aligned sequences. Underscored motifs of the consensus sequence (SEQ ID NO:33) in the alignment of FIG. 1 indicate the conserved residues and motifs corresponding to the "substantially conserved sub-sequences" described in U.S. Pat. No. 5,605,011. In addition, amino acid residues corresponding to the "substantially conserved sub-sequences" of each of the AHAS polypeptides disclosed herein are also indicated in the Sequence Listing. The identical residues, conversed residues, conserved motifs, and "substantially conserved sub-sequences", identified as such in this alignment, constitute non-limiting exemplifications of conserved amino acid residues and features in the sequences of AHAS polypeptides from different organisms.

DETAILED DESCRIPTION OF THE INVENTION

This application relates to compositions, methods and related materials to genetically transform organisms. Some preferred embodiments specifically relates to compositions, methods and related materials to genetically transform plants and microorganisms of the genus *Nannochloropsis*.

In one aspect, the present invention provides methods and materials that can be used to modulate the sensitivity of cells to AHAS-inhibiting compounds. For example, nucleic acid molecules that encode acetohydroxyacid synthase (AHAS) large subunits are disclosed as well as methods for using such nucleic acids to transform cells, including plant cells and microbial cells, and to confer modulated sensitivity to AHAS-inhibiting compounds onto said cells. The present disclosure also provides transgenic cells and transgenic organisms comprising such nucleic acid molecules, and methods for making and using the same. Particularly, transgenic cells produced using the methods and materials of the invention may be grown to produce novel organisms having reduced sensitivity to AHAS-inhibitors. Such organisms can include herbicide tolerant varieties of crop plants and herbicide-tolerant strains of microorganisms, for example, microalgae.

Particularly, the compositions and methods described herein can be used to introduce heterologous sequences into microorganisms of the genus *Nannochloropsis*, thereby providing a means to create algal strains with enhanced commercial value. In addition, the compositions and methods disclosed herein can be used to enable the mutation or inactivation of specific genes by homologous recombination, providing a new way to alter cellular metabolism and to identify the functions of specific sequences in *Nannochloropsis* microorganisms.

Additionally, microbial cells and plant cells produced using a method in accordance with the present disclosure may be used to produce biomass, microbial products, plant products, e.g., food, feed, biofuel, cosmetic, medicinal, nutraceutical, nutritional, or pharmaceutical products.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, including mixtures thereof.

Amino acid: As used herein, "amino acid" refers to naturally-occurring and synthetic amino acids, as well as amino acid analogs and amino acid mimetics that function in a manner similar to the naturally-occurring amino acids. Naturally-occurring amino acids are those encoded by the genetic code, including D/L optical isomers, as well as those amino acids that are later modified, e.g., hydroxyproline, y-carboxyglutamate, and O-phosphoserine. Amino acid analogs refer to compounds that have the same basic chemical structure as a naturally-occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics, as used herein, refer to chemical compounds that have a structure that is different from the general chemical structure of an amino acid, but that functions in a manner similar to a naturally-occurring amino acid.

Biofuel: "Biofuels", as used herein, refer to renewable energy sources from living organisms, such as higher plants, fungi, algae, or microorganisms. As such, biofuels can be solid, liquid or gaseous fuels derived from algal, fungal, microbial or plant materials, biomass, sugars or starches, such as ethanol or biodiesel derived from vegetable oils or algal oil, and the like. A biofuel is a fuel in its own right, but may be blended with petroleum-based fuels to generate a finished fuel. A biofuel may be used as a replacement for petrochemically-derived gasoline, diesel fuel, or jet fuel.

Down-regulation: "Down-regulation" refers to regulation that decreases production of expression products (mRNA, polypeptide, biological activity, or combinations of any thereof) relative to basal or native states.

Endogenous: The term "endogenous," within the context of the present disclosure refers to any polynucleotide, polypeptide or protein sequence which is a natural part of a cell or organism regenerated from said cell.

Exogenous: "Exogenous" with respect to a nucleic acid indicates that the nucleic acid is part of a recombinant nucleic acid construct and is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally-occurring sequence by the presence of non-natural sequences linked to the exogenous nucleic acid, e.g., non-native regulatory sequences flanking a native sequence in a recombinant nucleic acid construct. In addition, stably transformed exogenous nucleic acids can be integrated at positions other than the position where the native sequence is found. It will be appreciated that an exogenous nucleic acid may have been introduced into a progenitor, and not into the cell under consideration. For example, a transgenic plant containing an exogenous nucleic acid can be the progeny of a cross between a stably transformed plant and a non-transgenic plant. Such progeny are considered to contain the exogenous nucleic acid.

Expression: As used herein, "expression" refers to the process of converting genetic information of a polynucleotide into RNA through transcription, which is typically catalyzed by an enzyme, RNA polymerase, and into protein, through translation of mRNA on ribosomes.

Functional homolog: The term "functional homolog" as used herein describes those molecules that have at least one characteristic in common. Such characteristics include sequence similarity, biochemical activity, transcriptional pattern similarity and phenotypic activity. Typically, a functional homolog is a polypeptide that has sequence similarity to a reference polypeptide, and that carries out one or more of the biochemical or physiological function(s) of the reference polypeptide. Functional homologs will typically give rise to the same characteristics to a similar, but not necessarily the same, degree. Functionally homologous proteins give the same characteristics where the quantitative measurement produced by the homolog is 50% or greater or 70% or greater or 80% or greater or 90% or greater or 95% or greater or 97% or greater or 98% or greater or 99% or greater compared to the original molecule. Thus, where the molecule has enzymatic activity the functional homolog will have the above-recited percent enzymatic activities compared to the original enzyme. Where the molecule is a binding molecule (e.g., a polypeptide) the homolog will have the above-recited percentage of binding affinity as measured by weight of bound molecule compared to the original molecule. Where the molecule is a nucleic acid the functional homolog will have the above-recited percentage of sequence identity to the original molecule, calculated as described herein.

A functional homolog and the reference polypeptide may be naturally occurring polypeptides, and the sequence similarity may be due to convergent or divergent evolutionary events. As such, functional homologs are sometimes designated in the literature as homologs, orthologs, or paralogs. Variants of a naturally-occurring functional homolog, such as polypeptides encoded by mutants or a wild-type coding sequence, may themselves be functional homologs. As used herein, functional homologs can also be created via site-directed mutagenesis of the coding sequence for an AHAS polypeptide, or by combining domains from the coding sequences for different naturally-occurring AHAS polypeptides. The term "functional homolog" sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of AHAS polypeptides. Sequence analysis can involve BLAST, Reciprocal BLAST, or PSI-BLAST analysis of non-redundant databases using amino acid sequence of an AHAS polypeptide as the reference sequence. Amino acid sequence is, in some instances, deduced from the nucleotide sequence. Typically, those polypeptides in the database that have greater than 40% sequence identity are candidates for further evaluation for suitability as an AHAS polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in AHAS polypeptides, e.g., conserved functional domains.

"Herbicide resistance" or "herbicide tolerance", as used herein, refers to a capability of an organism or cell to grow in the presence of selective concentrations of an herbicide. The term "selective concentration" refers to a concentration of an inhibitor or antibiotic compound, for example, an herbicide, which is capable of inhibiting the metabolism, growth, or multiplication of a wild-type cell or organism. Such an organism, as well as clones thereof, is referred to as a "sensitive" organism or cell. In relation to particular enzymes or proteins, "sensitive" indicates that the enzyme or protein is susceptible to specific inhibition by a particular inhibiting compound, for example, an antibiotic or herbicide. In relation to particular enzymes or proteins, "resistant" indicates that the enzyme or protein, as a result of a different chemical structure, expresses activity in the presence of a selective concentration of a specific inhibitor which inactivates sensitive variants of the enzyme or protein.

As used herein unless otherwise indicated, "herbicide resistance" is inheritable and allows a cell or an organism to grow and reproduce in the presence of an effective treatment of an herbicide. As is recognized by those skilled in the art, a microbial strain or a plant cultivar may still be considered "resistant" even though some degree of cell or plant injury from herbicidal exposure is apparent. As used herein, the term "tolerance" is broader than the term "resistance", and includes "resistance" as defined herein, as well as an improved capacity of a particular organism to withstand the various degrees of herbicidally induced injury that typically result in wild-type organism of the same genetic background at the same herbicidal dose. In some embodiments "herbicide resistant" refers to an organism (e.g., a cell or population of cells) that can grow and reproduce in an amount of herbicide that would prevent sustained reproductive growth in at least 10% of reference or wild type organisms.

The term "resistance" or "tolerance", when used in conjunction with genetic modification or recombinant organisms also means that the resistance or tolerance is conferred by a heterologous nucleic acid sequence encoding an enzyme that is resistant to deactivation by an AHAS-inhibiting compound or tolerant to an AHAS-inhibiting compound at a concentration which would normally inhibit the activity of an unaltered enzyme. Resistance in this context typically includes resistance of an organism to multiple inhibitors having the same target site due to the presence of a predominantly single resistance mechanism.

Heterologous polypeptides and heterologous sequences: "Heterologous polypeptide" as used herein refers to a polypeptide that is not a naturally-occurring polypeptide in a host cell, e.g., a transgenic *Nannochloropsis* microorganism transformed with and expressing the coding sequence for a fatty acid transporter from a *Schizochytrium* microorganism or from a plant. "Heterologous sequences", as used herein, are those that are not operably linked or are not contiguous to each other in nature. For example, a promoter from *Schizochytrium* sp. is considered heterologous to a *Nannochloropsis* coding region sequence. Also, a promoter from a gene encoding an AHAS from *Nannochloropsis* is considered heterologous to a sequence encoding a *Nannochloropsis* sugar transporter. Regulatory element sequences, such as untranslated regions (UTRs) or 3' end termination sequences that do not originate in nature from the same gene as the coding sequence, are considered heterologous to said coding sequence. As such, elements operably linked in nature and contiguous to each other are not heterologous to each other. On the other hand, these same elements remain operably linked but become heterologous if other filler sequence is placed between them. Thus, the promoter and coding sequences of a *Nannochloropsis* gene expressing an amino acid transporter are not heterologous to each other, but the promoter and coding sequence of a *Nannochloropsis* gene operably linked in a novel manner are heterologous.

Isolated molecule and substantially purified molecule: As used herein, an "isolated" nucleic acid molecule or protein, or biologically active portion thereof, is greater than 90% or greater than 95% or greater than 98% or greater than 99% free from other molecules either by weight or by molar ratios. A substantially purified molecule is greater than 60% free, or greater than 75% free, or greater than 80% free, or greater than 85% free from the other molecules (exclusive of solvent) present in the natural mixture either by weight or by molar ratios. The term "substantially purified" is not intended to encompass molecules present in their native state. Thus, an "isolated" nucleic acid preferably is free of sequences that naturally flank the nucleic acid (i.e., sequences located at the 5' and 3' ends of the nucleic acid) in the cell of the organism from which the nucleic acid is derived. Thus, an isolated nucleic acid includes, without limitation, a nucleic acid that exists as a purified molecule [or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid. For purposes of the invention, the term "isolated" when used to refer to nucleic acid molecules also excludes isolated chromosomes. For example, in various embodiments of the present invention, an isolated AHAS-encoding nucleic acid molecule can contain small amounts of nucleotide sequences that naturally flank the nucleic acid molecule in the cell from which is it derived as long as it remains at least 90% free from other molecules either by weight or by molar ratio; thus for example an isolated AHAS-encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in the cell from which the nucleic acid is derived.

Mis-expression: The term "mis-expression" refers to an increase or decrease in the transcription of a coding region into a complementary RNA sequence as compared to the parental wild-type, for example, plant or microorganism. This term also encompasses expression of a gene or coding region for a different time period as compared to the wild-type and/or from a non-natural location within the parental genome.

Operably linked: As used herein, "operably linked" is intended to mean a functional linkage between two or more sequences such that activity at or on one sequence affects activity at or on the other sequence(s). For example, an operable linkage between a polynucleotide of interest and a regulatory sequence (e.g., a promoter) is a functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site. Operably linked elements may be contiguous or non-contiguous. When used to refer to the joining of two protein coding regions, by "operably linked" is intended that the coding regions are in the same reading frame. When used to refer to the effect of an enhancer, "operably linked" indicated that the enhancer increases the expression of a particular polypeptide or polynucleotides of interest. Where the polynucleotide or polynucleotides of interest encode a polypeptide, the encoded polypeptide is produced at an elevated level.

Percentage of percent identity: "Percentage of sequence identity," as used herein, is determined by comparing two optimally locally aligned sequences over a comparison window defined by the length of the local alignment between the two sequences. The amino acid sequence in the comparison window may comprise additions or deletions (e.g., gaps or overhangs) as compared to the reference sequence (which does not comprise additions or deletions) for optimal alignment of the two sequences. Local alignment between two sequences only includes segments of each sequence that are deemed to be sufficiently similar according to a criterion that depends on the algorithm used to perform the alignment (e.g. BLAST). The percentage identity is calculated by determining the number of positions at which the identical nucleic acid base or amino acid residue occurs in both sequences to yield the number of matched positions, dividing the number of matched positions by the total number of positions in the window of comparison and multiplying the result by 100. Optimal alignment of sequences for comparison may be conducted by the local homology algorithm of Smith and Waterman (*Add. APL. Math.* 2:482, 1981), by the global homology alignment algorithm of Needleman and Wunsch (*J. Mol. Biol.* 48:443, 1970), by the search for similarity method of Pearson and Lipman (*Proc. Natl. Acad. Sci. USA* 85: 2444, 1988), by heuristic implementations of these algorithms (NCBI BLAST, WU-BLAST, BLAT, SIM, BLASTZ), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 50% sequence identity, preferably at least 70%, preferably at least 80%, more preferably at least 85%, more preferably at least 90%, even more preferably at least 95%, and most preferably at least 96%, 97%, 98% or 99% sequence identity compared to a reference sequence using the programs. In addition, pairwise sequence homology or sequence similarity, as used refers to the percentage of residues that are similar between two sequences aligned. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Query nucleic acid and amino acid sequences were searched against subject nucleic acid or amino acid sequences residing in public or proprietary databases. Such searches were done using the National Center for Biotechnology Information Basic Local Alignment Search Tool (NCBI BLAST v 2.18) program. The NCBI BLAST program is available on the internet from the National Center for Biotechnology Information (blast.ncbi.nlm.nih.gov/Blast.cgi). Typically the following parameters for NCBI BLAST were used: Filter options were set to "default", the Comparison Matrix was set to "BLOSUM62", the Gap Costs were set to "Existence: 11, Extension: 1", the Word Size was set to 3, the Expect (E threshold) was set to 1e-3, and the minimum length of the local alignment was set to 50% of the query sequence length. Sequence identity and similarity may also be determined using GENOM-EQUEST™ software (Gene-IT, Worcester, Mass. USA).

Promoter: A "promoter" refers to a transcription control sequence that is capable of initiating transcription in a host cell and can drive or facilitate transcription of a nucleotide sequence or fragment thereof of the instant invention. Such promoters need not be of naturally-occurring sequences. In addition, it will be understood that such promoters need not be derived from the target host cell or host organism.

Polypeptide (also peptide, protein): "Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition. As used herein, the expression "substantially conserved amino acid sequences" refers to regions of amino acid homology between polypeptides comprising AHAS enzymes from different sources. In the present invention, examples of substantially conserved amino acid sequences include those specified in FIG. 1. One skilled in the art could align the amino acid sequences of AHAS enzymes from different sources to the schematic of FIG. 1 to identify the segments therein which are the substantially conserved amino acid sequences defined herein. The skilled person could then determine whether the identified segments have the characteristics disclosed and claimed in the present invention. It is to be understood that the expression "substantially conserved amino acid sequences" includes the segments which do not adversely affect the activity of the AHAS enzyme. In various embodiments the polypeptides can have at least 10 amino acids or at least 25, or at least 50 or at least 75 or at least 100 or at least 125 or at least 150 or at least 175 or at least 200 amino acids.

Progeny: As used herein, "progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

Regulatory region: The term "regulatory region", as used in the present invention, refers to a nucleotide sequence that influences transcription or translation initiation and rate, and stability and/or mobility of a transcription or translation product. Such regulatory regions need not be of naturally-occurring sequences. Regulatory sequences include but are not limited to promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene.

The term "selectable genetic marker", or its abbreviated form "selectable marker", refers to a nucleotide sequence which, when incorporated into one or more cells of an organism, allows differentiating that organism and its progeny from organisms lacking the selectable genetic marker. Non-limiting exemplifications of selectable genetic markers include those, when incorporated into the genome of an organism, allow growth of that organism and its progeny under conditions which inhibit growth of the organism lacking the selectable genetic markers. For example, a gene which encodes an enzyme that is resistant to specific inhibition by a particular antibiotic compound, such as an herbicide, can function as a selectable genetic marker by allowing an organism, such as a plant or an alga, to grow and propagate in the presence of a selective concentration of the compound. A second nucleic acid fragment, controlling a property which is difficult to assay, can be covalently linked to the selectable genetic marker, in which case the presence of the selectable marker, indicated by growth of an organism under selective conditions, can be used to detect an organism containing the second nucleic acid fragment.

Transgenic organism: As used herein, "transgenic organism" refers to an organism which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. When referring to a plant, "transgenic" is used herein to include any cell, cell line, callus, tissue, plant part or plant, the genotype of which has been altered by the presence of heterologous nucleic acid. The term "transgenic" includes those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally-occurring events such as random cross-fertilization, non-recombinant viral infection, non-recombinant bacterial transformation, non-recombinant transposition, or spontaneous mutation.

"Transit peptide" refers to a sequence of amino acids (typically a specific N-terminal sequence of amino acids) of a precursor protein (i.e., a pre-protein or precursor polypeptide) where the sequence is also referred to as a signal peptide, signal sequence, leader peptide, and where the sequence of amino acids is important for the translocation of a protein from its site of synthesis into, or through, a selected site within the cell. During translocation, the transit peptide can be excised from the remainder of the polypeptide precursor to provide an active or mature protein. Transit peptides are well known in the art and direct proteins to locations such as chloroplast, the mitochondria, the endoplasmic reticulum, the tonoplast, and the Golgi network, etc.

Untranslated region (UTR): A "UTR" refers to any contiguous series of nucleotide bases that is transcribed, but is not translated. These untranslated regions may be associated with particular functions such as increasing mRNA message stability. Examples of UTRs include but are not limited to polyadenylation signals, termination sequences, sequences located between the transcriptional start site and the first exon (i.e., leader or 5'-UTR), and sequences located between the last exon and the end of the mRNA (3'-UTR).

Variant: For nucleic acids and polypeptides, the term "variant" is used herein to denote a polypeptide, protein, or polynucleotide molecule with some differences, generated synthetically or naturally, in their base or amino acid sequences as compared to a reference polypeptide or polynucleotide, respectively, such that the variant has at least 70% sequence identity with the reference polypeptide or polynucleotide. In other embodiments the variant can have at least 80% or at least 90% or at least 95% or at least 97% or at least 98% or at least 99% sequence identity with the reference polypeptide or polynucleotide. For example, these differences include substitutions, insertions, deletions or any desired combinations of such changes in a reference polypeptide or polypeptide. Polypeptide and protein variants can further consist of changes in charge and/or post-translational modifications (such as glycosylation, methylation. phosphorylation, etc.). When the term "variant" is used in reference to a microorganism, it typically refers to a strain microbial strain having identifying characteristics of the species to which it belongs, while having at least one nucleotide sequence variation or identifiably different trait with respect to the parental strain, where the trait is genetically based (heritable). For example, for a *Nannochloropsis* strain, identifiable traits include the lack of chlorophyll b and c, which is different from other related microalgae.

Vector: The term "vector" refers to a nucleic acid construct designed for transfer of nucleic acid between different host cells. As used herein, "vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region, thereby capable of expressing DNA sequences and fragments in a host cell (in vivo) or in vitro.

Yield: As used herein, the term "yield" refers to the amount of harvestable plant material or plant-derived product, and is normally defined as the measurable produce of economic value of a crop. For crop plants, "yield" also means the amount of harvested material per acre or unit of production. Yield may be defined in terms of quantity or quality. The harvested material may vary from crop to crop, for example, it may be seeds, above ground biomass, roots, fruits, cotton fibers, any other part of the plant, or any plant-derived product which is of economic value. The term "yield" also encompasses yield potential, which is the maximum obtainable yield. Yield may be dependent on a number of yield components, which may be monitored by certain parameters. These parameters are well known to persons skilled in the art and vary from crop to crop. The term "yield" also encompasses harvest index, which is the ratio between the harvested biomass over the total amount of biomass.

All publications and patent applications mentioned in this specification are herein incorporated by reference to the same extent as if each individual publication or patent application was specifically and individually indicated to be incorporated by reference.

No admission is made that any reference constitutes prior art. The discussion of the references states what their authors assert, and the applicants reserve the right to challenge the accuracy and pertinence of the cited documents. It will be clearly understood that, although a number of prior art publications are referred to herein; this reference does not constitute an admission that any of these documents forms part of the common general knowledge in the art.

The discussion of the general methods given herein is intended for illustrative purposes only. Other alternative methods and embodiments will be apparent to those of skill in the art upon review of this disclosure.

*Nannochloropsis*

The genus *Nannochloropsis* is first termed by Hibberd (*Bot. J. Linn. Soc.*, 82: 93-119, 1981), by removing it from the class Chlorophyceae, and placing it in the class Eustigmatophyceae in the family Monodopsidaceae. The *Nannochloropsis* species are known mostly from the marine environment but also occur in fresh and brackish water. In general, the microorganisms have a relatively simple ultrastructure, and reduced morphology compared to neighboring taxa (Andersen et al., *Protist*, 149:61-74, 1998). The species of *Nannochloropsis* can be distinguishing from other related microalgae in that they lack chlorophyll b and c. Microorganisms of this genus are considered generally difficult to identify based on the morphological characteristics, because the cells are typically small (typically ~2 micrometers in diameter) and indistinguishable from other chlorophytes by light microscopy observation. Furthermore *Nannochloropsis* cells appear difficult to fix for electron microscopy. Therefore, the characterization of *Nannochloropsis* species is mostly done by sequence analyses of 18S rRNA genes and Rubisco (rbcL) genes (Andersen et al., 1998, supra). Nevertheless, to date numerous strains of *Nannochloropsis* have been described and deposited in various culture collections. According to nucleotide sequence data available at GenBank databases, at least 180 microbial samples have been identified as *Nannochloropsis*. A large majority of these strains are taxonomically placed in at least different seven species: *N. gaditana, N. granulata, N limnetica, N. maritime, N. aceanica, N oculata*, and *N. salina*.

Algal strains of *Nannochloropsis* are commonly cultivated in fish hatcheries as a food source for zooplankton production, such as rotifers and copepods, which in turn is used as feed for rearing larvae of many species of mollusks, crustaceans, and fish, because *Nannochloropsis* is well known as being capable to build up a high concentration of a range of different valuable pigments such as astaxanthin, canthaxanthin, chlorophyll a, and zeaxanthin. In addition, astaxanthin has been reported beneficial for human consumption because of its usefulness in preventing several diseases.

Furthermore, *Nannochloropsis* is considered a promising alga for industrial applications because of its ability to accumulate high levels of fatty acids, particularly polyunsaturated fatty acids (PUFA). Therefore, *Nannochloropsis* is often recognized as a good potential source for the dietary supplement of omega-3 fatty acid, and especially EPA, an important polyunsaturated fatty acid for human consumption for prevention of several diseases and medical conditions. In addition, *Nannochloropsis* is considered to be a potentially good material for a bioreactor to carry valuable heterologous protein because of easy culture, low production cost, high expression, and safety in the environment and in food (Hawkins and Nakamura, *Curr. Microbiol.* 1999) Recently, *Nannochloropsis* has been investigated for being potentially suitable for algal biofuel production, due to its relative ease of growth and high oil content (see, e.g., Radakovits et al., *Eukaryotic Cells,* 2010).

Acetohydroxyacid Synthase

One aspect of the present invention relates to the development of materials and methods that are useful for conferring the tolerance of cells and organisms, including microorganisms of the genus *Nannochloropsis,* to chemical compounds that inhibit AHAS activity in conjunction with the expression of novel gene sequences encoding acetohydroxyacid synthase (AHAS, EC 2.2.1.6). Acetohydroxyacid synthase, also known as acetolactate synthase (ALS), is the first enzyme that catalyzes the biosynthesis of the branched chain amino acids, e.g. valine, leucine and isoleucine, which is a common pathway in microorganisms and plants. In many species, the AHAS enzyme is comprised of two subunits: a large subunit having a catalytic role and a small subunit having a regulatory role (Duggleby and Pang, 2000, *J. Biochem. Mol. Biol.* 33:1-36). These two subunits are typically expressed from separate genes. While it has been widely reported that only large subunit has catalytic activity, at least two roles have been described for the small subunit: 1) the small subunit is involved in the allosteric feedback inhibition of the catalytic large subunit in the presence of valine, leucine or isoleucine, or combinations thereof; and (2) the small subunit enhances the activity of the large subunit in the absence of the above amino acids. To date, numerous single nucleotide substitutions in the large subunit have been reported to confer upon the enzyme a degree of insensitivity to one or more classes of herbicides (see, for example, Duggleby and Pang, 2000, supra.)

AHAS has two distinct metabolic roles, and thus it is designated as anabolic AHAS and catabolic AHAS depending on its function. In most organisms where AHAS is found, its anabolic function is associated with the biosynthesis of the branched-chain amino acids. However, in some microorganisms AHAS has another function in the fermentation pathway that catabolically forms butanediol and related compounds. These two classes of AHAS differ from each other in many aspects including, for examples, physiological activities, substrate specificities, and cofactor requirements. For example, anabolic AHAS activity is FAD-dependent, while its catabolic AHAS counterpart is not. Structurally distinguishing features between the two classes of AHAS have also been identified, and include a conserved motif (RFDDR) (SEQ ID NO:34) within the β-domain of anabolic AHASs but not in catabolic AHASs. This conserved motif appears to be a determinant of the FAD-dependent characteristic of anabolic AHASs (see, e.g., Le and Choi, Bull. Korean Chem. Soc. Vol. 26, No. 6, 2005). The equivalent motif of the catabolic AHASs is SPVEY, which is also reported to be conserved.

AHAS is the primary target site for at least five structurally distinct classes of chemical compounds, many of which are known herbicides, including the sulfonylureas (SUs), the imidazolinones (IMs), the triazolopyrimidines (also known as triazolopyrimidine sulfonamides, TPs), the pyrimidinylsalicylates (also known as pyrimidinylcarboxylates, PCs), and sulfonylaminocarbonyl-triazolinones (see, e.g., Shimizu et al., *Herbicides: Theory and Applications,* (Ed) Intech, 2011. As such, the term "AHAS inhibitor" or "AHAS-inhibiting compound", as used herein, refers to a compound that inhibits wild-type AHAS protein activity by at least 10% and is toxic to cells that contain wild-type AHAS. Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. For agricultural applications, several examples of commercially available imidazolinone herbicides are imazethapyr, imazaquin and imazapyr. Examples of sulfonylurea herbicides are chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfiuon, fluzasulfuron, imazosulfuron, pyrazosulfuron ethyl and halosulfuron.

Mutations in AHAS genes to transform the respective polypeptides to herbicide-insensitive forms have been reported to be a widespread mechanism for acquired resistance to the chemical compounds described above. One of the reasons for interest in herbicide-insensitive forms of AHAS is the possibility to use those as dominant selectable markers in construction of transgenic herbicide resistant microorganisms and plants. Numerous point mutations are known to result in herbicide resistance for AHAS in various species. By far, the most extensive studied AHAS polypeptides are those from model organisms, including *Saccharomyces cerevisiae,* thale cress *Arabidopsis thaliana,* and the green alga *Chlamydomonas reinhardtii.* In addition, spontaneous and induced mutations in the AHAS genes of bacteria (LaRossa and Smulski, *J. of Bacteriol.* 160:391-394, 1984; Wek et al., *Nucl. Acids Res.* 13, 3995-4010, 1985; Yadav et al., *Proc. Natl. Acad. Sci. USA,* 83, 4418-4422, 1986), yeast (Falco and Dumas, *Genetics* 109, 21-35, 1985), unicellular algae (Kovar et al, *Plant J* 29:109-117, 2002), and higher plants (Yadav et al., *Proc. Natl. Acad. Sci. USA,* 83, 4418-4422, 1986; Mazur et al., *Plant Physiol.* 85 11 10-1 11 7, 1987; Mazur and Falcon, *Annu. Rev. Plant Physiol. Plant Mol. Biol.* 40:441-470, 1989; Bernasconi et al., *J. Biol. Chem.* 270:17381-17385, 1995) have yield genes that confer resistance to high levels of several herbicides. In many cases, such mutated genes have been demonstrated to be useful as dominant selectable markers for genetic transformation. For example, plants resistant to imidazolinones, sulfonylureas, triazolopyrimidines, and pyrimidinyloxybenzoates have been successfully produced using seed, microspore, pollen, and callus mutagenesis in a variety of plant species, including major crops such as *Zea mays, Arabidopsis thaliana, Brassica napus* (i.e., canola), *Glycine max, Nicotiana tabacum,* sugarbeet (*Beta vulgaris*) and *Oryza sativa.* In most cases, a single, partially dominant nuclear gene could confer resistance. Similarly, AHAS gene from the green alga *Chlamydomonas reinhardtii* has also been studied and deployed as a dominant selectable marker for genetic transformation (Kovar et al., *Plant J* 29:109-117, 2002).

Although the AHAS proteins of various species differ in length by a few amino acids, the relative positions of residues subject to modification in accordance with the methods of the present invention are conserved (see, e.g., FIG. 1; TABLE 1; Duggleby and Pang, 2000, supra; U.S. Pat. No. 5,605,511; US. Pat. Appl. Nos. US20100287641, US20030166207). The mutations described in the present disclosure can also be expressed in terms of positions corresponding to the amino acid residues numbers of the *Arabidopsis* AHAS polypeptide (SEQ ID NO: 8). For example, residue 36 of *Nannochloropsis gaditana* AHAS (disclosed herein as SEQ ID NO: 1) correspond to residue 122 of the *Arabidopsis* AHASL, which corresponds to residue 90 of maize AHASL, residue 104 of *Brassica napus* AHASL 1A, residue 107 of *B. napus* AHASL 1C, residue 96 of *Oryza sativa* AHASL, residue 113 of *Amaranthus*

AHASL, residue 120 of *Camelina microcarpa* AHASL1, residue 117 of *Camelina microcarpa* AHASL2, residue 26 of *Escherichia coli* ilvG, residue 117 of *Saccharomyces cerevisiae* AHASL (SEQ ID NO: 9), residue 113 of sugar beet AHAS, residue 111 of cotton AHAS, residue 109 of *Solanum tuberosum* AHASL1, residue 111 of *Solanum tuberosum* AHASL2, residue 92 of *Lolium multillorum*, residue 27 of *Solanum ptychanthum*, residue 93 of *Sorghum bicolor*, residue 103 of *Glycine max* AHAS, residue 107 of *Helianthus annuus* AHASL1, residue 101 of *Helianthus annuus* AHASL2, residue 97 of *Helianthus annuus* AHASL3, residue 59 of *Triticum aestivum* AHAS, residue 100 of *Xanthium* sp. AHAS, residue 37 of *Pophyridium* sp. AHAS (SEQ ID NO: 7), and residue 123 of *Chlamydomonas reinhardtii* AHAS (SEQ ID NO: 10). These correspondences are well known to those of skill in the art. See, e.g., FIG. 1 and U.S. Pat. Appl. Nos. US20100287641. Non-limiting examples of conserved residues, motifs, domains, and regions of correspondence relevant to the AHAS sequences disclosed in the present application are set forth in FIG. 1 and TABLE 1. Based on such correspondence, the corresponding conserved positions in AHAS sequences not specifically disclosed herein can be readily determined by the skilled artisan in the art.

from any *Nannochloropsis* organism, or the use of *Nannochloropsis* AHAS genes to confer resistance to chemical compounds capable of inhibiting AHAS activity, including imidazolinone-class inhibitors, pyrimidyloxybenzoates, sulfonylurea compounds, sulfonlyaminocarbonyl-triazolinones, and triazolopyrimidines.

Importantly, examples of gene sequences with substantial homology to known AHAS genes but that do not encode enzymes having the capability to catalyze the synthesis of acetohydroxyacid synthase have been reported in various organisms (Chipman et al., *Biochimica et Biophysica Acta* 1385:401-419, 1998). Therefore, it would not have been obvious that a cloned AHAS homolog in fact encodes AHAS. In order to definitively determine whether the cloned *Nannochloropsis* genes disclosed herein were true AHAS genes, the present Applicants have further demonstrated, through the isolation of mutant forms of the *N. gaditana* AHAS gene, a positive correlation of metsulfuron methyl-resistance with point mutations in the coding sequence of the gene (see, e.g., Example 3 of the present disclosure).

Various embodiments of the present invention are described below with regard to *Nannochloropsis* AHAS genes and/or AHAS proteins of the present invention. It is to be understood, however, that the general definitions of terms

TABLE 1

Concordant positions of conserved amino acid residues in AHAS polypeptides from *Nannochloropsis gaditana*, *Nannochloropropsis oculata*, *Nannochloropsis salina*, *Arabidopsis thaliana*, and *Saccharomyces cerevisae*. AHAS polypeptides from *Arabidopsis thaliana* and *Saccharomyces cerevisae* are commonly used as reference sequence in comparative sequence analyses because structural features and residues important for the enzymatic activity and physiological function of AHAS from these two species have been most extensively characterized.

| A. thaliana SEQ ID NO: 8 | S. cerevisiae SEQ ID NO: 9 | N. gaditana SEQ ID NO: 1 | N. oculata SEQ ID NO: 3 | N. salina SEQ ID NO: 5 |
|---|---|---|---|---|
| Q95 | V90 | R9 | R9 | R9 |
| G121 | G116 | G35 | G35 | G35 |
| A122 | A117 | A36 | A36 | A36 |
| M124 | L119 | L38 | L38 | L38 |
| V139 | V134 | I56 | I56 | I56 |
| P197 | P192 | G114 | G114 | G114 |
| R199 | S194 | A116 | A116 | A116 |
| A205 | A200 | A122 | A122 | A122 |
| V254 | L249 | I171 | I171 | I171 |
| K256 | K251 | K173 | K173 | K173 |
| Q269 | T264 | I186 | I186 | I186 |
| M277 | A272 | N194 | N194 | N194 |
| D315 | D315 | A234 | A234 | A234 |
| M351 | M354 | M272 | M272 | M272 |
| D375 | D378 | D296 | D296 | D296 |
| D376 | D379 | D297 | D297 | D297 |
| S398 | P410 | P319 | P319 | P319 |
| K416 | T428 | K337 | K337 | K337 |
| L426 | N/A | S348 | N348 | N348 |
| A430 | K437 | P352 | P352 | P352 |
| V439 | E446 | F361 | F361 | F361 |
| N442 | A449 | E364 | E364 | E364 |
| N445 | N452 | V367 | L367 | L367 |
| V571 | V583 | V491 | V491 | V491 |
| W574 | W586 | W494 | W494 | W494 |
| F578 | F590 | F498 | F498 | F498 |
| K580 | E592 | D500 | D500 | D500 |
| S653 | G657 | P567 | P567 | P567 |
| G654 | G658 | G568 | G568 | G568 |

As discussed in detail above, numerous mutant forms of genes encoding acetohydroxyacid synthase from many organisms have been used previously as selectable markers for genetic transformation of microorganisms and plants. However, there are no reports prior to the present invention that describe the sequences or properties of the AHAS genes and methods are intended to apply to the discussion of other genes, nucleic acids and proteins disclosed herein.

In some embodiments of the present invention, there are provided the identification, isolation and production of nucleic acid sequences encoding selectable markers that are suitable for use in recombinant constructs for genetic transformation of *Nannochloropsis* microorganisms. Such selectable markers may allow for the selection of microorganisms that have been successfully transformed with the recombinant constructs of the present invention. In some preferred embodiments, selectable markers useful for the transformation of a *Nannochloropsis* species encode a *Nannochloropsis* acetohydroxyacid synthase. Particularly preferred polypeptides include AHAS peptides have been modified, mutated, or otherwise selected, to have a reduced sensitivity to the inhibition by imidazolinone-class inhibitors, pyrimidyloxybenzoates, sulfonylurea compounds, sulfonlyaminocarbonyl-triazolinones, and triazolopyrimidines. An example of preferred acetohydroxyacid synthases of the present invention is a homolog of a naturally-occurring acetohydroxyacid synthase.

An acetohydroxyacid synthase in accordance with the present disclosure is a polypeptide that has acetohydroxyacid synthase biological activity. Accordingly, AHAS polypeptides of the present invention include full-length proteins, fusion proteins, or any homolog of a naturally-occurring acetohydroxyacid synthase. As discussed elsewhere herein, a homolog of an acetohydroxyacid synthase includes proteins which differ from a naturally-occurring acetohydroxyacid synthase in that at least one or a few, but not limited to one or a few, amino acids have been deleted (e.g., a truncated version of the protein, such as a peptide or fragment), inserted, substituted and/or derivatized (e.g., by glycosylation, phosphorylation, acetylation, myristoylation, prenylation, palmitation, amidation and/or addition of glycosylphosphatidyl inositol). Preferred homologs of a naturally-occurring acetohydroxyacid synthase are described in detail below.

The Polynucleotides and Polypeptides of the Invention

In one aspect of the present invention, the disclosure provides novel isolated nucleic acid molecules, nucleic acid molecules that interfere with these nucleic acid molecules, nucleic acid molecules that hybridize to these nucleic acid molecules, and substantially purified nucleic acid molecules that encode the same protein due to the degeneracy of the DNA code. Additional embodiments of the present application further include the polypeptides encoded by the substantially purified nucleic acid molecules of the present invention.

The polypeptides and polypeptides of the present invention will preferably be "biologically active" with respect to either a structural attribute, such as the capacity of a nucleic acid to hybridize to another nucleic acid molecule, or the ability of a polypeptide to be bound by an antibody (or to compete with another molecule for such binding). Alternatively, such an attribute may be catalytic and thus involve the capacity of the molecule to mediate a chemical reaction or response.

The polypeptides and polypeptides of the present invention may also be recombinant. As used herein, the term recombinant means any molecule (e.g. DNA, peptide etc.), that is, or results, however indirect, from human manipulation of a polynucleotide or polypeptide.

Preferably, an isolated nucleic acid molecule of the present invention is produced using recombinant DNA technology (e.g., polymerase chain reaction (PCR) amplification, cloning, etc.) or chemical synthesis. Isolated nucleic acid molecules include natural nucleic acid molecules and homologs thereof, including, but not limited to, natural allelic variants and modified nucleic acid molecules in which nucleotides have been inserted, deleted, and/or substituted, in such a manner that such modifications provide the desired effect on AHAS biological activity as described herein. Protein homologs (e.g., proteins encoded by nucleic acid homologs) are discussed in further detail elsewhere herein.

A nucleic acid molecule homolog can be produced using a number of methods known to those skilled in the art (see, for example, Sambrook et al., 1989, supra). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologs can be selected from a mixture of modified nucleic acids by screening for the function of the protein encoded by the nucleic acid and/or by hybridization with a wild-type gene.

Nucleic acid molecules or fragments thereof of the present invention are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., In: *Molecular Cloning, A Laboratory Manual,* 2nd Edition, Cold Spring Harbor Press, Cold Spring Harbor, N.Y. (1989), and by Haymes et al. In: *Nucleic Acid Hybridization, A Practical Approach,* IRL Press, Washington, D.C. (1985). Departures from complete complementarity are therefore permissible, as long as such departures do not completely preclude the capacity of the molecules to form a double-stranded structure. Thus, in order for a nucleic acid molecule or fragment thereof of the present invention to serve as a primer or probe it needs only be sufficiently complementary in sequence to be able to form a stable double-stranded structure under the particular solvent and salt concentrations employed.

Appropriate stringency conditions which promote DNA hybridization include, for example, 6.0× sodium chloride/sodium citrate (SSC) at about 45° C., followed by a wash of 2.0×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. These conditions are known to those skilled in the art, or can be found in *Current Protocols in Molecular Biology,* John Wiley & Sons, N.Y. (1989), 6.3.1-6.3.6. For example, low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989, supra). High stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70×C for several hours to overnight. High stringency conditions are preferably provided by 6×SSC, 5×Denhardt's solution, 100 mg/mL fish sperm DNA, and 0.1% (w/v) SDS, with incubation at 55×C for several hours. Hybridization is generally followed by several wash steps. The wash compositions generally comprise 0.5× to about 10×SSC, and 0.01% (w/v) to about 0.5% (w/v) SDS with a 15-min incubation at about 20° C. to about 70° C. Preferably, the nucleic acid segments remain hybridized after washing at least one time in 0.1×SSC at 65° C.

According to some embodiments of the present application, nucleic acid molecules of the present invention will include those nucleic acid molecules that specifically hybridize to one or more of the nucleic acid molecules set forth in the Sequence Listing or complements thereof under high stringency conditions. In a particularly preferred embodiment, nucleic acid molecules of the present invention preferably comprise a nucleic acid sequence that hybridizes, under low, moderate, or high stringency conditions, to a nucleic acid sequence selected from the group consisting of SEQ ID NO: 2, SEQ ID NO: 4, and SEQ ID NO: 6, a complement thereof or a fragment of either.

A subset of the nucleic acid molecules of this invention includes fragments of the disclosed polynucleotides consisting of oligonucleotides of at least 12, at least 15, preferably at least 16 or 17, more preferably at least 18 or 19, and even more preferably at least 20 or more, consecutive nucleotides. Such oligonucleotides are fragments of the larger molecules having a sequence selected from the polynucleotide sequences in the Sequence Listing, and find use, for example, as interfering molecules, probes and primers for detection of the polynucleotides of the present invention.

The minimum size of a nucleic acid molecule of the present invention is a size sufficient to form a probe or oligonucleotide primer that is capable of forming a stable hybrid (e.g., under moderate, high or very high stringency conditions) with the complementary sequence of a nucleic acid molecule useful in the present invention, or of a size sufficient to encode an amino acid sequence having a biological activity of at least one domain of an acetohydroxyacid synthase according to the present invention. As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a sequence sufficient to encode a biologically active fragment of a domain of an acetohydroxyacid synthase, an entire acetohydroxyacid synthase, or several domains within an open reading frame encoding an acetohydroxyacid synthase.

In another embodiment, the present invention provides nucleotide sequences comprising regions that encode polypeptides. The encoded polypeptides may be the complete protein encoded by the gene represented by the polynucleotide, or may be fragments of the encoded protein. Preferably, polynucleotides provided herein encode polypeptides constituting a substantial portion of the complete protein, and more preferentially, constituting a sufficient portion of the complete protein to provide the relevant biological activity, e.g., acetohydroxyacid synthase activity.

Of particular interest are polynucleotides of the present invention that encode an acetohydroxyacid synthase. Such polynucleotides may be expressed in transgenic cells or transgenic organisms to produce cells and organisms having modulated sensitivity to an herbicide.

In some embodiments, nucleic acid molecules that are fragments of these AHAS-encoding nucleotide sequences are also encompassed by the present invention. An "AHAS fragment", as used herein, is intended to be a portion of the nucleotide sequence encoding an acetohydroxyacid synthase. A fragment of a nucleotide sequence may encode a biologically active portion of an acetohydroxyacid synthase, or it may be a fragment that can be used as a hybridization probe or PCR primer using methods disclosed below. Nucleic acid molecules that are fragments of an AHAS nucleotide sequence comprise at least about 50, 100, 200, 300, 400, 500, 600, 700, 800, 900, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350 contiguous nucleotides, or up to the number of nucleotides present in a full-length AHAS encoding nucleotide sequence disclosed herein depending upon the intended use. The term "contiguous nucleotides" is intended to mean nucleotide residues that are immediately adjacent to one another. Fragments of the nucleotide sequences of the present invention include those that encode protein fragments that retain the biological activity of an acetohydroxyacid synthase. By "retains activity" is intended that the fragment will have at least about 30%, at least about 50%, at least about 70%, 80%, 90%, 95% or higher of the AHAS activity of the acetohydroxyacid synthase. Methods for measuring acetohydroxyacid synthase activity are well known in the art. See, for example, Hill and Duggleby, *Biochem. J.*, 335:653-661, 1998; Schloss et al., *Biochemistry*, 24:4952-4959, 1985; Singh et al., *Annal. Biochem.* 171:173-179, 1988; Choi et al., *FEBS Lett.* 579:4903-4910, 2005; and U.S. Pat. No. 5,633,437.

A fragment of an AHAS-encoding nucleotide sequence that encodes a biologically active portion of a protein of the invention will encode at least about 15, 25, 30, 50, 75, 100, 125, 150, 175, 200, 250, 300, 350, 400, 450, 500, 550, 600, 650, 700, 750, 800, 850, 900, 950, 1000, 1050, 1100 contiguous amino acids, or up to the total number of amino acids present in a full-length AHAS protein of the invention. In some embodiments, the fragment is a proteolytic cleavage fragment. For example, the proteolytic cleavage fragment may have an N-terminal or a C-terminal truncation of at least about 100 amino acids, about 120, about 130, about 140, about 150, or about 160 amino acids relative to any AHAS amino acid sequences set forth in the Sequence Listing.

Also of interest in the present invention are variants of the polynucleotides provided herein. Such variants may be naturally-occurring, including homologous polynucleotides from the same or a different species, or may be non-natural variants, for example polynucleotides synthesized using chemical synthesis methods, or generated using recombinant DNA techniques. With respect to nucleotide sequences, degeneracy of the genetic code provides the possibility to substitute at least one base of the protein encoding sequence of a gene with a different base without causing the amino acid sequence of the polypeptide produced from the gene to be changed. Hence, the DNA of the present invention may also have any base sequence that has been changed from any polynucleotide sequence in the Sequence Listing by substitution in accordance with degeneracy of the genetic code. References describing codon usage are readily publicly available.

The skilled artisan in the art will further appreciate that changes can be introduced by mutation of the nucleotide sequences of the invention, thereby leading to changes in the amino acid sequence of the encoded AHAS proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted nonessential amino acid residues. A "nonessential" amino acid residue, as used herein, is a residue that can be altered from the wild-type sequence of an AHAS protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In a particular non-limiting exemplification, conserved residues, domains and motifs of AHAS sequences are indicated in TABLE 1 and FIG. 1. As discussed above, it will be appreciated by one skilled in the art that amino acid substitutions may be made in non-conserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of the amino acid sequences of the present invention and known AHAS sequences. Examples of residues that are conserved but that may allow conservative amino acid substitutions and still retain activity include, for example, residues that have only conservative substitutions between all proteins contained in an alignment of the amino acid sequences of the present invention and known AHAS sequences. However, one of skill in the art would understand that functional variants may have minor conserved or non-conserved alterations in the conserved residues.

In some embodiments of the present invention, such acetohydroxyacid synthase variants include proteins having an amino acid sequence that differs from any one of the polypeptides in the Sequence Listing, by an amino acid deletion, insertion, or substitution at one or more of the positions corresponding to the conserved amino acid residues as identified in Table 1 and FIG. 1, and combinations of any thereof. In some preferred embodiments, such acetohydroxyacid synthase variants include proteins having an amino acid sequence that differs from any one of the polypeptides of SEQ ID NOs: 1, 3, and 5 in the Sequence Listing, by an amino acid deletion, insertion, or substitution at one or more of the positions corresponding to the conserved amino acid residues as identified in Table 1 and FIG. 1, and combinations of any thereof.

In some particularly preferred embodiments of the present invention, acetohydroxyacid synthase variants of interest include proteins having an amino acid sequence that differs from any one of the polypeptides of SEQ ID NOs: 1, 3, and 5 in the Sequence Listing, by an amino acid deletion, insertion, or substitution at one or more of the positions corresponding to the following conserved amino acid residues: R9, G35, A36, L38, I56, G114, A116, A122, I171, K173, I186, N194, A234, M272, D296, D297, P319, K337, S348, P352, F361, E364, V367, V491, W494, F498, D500, P567, and G568, and combinations of any thereof, of the polypeptide of SEQ ID NO: 1. These positions correspond to known mutation sites in a yeast Saccharomyces cerevisiae acetolactate synthase ALS (i.e., V90, G116, A117, L119, V134, P192, S194, A200, L249, K251, T264, A272, D315, M354, D378, D379, P410, T428, N/A, K437, FA-46, A449, N452, V583, W586, F590, E592, G657, and G658, respectively) (see Mazur and Falco, Annu. Rev. Plant Physiol. Plant Mol. Biol. 40:441-470, 1989) and/or in an AHASL large subunit of Arabidopsis thaliana (i.e., Q95, G121, A122, M124, V139, P197, R199, A205, V254, K256, Q269, M277, D315, M351, D375, D376, S398, K416, L426, A430, V439, N442, N445, V571, W574, F578, K580, S653, and G654, respectively (see Duggleby and Pang, 2000, supra). Other possible mutation sites will be apparent to those skilled in the art based on amino acid mutations that have been reported successful in the AHAS polypeptides from other organisms.

Alternatively, variant nucleotide sequences can be made by introducing mutations randomly along all or part of the coding sequence, such as by saturation mutagenesis, and the resultant mutants can subsequently be screened for ability to confer AHAS activity in order to identify mutants that retain AHAS activity. For example, following mutagenesis, the encoded protein can be expressed recombinantly, and the activity of the protein can be determined using standard assay techniques. Methods for assaying acetohydroxyacid synthase activity are well known in the art. See, for example, Hill and Duggleby, 1998, supra; Schloss et al., 1985, supra; Singh et al., 1988, supra; Choi et al., 2005, supra; and U.S. Pat. No. 5,633,437.

In another aspect of the present invention, AHAS polypeptides are also encompassed within the present invention. In an embodiment of this aspect, by "AHAS polypeptide" is intended a polypeptide having an amino acid sequence comprising any one of the amino acid sequences from a *Nannochloropsis* organism set forth in the Sequence Listing. Fragments, biologically active portions, and variants thereof are also provided, and may be used to practice the methods of the present invention.

Altered or improved variants: It is contemplated that DNA sequences of an acetohydroxyacid synthase may be altered by various methods, and that these alterations may result in DNA sequences encoding proteins with amino acid sequences different than that encoded by an AHAS of the present invention. This protein may be altered in various ways including amino acid substitutions, deletions, truncations, and insertions of one or more amino acids of the polypeptide sequences from a *Nannochloropsis* organism set forth in the Sequence Listing, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130 or more amino acid substitutions, deletions or insertions.

Methods for such manipulations are generally known in the art. For example, amino acid sequence variants of an AHAS protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired AHAS activity. However, it is understood that the ability of an AHAS to confer herbicide-tolerance activity may be improved by the use of such techniques upon the compositions of this invention. For example, one may express an AHAS in host cells that exhibit high rates of base-misincorporation during DNA replication, such as Stratagene XL-1 Red cell (Fischer Scientific). After propagation in such strains or cells, one can isolate the AHAS-encoding DNA (for example by preparing plasmid DNA, or by amplifying by PCR and cloning the resulting PCR fragment into a vector), followed by culture the mutated AHAS genes in a non-mutagenic strain or cell, and identify mutated AHAS genes with an modulated-tolerance to herbicides, for example by performing an assay to test for AHAS activity in vivo and in vitro.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Domain swapping or shuffling is another mechanism for generating altered AHAS proteins. Conversed domains may be swapped between AHAS proteins, resulting in hybrid or chimeric AHAS with improved herbicide-tolerance activity or target spectrum. Methods for generating recombinant proteins and testing them for herbicide-tolerance activity are well known in the art.

The skilled artisan will further appreciate that any of a variety of methods well known in the art may be used to obtain one or more of the above-described polypeptides. The polypeptides of the invention can be chemically synthesized or alternatively, polypeptides can be made using standard recombinant techniques in heterologous expression systems such as *E. coli*, yeast, insects, etc.

As discussed above, an isolated acetohydroxyacid synthase, according to the present invention, is a polypeptide having acetohydroxyacid synthase activity that has been removed from its natural milieu (i.e., that has been subject to human manipulation) and can include purified proteins, partially purified proteins, recombinantly produced proteins, and synthetically produced proteins, for example. Preferably, an isolated acetohydroxyacid synthase of the present invention is produced recombinantly. A "*Nannochloropsis* acetohydroxyacid synthase" refers to an acetohydroxyacid synthase (including a homolog of a naturally-occurring acetohydroxyacid synthase) from a *Nannochloropsis* microorganism or that has been otherwise produced from the knowledge of the structure (e.g., sequence) of a naturally-occurring acetohydroxyacid synthase from a *Nannochloropsis* microorganism. In other words, a *Nannochloropsis* acetohydroxyacid synthase includes any acetohydroxyacid synthase that has the structure and function of a naturally-occurring acetohydroxyacid synthase from a *Nannochloropsis* microorganism or that is a biologically active (i.e., has biological activity) homolog of a naturally-occurring acetohydroxyacid synthase from a *Nannochloropsis* microorganism as described in detail herein. As such, a *Nannochloropsis* acetohydroxyacid synthase can include purified, partially purified, recombinant, mutated/modified and synthetic polypeptides.

In general, the biological activity or biological action of a protein or domain refers to any function(s) exhibited or performed by the protein or domain that is ascribed to the naturally-occurring form of the protein as measured or observed in vivo (i.e., in the natural physiological environment of the protein) or in vitro (i.e., under laboratory conditions). As used herein, a functional domain of an acetohydroxyacid synthase is a domain that is capable of performing a biological function of an acetohydroxyacid synthase. For example, a biological activity of an acetohydroxyacid synthase and the individual domains that make up an acetohydroxyacid synthase includes acetohydroxyacid synthases have been discussed in detail elsewhere herein.

With regard to the acetohydroxyacid synthases of the present invention, it is preferred that modifications present in each of the acetohydroxyacid synthase homologs, as compared to a naturally-occurring acetohydroxyacid synthase, do not substantially change, or at least do not substantially decrease, the basic biological activity of the synthase as compared to the naturally-occurring protein. However, such homologs may have differences in characteristics other than the functional, or enzymatic, activity of the protein as compared to the naturally-occurring form, such as a decreased sensitivity to inhibition by certain compounds as compared to the naturally-occurring protein. Preferably, a homolog of a naturally-occurring acetohydroxyacid synthase has reduced (i.e., decreased, lessened) sensitivity to compounds that bind to and inactivate naturally-occurring acetohydroxyacid synthases as compared to the naturally occurring acetohydroxyacid synthase from which the homolog was derived. For example, sulfonylurea compounds, such as sulfometuron methyl (SMM), are often toxic to cells because they are able to bind to and inactivate acetohydroxyacid synthase. Imidazolinones, triazolopyrimidines, and other similar compounds (referred to generally herein as imidazolinone-class inhibitors) have also been shown to bind to and inactivate AHAS. Therefore, a homolog of a naturally occurring acetohydroxyacid synthase preferably has reduced sensitivity to sulfonylurea compounds, as well as to imidazolinone-class inhibitors (e.g., by having disrupted binding sites for such inhibitors or binding sites with reduced affinity for the inhibitor) and to pyrimidinyl oxybenzoates, while maintaining acetohydroxyacid synthase enzymatic activity.

Another embodiment of the present invention includes a recombinant nucleic acid molecule comprising a nucleic acid sequence encoding an amino acid sequence having a biological activity of at least one domain of an acetohydroxyacid synthase as described herein. Such nucleic acid sequences are described in detail above. Typically, a recombinant nucleic acid molecule includes at least one nucleic acid molecule of the present invention operably linked to one or more transcription control sequences. As used herein, the phrase "recombinant molecule" or "recombinant nucleic acid molecule" primarily refers to a nucleic acid molecule or nucleic acid sequence operably linked to a transcription control sequence, but can be used interchangeably with the phrase "nucleic acid molecule", when such nucleic acid molecule is a recombinant molecule as discussed herein.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell. Yet in other embodiments, a recombinant molecule of the present invention comprises an organelle targeting signal to enable an expressed protein to be transported and delivered to the target cellular organelle. It will be appreciated by one skilled in the art that a variety of organelle targeting signals can be used including, but not limited to, nuclear localization signal (NLS), chloroplast targeting signal, and mitochondria-targeting sequence.

One or more recombinant nucleic acid molecules of the present invention can be used to produce an encoded product (e.g., a fatty acid biosynthetic enzyme, a PUFA PKS domain, protein, or system) of the present invention. In one embodiment, an encoded product is produced by expressing a nucleic acid molecule as described herein under conditions effective to produce the protein. A preferred method to produce an encoded protein is by introducing into a host cell one or more recombinant molecules to form a recombinant cell. Suitable host cells include, but are not limited to, any bacterial, fungal (e.g., yeast), insect, algal, protozoa, protist, plant or animal cell. Of particular interest are host cells of green micro-algae, phytoplankton, and cells of *Nannochloropsis* species. Host cells can be either non-transgenic cells or cells that are already genetically engineered with at least one other recombinant nucleic acid molecule.

In some embodiments, the recombinant nucleic acid molecule is a recombinant vector. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences. The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain one or more selectable genetic markers.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced, e.g., an enzyme involved in a fatty acid biosynthesis pathway is inserted into the recombinant vector to produce a recombinant nucleic acid molecule. The nucleic acid sequence encoding the protein to be produced is inserted into the vector in a manner that operably links the nucleic acid sequence to regulatory sequences in the vector which enable the transcription and translation of the nucleic acid sequence within the recombinant host cell.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule is used to delete or inactivate an endogenous gene within the host cell or microorganism (i.e., used for targeted gene disruption, modification, or knock-out technology). Such a vector may also be known in the art as a "knock-out" vector. In one aspect of this embodiment, a portion of the vector, which is typically the nucleic acid molecule inserted into the vector (i.e., the insert), has a nucleic acid sequence that is homologous to a nucleic acid sequence of a target gene in the host cell (i.e., a gene which is targeted to be modified, deleted, or inactivated). The nucleic acid sequence of the vector insert is designed to bind to the target gene such that the target gene and the insert undergo homologous recombination, whereby the endogenous target gene is modified, deleted, inactivated or attenuated (i.e., by at least a portion of the endogenous target gene being mutated or deleted).

General discussion above with regard to recombinant nucleic acid molecules and transformation of host cells is intended to be applied to any recombinant nucleic acid molecule discussed herein, including those encoding any amino acid sequence having a biological activity of at least one domain from an acetohydroxyacid synthase, those encoding amino acid sequences from other acetohydroxyacid synthases, and those encoding other proteins or domains.

Use of the Molecules and Methods of the Invention
Compositions and Methods for Making Recombinant Organisms In one aspect of the present invention, provided are compositions and methods useful for introducing a polypeptide or polynucleotide into an organism or a cell. "Introducing" is intended to mean presenting to the organism or cell the polypeptide or polynucleotide in such a manner that the sequence gains access to the interior of a cell of the organism. The methods of the invention do not depend on a particular method for introducing a sequence into an organism or cell, only that the polypeptide or polynucleotide gains access to the interior of at least one cell or the organism. Methods for introducing a polypeptide or polynucleotide into organism are well known in the art including, but not limited to, stable transformation methods, transient transformation methods, virus-mediated methods, and breeding.

Accordingly, encompassed by the present invention are methods to genetically modify microbial or plant cells by genetically modifying at least one nucleic acid sequence in the organism that encodes an amino acid sequence having the biological activity of at least one functional domain of an acetohydroxyacid synthase according to the present invention, and/or expressing at least one recombinant nucleic acid molecule comprising a nucleic acid sequence encoding such amino acid sequence. Various embodiments of such sequences, methods to genetically modify an organism, and specific modifications are described in detail elsewhere herein. Typically, the methods are used to produce a particular genetically modified organism that produces a particular bioactive molecule or molecules.

"Stable transformation" is intended to mean that the nucleic acid construct introduced into an organism integrates into the genome of the organism and is capable of being inherited by the progeny thereof. "Transient transformation" is intended to mean that a polynucleotide is introduced into the organism and does not integrate into the genome or a polypeptide is introduced into an organism. A "stable vector transformation" is intended to mean that the nucleic acid construct introduced into the organism and is capable of being inherited by the progeny thereof.

One aspect of the present invention relates to identification, isolation, and production of nucleic acid sequences encoding selectable markers that are suitable for use in recombinant constructs for the transformation of organisms, particularly microorganisms and plants, and more particularly microorganisms of the genus *Nannochloropsis*. Such selectable markers allow the selection of organisms that have been successfully transformed with the recombinant constructs of the invention. Examples of selectable markers useful for the transformation of organisms include the acetohydroxyacid synthases according to the present invention. Preferably, the acetohydroxyacid synthases have been modified, mutated, or otherwise selected, to confer reduced sensitivity to the inhibition by imidazolinone-class inhibitors, pyrimidyloxybenzoates, sulfonylurea compounds, sulfonylaminocarbonyl-triazolinones, and triazolopyrimidines (i.e. such AHAS are homologs of a naturally-occurring AHAS disclosed herein).

A subject recombinant nucleic acid may comprise a subject polynucleotide, e.g., an expression cassette for production of a resistance-conferring AHAS polypeptide in a host cell, which is employed as a marker for selection as discussed above, as well as a second expression cassette for expression of a protein of interest in the host cell.

The protein of interest encoded by the second expression cassette may be for example an enzyme, a therapeutic protein, a reporter protein, a food additive, or a foodstuff or the like.

Of particular interest in the present invention are expression cassettes that encode polypeptides involved in one or more important characteristics of the host cell. Such polypeptides may be produced in transgenic cells that do not express such polypeptides, or may be over-expressed in cells that already express such polypeptides to provide cells having improved phenotypic properties and/or improved response to environmental conditions. Alternatively, decreased expression of such polypeptides may also be desired. Such decreased expression can be obtained by use of the polynucleotide sequences provided herein, for example in antisense, RNA interference, or co-suppression methods. A summary of such improved characteristics and polypeptides of interest for increased or decreased expression is provided below.

Amino acid content: Improving the amino acid content of cells is useful to provide cells having increased amino acid levels, improved nutritional value, and/or improved flavor profiles. It is particularly useful to provide cells having increased levels of essential amino acids, including, lysine, tryptophan, and methionine. It is also particularly useful to provide cells having increased levels of branched-chain amino acids, i.e., leucine, isoleucine, and valine. Polypeptides useful for altering the amino acid content of cells include, but are not limited to, polypeptides involved in amino acid biosynthesis or metabolism such as glutamine synthetase, glutamate synthase, glutamate dehydrogenase, anthranilate synthase, and dihydrodipicolinate synthase, polypeptides related to amino acid storage, and polypeptides related to seed development.

Carbohydrate content: The carbohydrate content of cells can be altered by modulating carbohydrate metabolism, for example by increasing production and/or transport of sugars (e.g., sucrose). For example, plant yield can be improved by effects on carbohydrate metabolism. Polypeptides useful for increasing carbohydrate content of cells by affecting carbohydrate metabolism include but are not limited to polypeptides involved in sugar or starch metabolism, carbon assimilation or carbohydrate transport, including, for example transporters of sugars, sucrose, or glucose/hexose; enzymes involved in glycolysis/gluconeogenesis; the pentose phosphate cycle; or raffinose biosynthesis; and polypeptides involved in glucose signaling, such as SNF1 complex proteins.

Fatty Acid/Oil content: Polypeptides useful for providing increased fatty acid and oil quantity and/or quality include but are not limited to polypeptides involved in saturated fatty acid synthesis pathways, mono- and polyunsaturated fatty acid (PUFA) synthesis pathways (e.g., fatty acid elongases, fatty acid desaturases, PUFA-polyketide synthases), glycerolipid biosynthesis, beta-oxidation enzymes, and enzymes involved in biosynthesis of nutritional compounds, such as carotenoids and tocopherols.

Photosynthesis capacity: Polypeptides related to cell photosynthetic capacity are of interest for increasing the photosynthetic capacity of cell and increasing biomass and/or yields. Polypeptides useful for increasing the rate of photosynthesis include phytochromes, photosystem I and II proteins, electron carriers, ATP synthase, NADH dehydrogenase and cytochrome oxidase. In addition, of particular interest are polypeptides useful for modulating chlorophyll content. Polypeptides related to chlorophyll content include but are not limited to ribosomal polypeptides, photosystem I polypeptides, photosystem II polypeptides, photosynthetic electron proteins, proteins of the ATP synthase complex, and carbon fixation enzymes.

In some embodiments, the protein of interest encoded by the expression cassette may be an enzyme such as a carbohydrase, such as an α-amylase, an alkaline α-amylase, a β-amylase, a cellulase; a dextranase, an α-glucosidase, an α-galactosidase, a glucoamylase, a hemicellulase, a pentosanase, a xylanase, an invertase, a lactase, a naringanase, a pectinase or a pullulanase; a protease such as an acid protease, an alkali protease, bromelain, ficin, a neutral protease, papain, pepsin, a peptidase, rennet, rennin, chymosin, subtilisin, thermolysin, an aspartic proteinase, or trypsin; a lipase or esterase, such as a triglyceridase, a phospholipase, a pregastric esterase, a phosphatase, a phytase, an amidase, an iminoacylase, a glutaminase, a lysozyme, or a penicillin acylase; an isomerase such as glucose isomerase; an oxidoreductases, e.g., an amino acid oxidase, a catalase, a chloroperoxidase, a glucose oxidase, a hydroxysteroid dehydrogenase or a peroxidase; a lyase such as a acetolactate decarboxylase, an aspartic β-decarboxylase, a fumarese or a histadase; a transferase such as cyclodextrin glycosyltranferase; or a ligase, for example. In particular embodiments, the protein may be an aminopeptidase, a carboxypeptidase, a chitinase, a cutinase, a deoxyribonuclease, an α-galactosidase, a β-galactosidase, a β-glucosidase, a laccase, a mannosidase, a mutanase, a pectinolytic enzyme, a polyphenoloxidase, ribonuclease or transglutaminase, for example. The enzyme may be a wild-type enzyme or a variant of a wild-type enzyme. In addition the enzyme may be a hybrid enzyme that includes fragments of different enzymes.

In some other embodiments, the protein of interest encoded by the second expression cassette may be a therapeutic protein (i.e., a protein having a therapeutic biological activity). Examples of suitable therapeutic proteins include: erythropoietin, cytokines such as interferon-α, interferon-β, interferon-γ, interferon-o, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, IgA, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist. Antibody proteins, e.g., monoclonal antibodies that may be humanized, are of particular interest.

In some further embodiments, the protein encoded by the second expression cassette may be a reporter protein. Such reporter proteins may be optically detectable, chromogenic, or colorigenic, for example. In this embodiment, the protein may be a β-galactosidase (lacZ), β-glucuronidase (GUS), luciferase, alkaline phosphatase, nopaline synthase (NOS), chloramphenicol acetyltransferase (CAT), horseradish peroxidase (HRP) or a fluorescent protein green, e.g., green fluorescent protein (GFP), or a derivative thereof.

In certain embodiments, particularly those in which the host cell is a microbial host cell, such as microalgae and diatoms, the coding sequence of the second expression cassette may encode a fusion protein. In some of these embodiments, the fusion protein may provide for secretion of the protein from the host cell in which it is expressed and, as such, may contain a signal sequence operably linked to the N-terminus of the protein, where the signal sequence contains a sequence of amino acids that directs the protein to the secretory system of the host cell, resulting in secretion of the protein from the host cell into the medium in which the host cell is growing. The signal sequence is cleaved from the fusion protein prior to secretion of the protein. The signal sequence employed may be endogenous or non-endogenous to the host cell and, in certain embodiments, may be signal sequence of a protein that is known to be highly secreted from a host cell. Therefore, in certain embodiments, a recombinant nucleic acid construct according to the present invention may comprise a signal sequence-encoding nucleic acid operably linked to a protein-encoding nucleic acid, where translation of the nucleic acid in a host cell produces a fusion protein comprising a protein having an N-terminal signal sequence for secretion of the protein from the host cell.

As discussed above, in certain embodiments, the polynucleotide may be codon-optimized for expression of the protein in a particular host cell or in a particular cellular organelle. Since codon usage tables listing the usage of each codon in many cells are known in the art (see, e.g., Nakamura et al, *Nucl. Acids Res.* 28: 292, 2000) or readily derivable, such nucleic acids can be readily designed giving the amino acid sequence of a protein to be expressed in a particular host cell or in a particular cellular organelle.

In some particularly preferred embodiments of the present application, compositions and methods disclosed herein can be used to introduce any genes or other nucleotide sequences that are of interest into a microorganism of the genus *Nannochloropsis*. Such nucleotide sequences include, but are not limited to, nucleic acids encoding proteins (e.g., enzymes) involved in the synthesis of fatty acids (e.g., polyunsaturated fatty acids (PUFA) such as docosahexaenoic acid (DHA), docosapentaenoic acid (DPA), eicosapentaenoic acid (EPA) and arachadonic acid (ARA). Such proteins include, but are not limited to, fatty acid synthases, fatty acid desaturases, and fatty acid elongases, as well as proteins associated with a PUFA-polyketide synthase complex and/or proteins associated with incorporation of such fatty acids into phospholipids or into triacylglycerol molecules. These pathways and corresponding genes and enzymes are well known in the art (for review, see, e.g., Ward and Singh, Process Biochemistry, 40:3672-3652, 2005). For example, the invention can be used to introduce genes encoding various omega-3 fatty acid desaturases into *Nannochloropsis* in an attempt to increase the level of docosahexaenoic acid (DHA) in the cells via omega-3 desaturation of docosapentaenoic acid (DPA).

Compositions and methods according to present disclosure are also useful for introducing into *Nannochloropsis* microorganisms genes and other nucleotide sequences encoding proteins associated with the isoprenoid biosynthetic pathway. Such proteins include, but are not limited to, HMG-CoA synthase and HMG-CoA reductase. Other suitable proteins include proteins associated with the synthesis of molecules derived from isoprenoid subunits including, but not limited to, various steroid compounds and various carotenoid compounds. Proteins associated with the synthesis of various carotenoid compounds include, but are not limited to, squalene synthase, phytoene synthase, phytoene desaturase, and various carotenoid cyclases, hydroxylases and ketolases.

Applicants of the present invention also contemplate introducing into Nannochloropsis one or more nucleic acid sequences encoding proteins associated with the synthesis of anti-oxidant compounds including, but not limited to, vitamin E and lipoic acid.

In addition, the compositions and methods disclosed herein can be used to introduce any genes or other nucleotide sequences vectors into Nannochloropsis microorganisms in order to inactivate or delete genes (i.e., "knock-out" or "targeted gene disruption"). The inactivation or deletion of genes of a microorganism is typically used for the purpose of enhancing the commercial value of the microorganism. For example, it may be desirable to remove genes that encode enzymes (or nucleic acids which regulate the expression of such genes) of the saturated and polyunsaturated fatty acid synthesis pathways. In another aspect, it may be desirable to inhibit or knock-out genes encoding proteins that are involved in the degradation of other valuable compounds produced by the Nannochloropsis microorganism or which otherwise lessen the value of the desired compound. For example, genes encoding lipases, fatty acid oxidation enzymes, and proteins that have objectionable flavors or odors may be desirable knock-out targets by the present invention. In yet another aspect, it may be desirable to knock-out genes encoding proteins that are associated with the synthesis of compounds whose synthesis is in competition with other molecules of interest. For example, such genes include, but are not limited to, genes encoding proteins involved in carbohydrate biosynthesis, genes encoding proteins involved in the synthesis of various products of isoprenoid pathways (e.g., sterols or specific carotenoid compounds), and genes encoding proteins involved in the synthesis of cell wall components. By way of example, gene sequences can be introduced into Nannochloropsis cells by the use of the methods and materials of this invention to inactivate genes that are homologous to the PUFA-polyketide synthase genes from Schizochytrium, Thraustochytrium, or Shewanella in order to assess their role in the production of polyunsaturated fatty acids (PUFA). As exemplified by Example 6, the present invention can also be used to inactivate, delete, or mutate native genes that are involved in the production of fatty acids, carotenoids, sterols, vitamins, or other compounds in order to improve the economics or acceptability of products that are related to these compounds. It is noted that in some embodiments, as discussed above, it may be desirable to enhance production of a given protein, whereas in other embodiments, it may be desirable to inhibit production of the same protein. Such determinations are based on the given use and production goals for a specific microorganism. The present invention is also useful for the process of genetic recombination in Nannochloropsis.

The skilled artisan in the art will further appreciate that AHAS-encoding sequences according the present disclosure can be used in engineering an i/v⁻ auxotrophic cells (i.e., cells that are deficient in the biosynthesis of branched-chain amino acids, i.e., isoleucine, leucine, valine, or combinations thereof), by deleting or disrupting the activity of the endogenous AHAS gene. The wild-type AHAS sequences can be used as a selectable marker in conjunction with the resulting ilv⁻ auxotrophic cells, using prototrophy as selection.

Other genes and nucleic acid molecules useful for introduction into Nannochloropsis microorganisms according to the methods disclosed herein will be apparent to those of skill in the art, and all such genes and molecules are intended to be encompassed by the present invention.

Making Recombinant Microorganisms

To use the isolated nucleic acid molecules sequences disclosed herein, recombinant DNA constructs suitable for transformation of host cells, e.g., algae cells and plant cells can be prepared. As described in detail below, techniques for transforming a wide variety of algae and higher plant species are well known and described in the technical and scientific literature.

Suitable host cells to be modified using the materials and methods according to the present invention include, but are not limited to, bacteria, protist, microalga, phytoplankton, fungus, protozoa. Host cells can be either untransformed cells or cells that are already transfected with at least one nucleic acid molecule.

In principle, the methods and compositions according to the present invention can be deployed for genetic engineering of any microbial species, including, but not limited to, microalgae and microfungi. The methods and compositions are preferably used with microorganisms that are important or interesting for aquaculture, agriculture, for the production of biomass used in production of liquid fuel molecules and other chemicals. Suitable species may include members of the genera *Amphora, Anabaena, Ankistrodesmus, Aplanochytrium, Arthrospira, Botryococcus, Chaetoceros, Chlamydomonas, Chlorella, Chlorococcum, Chrococcidiopsis, Chrysophyceae, Colwellia, Cricosphaera, Crypthecodinium, Cryptococcus, Cunninghamella, Cyclotella, Dunaliella, Elina, Gleocapsa, Isochrysis, Japanochytrium, Labrinthula, Labyrinthomyxa, Labyrinthula, Leptolyngbya, Lyngbya, Microcoleus, Monodus, Monoraphidium, Moritella, Mortierella, Mucor, Nannochloris, Nannochloropsis, Navicula, Neochloris, Nitzschia, Ochromonas, Oocystis, Oscillatoria, Ostreococcus, Parietochloris, Pavlova, Phaeodactylum, Photobacterium, Pichia, Pithium, Pleurochrysis, Pleurococcus, Porphyridium, Pseudoalteromonas, Pseudoanabaena, Psychromonas, Pyramimonas, Rhodosporidium, Scenedesmus, Schizochytrium, Shewanella, Skeletonema, Spirulina, Stichococcus, Synechococcus, Synechocystis, Tetraselmis, Thalassiosira, Thermosynechococcus, Thraustochytrium, Ulkenia,* and *Vibrio.*

Non-limiting examples of preferred species include, for instance, *Mortierella schmuckeri, Shewanella olleyana, Aplanochytrium kerguelensis, Crypthecodinium cohnii, Cryptococcus curvatus, Cunninghamella, Cunninghamella echinulata, Cunninghamella elegans, Dunaliella salina, Dunaliella viridis, Dunaliella tertiolecta, Haematococcus pluvialis, Elina marisalba, Elina sinorifica, Isochrysis galbana, Japanochytrium, Japanochytrium marinum, Labyrinthomyxa pohlia, Labyrinthomyxa sauvageaui, Labyrinthula algeriensis, Labyrinthula chattonii, Labyrinthula cienkowskii, Labyrinthula coenocystis, Labyrinthula macrocystis, Labyrinthula macrocystis atlantica, Labyrinthula macrocystis macrocystis, Labyrinthula magnifica, Labyrinthula minuta, Labyrinthula pacifica, Labyrinthula roscoffensis, Labyrinthula valkanovii, Labyrinthula vitellina, Labyrinthula zopfii, Labyrinthuloides minuta, Labyrinthuloides schizochytrops, Monodus subterraneus, Monoraphidium, Moritella marina, Mortierella alpina,*

*Mortierella isabellina, Mortierella ramannia, Mucor circinelloides, Mucor mecdo, Nannochloropsis gaditana, Nannochloropsis granulate, Nannochloropsis limnetica, Nannochloropsis oceanic, Nannochloropsis oculata, Nannochloropsis salina, Nitzschia alba, Nitzschia laeva, Nitzschia laevis, Pavlova lutheri, Pavlova pinguis, Parietochloris incise, Phaeodactylum cruentum, Phaeodactylum tricomutum, Photobacterium profundum, Pithium insidiosum, Pichia pastoris, Rhodosporidium toruloides, Schizochytrium aggregatum, Schizochytrium limacinum, Schizochytrium mangrovei, Schizochytrium minutum, Schizochytrium octosporum, Scenesdemus dimorphus, Scenesdemusur obliquus, Shewanella japonica, Isochrysis galbana, Tetraselmis suecica, Thraustochytrium aggregatum, Thraustochytrium arudimentale, Thraustochytrium aureum, Thraustochytrium benthicola, Thraustochytrium globo sum, Thraustochytrium kinnei, Thraustochytrium motivum, Thraustochytrium pachydermum, Thraustochytrium proliferum, Thraustochytrium roseum, Thraustochytrium striatum, Ulkenia amoeboida, Ulkenia minuta, Ulkenia profunda, Ulkenia radiata, Ulkenia radiate, Ulkenia sarkariana, Ulkenia sp. BP-5601, Ulkenia visurgensis,* and *Vibrio marinus.*

In some embodiments of the present application, preferred microorganisms to genetically modify include, but are not limited to, photosynthetic organisms such as cyanobacteria, algae, diatoms, and the like. Exemplary diatoms may include members of the genera *Achnanthes, Amphora, Chaetoceros, Coscinodiscus, Cylindrotheca, Cyclotella, Cymbella, Hantzschia, Navicula, Nitzschia, Pavlova, Pseudo-Nitzschia, Phaeodactylum, Psammodictyon, Skeletonema, Thalassionema,* and *Thallasiosira.* Preferred host cells for use in the present invention include microorganisms from a genus including, but not limited to: *Dunaliella, Labyrinthuloides, Japonochytrium, Scenedesmus, Schizochytrium,* and *Thraustochytrium.* Particularly preferred organisms in some embodiments include, but are not limited to, members of the genus *Nannochloropsis.* Preferred species within the genus *Nannochloropsis* include, but are not limited to, *N. gaditana, N. granulata, N. limnetica, N. oceanica, N. oculata,* and *N. salina.* Particularly preferred strains of this genus include, but are not limited to: *Nannochloropsis gaditana* CCMP1894, *Nannochloropsis oculata* CCMP525, and *Nannochloropsis salina* CCMP537. Other examples of suitable host microorganisms for genetic modification include, but are not limited to, yeast including *Saccharomyces cerevisiae, Saccharomyces carlsbergensis,* or other yeast such as *Candida, Kluyveromyces, Yarrowia,* or other fungi, for example, filamentous fungi such as *Aspergillus, Neurospora, Penicillium,* etc. Bacterial cells also may be used as hosts. This includes *Escherichia coli,* which can be particularly useful in fermentation processes. Alternatively, a host such as a *Lactobacillus* species, *Pseudomonas* species, or *Bacillus* species can be used as a host.

A number of methods and techniques useful for genetic transformation of microorganisms are well known in the art, and can be deployed for the methods of the present invention. Such genetic transformation can result in stable insertion and/or expression of transgenes from either the nucleus or the plastid, and in some cases can result in transient expression of transgenes. For example, genetic transformation of microalgae has been reported successful for more than 30 different strains of microalgae, which belong to at least ~22 species of green, red, and brown algae, diatoms, euglenids, and dinoflagellates (see, e.g. Radakovits et al., *Eukaryotic Cell,* 2010; Gong et al., *J. Ind. Microbiol. Biotechnol.,* 2011). Therefore, one skilled in the art will further appreciate that a variety of transformation methods can be used to introduce the nucleic acid molecules of the present invention into microalgal cells, including agitation of cells in the presence of glass beads or silicon carbide whiskers as reported by, for example, Dunahay, *Biotechniques,* 15(3):452-460, 1993; Kindle, *Proc. Natl. Acad. Sci. U.S.A.,* 1990; Michael and Miller, *Plant J.,* 13, 427-435, 1998. Electroporation techniques have been successfully used for genetic transformation of several microalgal species including *Nannochloropsis* sp. (see, e.g., Chen et al., *J. Phycol.,* 44:768-76, 2008), *Chlorella* sp. (see, e.g., Chen et al., *Curr. Genet.,* 39:365-370, 2001; Chow and Tung, *Plant Cell Rep. Vol.* 18, No. 9, 778-780, 1999), *Chlamydomonas* (Shimogawara et al., *Genetics,* 148: 1821-1828, 1998), *Dunaliella* (Sun et al., *Mol. Biotechnol.,* 30(3): 185-192, 2005). Microprojectile bombardment, also referred to as microparticle bombardment, gene gun transformation, or biolistic bombardment, has been used successfully for several algal species including, for example, *Phaeodactylum* (Apt et al., *Mol. Gen. Genet.,* 252:572-579, 1996), diatoms species *Cyclotella* and *Navicula* (Dunahay et al., *J. Phycol.,* 31:1004-1012, 1995), diatom *Cylindrotheca* (Fischer et al., *J. Phycol.,* 35:113-120, 1999), diatom species *Chaetoceros* sp. (Miyagawa-Yamaguchi et al., *Phycol. Res.* 59: 113-119, 2011), *Chlorella* (El-Sheekh, *Biologia Plantarum,* Vol. 42, No. 2:209-216, 1999), *Volvox* species (Jakobiak et al., *Protist,* 155:381-93, 2004). Additionally, *Agrobacterium*-mediated gene transfer techniques can also be useful for genetic transformation of microalgae, as has been reported by, for example, Kumar, *Plant Sci.,* 166(3):731-738, 2004, and Cheney et al., *J. Phycol.,* Vol. 37, Suppl. 11, 2001).

It will also be apparent to the skilled artisan that a number of well-known methods and techniques for transformation of chloroplasts of algal species and plant species may be used for the methods disclosed herein. See, for example, Svab et al., *Proc. Natl. Acad. Sci. USA* 87: 8526-8530, 1990; Svab and Maliga *Proc. Natl. Acad. Sci. USA* 90: 913-917, 1993; Svab and Maliga, *EMBO J.* 12: 601-606, 1993. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (*Proc. Natl. Acad. Sci. USA* 91: 7301-7305, 1994). As will be further appreciated by the skilled artisan, a variety of methods and techniques that have been used successfully for chloroplast transformation of several species of the marine red microalga Porphyridium (Lapidot et al., *Plant Physiol.* 129:7-12, 2002), chloroplast transformation of the algal species Dunaliella and Scenedesmus (see, for example, PCT Appl. No. WO2011034863), as well as chloroplast transformation of the green alga *Chlamydomonas reinhardtii* (Science, Vol. 240, 4858:1534-1538, 1988) can be deployed for the methods disclosed herein.

The polynucleotides of interest to be targeted to the chloroplast may be codon-optimized for expression in the chloroplast to account for differences in codon usage between the nucleus and this organelle. In this manner, the polynucleotide of interest may be synthesized using chloroplast-preferred codons. Such methodologies are well known in the art. See, for example, U.S. Pat. No. 5,380,831; PCT Appl. No. WO2011034863.

A transformation vector comprising a polynucleotide molecule of the present invention will typically comprise a marker gene that confers a selectable or scorable phenotype on target host cells, e.g., algal cells or plant cells. A number of selectable markers have been successfully developed for efficient isolation of genetic transformants of algae. Common selectable markers include antibiotic resistance, fluorescent markers, and biochemical markers. Several different antibiotic resistance genes have been used successfully for microalgal transformant selection, including bleomycin (see, for example, Apt et al., 1996, supra; Fischer et al., 1999, supra; Fuhrmann et al., *Plant J.,* 19, 353-61, 1999, Lumbreras et al., *Plant J.,* 14(4):441-447, 1998; Zaslayskaia et al., *J. Phycol.,* 36:379-386, 2000), spectinomycin (Cerutti et al., *Genetics,* 145: 97-110, 1997; Doetsch et al., *Curr. Genet.,* 39, 49-60, 2001; Fargo, *Mol. Cell. Biol.,* 19:6980-90, 1999), streptomycin (Berthold et al., *Protist,* 153:401-412, 2002), paromomycin (Jakobiak et al., *Protist,* supra.; Sizova et al., *Gene,* 277:221-229, 2001), nourseothricin (Zaslayskaia et al., 2000, supra), G418 (Dunahay et al., 1995, supra; Poulsen and Kroger, *FEBS Lett.,* 272:3413-3423, 2005, Zaslayskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin resistance (Stevens, *Mol. Gen. Genet.* 251:23-30, 1996), and paramomycin and neomycin resistance (Sizova et al., 2001, supra). Other fluorescent or chromogenic markers that have been used include luciferase (Falciatore et al., *J. Mar. Biotechnol.,* 1: 239-251, 1999; Fuhrmann et al., *Plant Mol. Biol.,* 2004; Jarvis and Brown, *Curr. Genet.,* 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.,* 1:165-169, 1994), β-galactosidase (Gan et al., *J. Appl. Phycol.,* 15:345-349, 2003; Jiang et al., *Plant Cell Rep.,* 21:1211-1216, 2003; Qin et al., *High Technol. Lett.,* 13:87-89, 2003), and green fluorescent protein (GFP) (Cheney et al., 2001, supra; Ender et al., *Plant Cell,* 2002, Franklin et al., *Plant J.,* 2002; 56, 148, 210).

One skilled in the art would readily appreciate that a variety of known promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which is the typical heterologous promoter used in dinoflagellates and chlorophyta (Chow et al, *Plant Cell Rep.,* 18:778-780, 1999; Jarvis and Brown, *Curr. Genet.,* 317-321, 1991; Lohuis and Miller, *Plant J.,* 13:427-435, 1998). The SV40 promoter from simian virus has also reported to be active in several algae (Gan et al., *J. Appl. Phycol.,* 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.,* 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.,* 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., *Mar. Biotechnol.,* 1:239-251, 1999; Zaslayskaia et al., *J. Phycol.* 36:379-386, 2000). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272:3413-3423, 2005), thus gene expression can be switched off or on when microalgal cells are grown in the presence of ammonium/nitrate.

In some embodiments, a polypeptide of interest to be expressed in a host cells may be targeted to the chloroplast. In this manner, while the polypeptide of interest is not inserted into the chloroplast, the expression cassette will additionally contain a nucleic acid encoding a chloroplast transit peptide to direct the gene product of interest to the chloroplast. Such transit peptides, also known as chloroplast-targeting sequences, are known in the art and include for example those of the chloroplast small subunit of ribulose-1,5-bisphosphate carboxylase (Rubisco) (de Castro Silva Filho et al., *Plant Mol. Biol.* 30: 769-780, 1996; Schnell et al., *J. Biol. Chem.* 266: 3335-3342, 1991; van den Broeck et al., *Nature* 313:358-363, 1985); 5-(enolpyruvyl) shikimate-3-phosphate synthase (EPSPS) (Archer et al., *J. Bioenerg. Biomemb.* 22: 789-810, 1990); tryptophan synthase (Zhao et al., *J. Biol. Chem.* 270: 6081-6087, 1995); plastocyanin (Lawrence et al., *J. Biol. Chem.* 272: 20357-20363, 1997); chorismate synthase (Schmidt et al., *J. Biol. Chem.* 268(36): 27447-27457, 1993); and the light harvesting chlorophyll a/b binding protein (LHBP) (Lamppa et al., *J. Biol. Chem.* 263: 14996-14999, 1988; Kavanagh et al., *Mol Gen Genet.* 215:38-45, 1988). See also Von Heijne et al., *Plant Mol. Biol. Rep.* 9: 104-126, 1991; Clark et al., *J. Biol. Chem.* 264: 17544-17550, 1989; Della-Cioppa et al., *Plant Physiol.* 84: 965-968, 1987; Romer et al., *Biochem. Biophys. Res. Commun.* 196: 1414-1421, 1993; and Shah et al., *Science* 233: 478-481, 1986. In microalgae, a number of chloroplast targeting sequences have been identified and may be suitable for the methods of the present invention. More recent examples of such sequences include a chloroplast-targeting signal identified in the sulfate permease gene SulP of *Chlamydomonas reinhardtii* (Chen et al., *Planta,* 218:98-106, 2003).

In one aspect of the present invention, compositions and methods disclosed herein can be used to introduce any genes or other nucleotide sequences that are of interest into a microorganism of, for example, the order *Nannochloropsis*. Such nucleotide sequences include, but are not limited to, nucleic acids encoding proteins (e.g., enzymes) associated with the saturated fatty acid synthesis pathways, the polyunsaturated fatty acid synthesis pathways, the isoprenoid pathways, the activity of a polyketide synthase complex, and the incorporation of fatty acids into phospholipids or triacylglycerol molecules, the synthesis of cell wall components, and the production of pigments.

In one exemplified example, compositions and methods disclosed herein can be used to introduce genes or other nucleotide sequences that encode proteins (e.g., enzymes) associated with the synthesis of fatty acids e.g., the polyunsaturated fatty acids (PUFA) such as docosahexaenoic acid (DHA), docosapentaenoic acid (DPA), eicosapentaenoic acid (EPA) and arachadonic acid (ARA). Such proteins include, but are not limited to: fatty acid synthases, fatty acid desaturases, and fatty acid elongases, as well as proteins associated with a PUFA-polyketide synthase complex and/or proteins associated with incorporation of such fatty acids into phospholipids or into triacylglycerol molecules. By way of example, gene sequences can be introduced into *Nannochloropsis* cells by using the methods and materials of this invention include those homologous to the PUFA-polyketide synthase genes from *Schizochytrium, Thraustochytrium, Shewanella*, or *Vibrio*.

The present invention is also useful for introducing into a host organism, such as *Nannochloropsis, Schizochytrium, Scenedesmus, Dunaliella*, or plant, genes and other nucleotide sequences encoding proteins associated with the isoprenoid biosynthetic pathway. Such proteins include, but are not limited to, HMG-CoA synthase and HMG-CoA reductase. The enzyme in the isoprenoid biosynthesis pathway can be farnesyl pyrophosphate synthase, geranyl geranyl phosphate synthase, squalene synthase, thioesterase, or fatty acyl-CoA desaturase. The enzyme in the isoprenoid biosynthesis pathway can be in a mevalonate pathway. Other suitable proteins include proteins associated with the synthesis of molecules derived from isoprenoid subunits including, but not limited to, various steroid compounds and various carotenoid compounds. Proteins associated with the synthesis of various carotenoid compounds include, but are not limited to, squalene synthase, phytoene synthase, phytoene desaturase, and various carotenoid cyclases, hydroxylases and ketolases.

The present disclosure also contemplates host cells making polypeptides that contribute to the secretion of fatty acids, lipids or oils, by transforming host cells (e.g., algal cells) and/or organisms comprising host cells with nucleic acids encoding one or more different transporters. In some instances, the host cell will naturally produce the molecule of interest, e.g. fatty acid, lipid, triglyceride or oil. Transformation of the host cell with a polynucleotide encoding a transport protein will allow for secretion or increased secretion of the molecule of interest. Therefore, the molecule of interest produced by the modified cells may be collected from the cells and/or the surrounding environment (e.g., growth medium, bioreactor). In some embodiments, the collection of the fatty acids, lipids, triglycerides, oil, or molecule of interest is performed after the product is secreted from the cell via a transporter.

In some embodiments, some host cells may be transformed with multiple genes encoding one or more enzymes. For example, a single transformed cell may contain exogenous nucleic acids encoding enzymes that make up an entire synthesis pathway.

Moreover, the molecules of the present invention could be expressed in prokaryotic systems in conjunction with site-directed mutagenesis to study the mechanisms by which different groups of herbicides inhibit AHAS. Alternatively, the system could be used to characterize the sites and residues in AHAS proteins that are involved in feed-back regulation, catalysis, and herbicide binding.

Making Transgenic Plants

Another embodiment of the present invention relates to a genetically modified plant, wherein the plant has been genetically modified to recombinantly express an acetohydroxyacid synthase comprising at least one biologically active domain of acetohydroxyacid synthase.

One embodiment of the present invention provides for the improvement of plants by making them resistant to herbicidal compounds, particularly to specific AHAS-inhibiting compounds. The gene sequences encoding mutated AHAS polypeptides disclosed herein that are tolerant to such herbicides can be introduced into a plant host, whereby the gene will be expressed and impart herbicide-tolerance to the plant. The mutated AHAS genes from a crop species can be introduced into other crop species to develop novel herbicide-tolerant crop varieties. Also, mutations equivalent to those disclosed herein can be introduced at the corresponding nucleotide positions of AHAS genes to confer herbicide tolerance. These mutated AHAS genes can then be used as selection markers in plant transformation systems.

To use the sequences of the present invention or a combination of them or parts and/or mutants and/or fusions and/or variants of them, recombinant DNA constructs are prepared that comprise the polynucleotide sequences of the invention inserted into a vector and that are suitable for transformation of plant cells. The construct can be made using standard recombinant DNA techniques (see, e.g., Sambrook et al., 1989, supra) and can be introduced into the plant species of interest by, for example, *Agrobacterium*-mediated transformation, or by other means of transformation, for example, as disclosed below.

The vector backbone may be any of those typically used in the field of plant biology such as plasmids, viruses, artificial chromosomes, BACs, YACs, PACs and vectors such as, for instance, bacteria-yeast shuttle vectors, lambda phage vectors, T-DNA fusion vectors and plasmid vectors (see, for example, Shizuya et al., *Proc. Natl. Acad. Sci. USA*, 1992; Hamilton et al. *Proc. Natl. Acad. Sci. USA*, 1996; Burke et al., *Science*, 1987; Sternberg et al., *Proc Natl Acad Sci USA*, 1990; Bradshaw et al., *Nucl Acids Res*, 1995; Frischauf et al., *J. Mol Biol*, 1983; and Walden et al., *Mol Cell Biol*, 1990).

Typically, the recombinant construct comprises a vector containing a nucleic acid molecule of the present invention with any desired transcriptional and/or translational regulatory sequences such as, for example, promoters, UTRs, and 3' end termination sequences. Vectors may also include, for example, origins of replication, scaffold attachment regions (SARs), markers, homologous sequences, and introns. The vector may also comprise a marker gene that confers a selectable phenotype on plant cells. The marker may preferably encode a biocide resistance trait, particularly antibiotic resistance, such as resistance to, for example, kanamycin, bleomycin, or hygromycin, or herbicide resistance, such as resistance to, for example, glyphosate, chlorsulfuron or phosphinothricin.

It will be understood that more than one regulatory region may be present in a recombinant polynucleotide, e.g., introns, enhancers, upstream activation regions, transcription terminators, and inducible elements. Thus, more than one regulatory region can be operably linked to said sequence. To "operably link" a promoter sequence to a sequence for the purpose of plant transformation, the translation initiation site of the translational reading frame of said sequence is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-acting regulatory element from the upstream region of the octopine synthase (ocs) gene (−212 to −154; Fromm et al., *Plant Cell*, 1, 977-984, 1989).

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to said sequence.

Some suitable promoters initiate transcription only, or predominantly, in certain cell types. For example, a promoter that is active predominantly in a reproductive tissue or callus cells can be used. In some preferred embodiments of the present invention, broadly expressing promoters may be used. A promoter can be said to be "broadly expressing" when it promotes transcription in many, but not necessarily all, plant tissues. Non-limiting examples of broadly expressing promoters that can be included in the nucleic acid constructs provided herein include cauliflower mosaic virus (CaMV) 35S promoters, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some other preferred embodiments, inducible promoters are particularly suitable for the methods disclosed herein. Inducible promoters confer transcription in response to external stimuli such as chemical agents or environmental stimuli. For example, inducible promoters can confer transcription in response to hormones such as giberellic acid or ethylene, or in response to light or drought. An example of a promoter induced by salt is rd29A (Kasuga et al, *Nature Biotech*, 17:(3)287-291, 1999).

A large database of plant promoters that are considered suitable for transgenesis may be found on the World Wide Web at wwwmgs.bionet.nsc.ru/mgs/dbases/tgp/home.html. In addition, methods for identifying and characterizing promoter regions in plant genomic DNA include, for example, those described in the following references: Jordano et al., *Plant Cell*, 1:855-866; 1989; Bustos, et al., *Plant Cell*, 1:839-854, 1989; Green et al., *EMBO J.* 7, 4035-4044, 1988; Meier et al., *Plant Cell*, 3, 309-316, 1991; and Zhang et al., *Plant Physiol.* 110: 1069-1079, 1996.

Plant transformation: Nucleic acid molecules of the present invention may be introduced into the genome or the cell of the appropriate host plant by a variety of techniques. These techniques, able to transform a wide variety of higher plant species, are well known and described extensively in the technical and scientific literature. For example, a variety of techniques known in the art are available for the introduction of DNA into a plant host cell. These techniques include transformation of plant cells by injection, microinjection, electroporation of DNA, PEG-mediated transformation, use of biolistics, fusion of cells or protoplasts, and via T-DNA using *Agrobacterium tumefaciens* or *Agrobacterium rhizogenes* or other bacterial hosts, for example.

In addition, a number of non-stable transformation methods that are well known to those skilled in the art may be desirable for the present invention. Such methods include, but are not limited to, transient expression and viral transfection.

Seeds are obtained from the transformed plants and used for testing stability and inheritance. Generally, two or more generations are cultivated to ensure that the phenotypic feature is stably maintained and transmitted.

A person of ordinary skill in the art will recognize that after the expression cassette is stably incorporated in transgenic plants and confirmed to be operable, it can be further introduced into other plants by sexual crossing. Any of a number of standard breeding techniques can be used, depending upon the species to be crossed.

It is also to be understood that two different transgenic plants can also be mated to produce offspring that contain two independently segregating added exogenous genes. Selfing of appropriate progeny can produce plants that are homozygous for both added exogenous genes. Back-crossing to a parental plant and out-crossing with a non-transgenic plant are also contemplated, as is vegetative propagation. As used herein, "vegetative propagation" refers to asexual propagation of the plant that is accomplished by taking and propagating cuttings, by grafting or budding, by layering, by division of plants, or by separation of specialized structures such as stem, roots, tubers, rhizomes, or bulbs.

Evaluation of Plant Transformation

Following introduction of heterologous foreign DNA into plant cells, the transformation or integration of heterologous gene in the plant genome can be confirmed by a number of methods such as analysis of nucleic acids, proteins and metabolites associated with the integrated gene.

For example, PCR analysis is a rapid method, among others, to screen transformed cells, tissue or shoots for the presence of incorporated gene at the earlier stage before transplanting into the soil (Sambrook and Russell, 2001, supra). PCR can be carried out using oligonucleotide primers specific to the herbicide-tolerance gene of interest or *Agrobacterium* vector background, etc.

A plant transformant derived from transformation experiments may be confirmed by Southern blot analysis of genomic DNA (Sambrook and Russell, 2001, supra). In general, total DNA is extracted from the transformant, digested with appropriate restriction enzymes, size-fractionated in an agarose gel and transferred to a nitrocellulose or nylon membrane. The membrane or "blot" is then probed with, for example, radiolabeled $^{32}$P target DNA fragment to confirm the integration of introduced gene into the plant genome according to standard techniques (Sambrook and Russell, 2001, supra). Alternatively, a nonradioactive DIG-labeled probe may be used for Southern blot analysis ("Genius" DIG-based system (Boehringer Mannheim Biochemicals GmbH, Germany).

In Northern blot analysis, RNA is isolated from specific tissues of transformant, fractionated in a formaldehyde agarose gel, and blotted onto a nylon filter according to standard procedures that are routinely used in the art (e.g., Sambrook and Russell, 2001, supra). Expression of RNA encoded by the transgene is then tested by hybridizing the filter to a radioactive $^{32}$P labeled probe or a nonradioactive DIG-labeled probe derived from an AHAS gene, by methods well known in the art (e.g., Sambrook and Russell, 2001, supra).

Western blot, biochemical assays and the like may be carried out on the transgenic plants to confirm the presence of protein encoded by the AHAS gene by standard procedures (e.g., Sambrook and Russell, 2001, supra) using antibodies that bind to one or more epitopes present on the herbicide-tolerant protein.

As discussed above, a number of markers have been developed for use with plant cells, such as resistance to chloramphenicol, the aminoglycoside G418, hygromycin, or the like. Other genes that encode a product involved in chloroplast metabolism may also be used as selectable markers. Additionally, the AHAS gene sequences disclosed herein are also useful as selectable markers to assess transformation of bacterial cells or plant cells. As discussed above, methods for detecting the presence of a transgene in a plant, plant organ (e.g., leaves, stems, roots, etc.), seed, plant cell, propagule, embryo or progeny of the same are well known in the art. In some embodiments, the presence of the transgene may be detected by testing for herbicide tolerance activity.

Fertile plants expressing a sequence according the present invention may be tested for herbicide-tolerance activity, and the plants showing optimal activity may be selected for further breeding. A wide variety of methods are available in the art to assay for herbicide-tolerance activity. Generally, the expressed protein is isolated from transgenic cells and/or transgenic plants, and used in an AHAS enzymatic assay. See, for example, U.S. Pat. No. 5,633,437, and Singh et al. (1988, supra). Alternatively, the transformed seedlings can be sprayed with an herbicidal compound that is known to target AHAS as described in, for example, U.S. Pat. No. 5,633,437.

In principle, the methods and compositions according to the present invention can be deployed for any plant species, including, but not limited to, monocots and dicots. The process is preferably used with plants that are important or interesting for agriculture, horticulture, for the production of biomass used in producing liquid fuel molecules and other chemicals, and/or forestry. Particularly preferred are higher plants, pertaining to the classes of Angiospermae and Gymnospermae. Plants of the subclasses of the Dicotylodenae and the Monocotyledonae are particularly suitable. Dicotyledonous plants belong to the orders of the Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Illiciales, Juglandales, Lamiales, Laurales, Lecythidales, Leitneriales, Magniolales, Malvales, Myricales, Myrtales, Nymphaeales, Papeverales, Piperales, Plantaginales, Plumbaginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Theales, Trochodendrales, Umbellales, Urticales, and Violales. Monocotyledonous plants belong to the orders of the Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, and Zingiberales. Plants belonging to the class of the Gymnospermae are Cycadales, Ginkgoales, Gnetales, and Pinales.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

The methods and compositions of the present invention are preferably used in plants that are important or interesting for agriculture, horticulture, biomass for the production of biofuel molecules and other chemicals, and/or forestry. Non-limiting examples include, for instance, *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Arundo donax* (giant reed), *Secale cereale* (rye), *Salix* spp. (willow), *Eucalyptus* spp. (eucalyptus), *Triticosecale* spp. (triticum—wheat X rye), Bamboo, *Carthamus tinctorius* (safflower), *Jatropha curcas* (Jatropha), *Ricinus communis* (castor), *Elaeis guineensis* (oil palm), *Phoenix dactylifera* (date palm), *Archontophoenix cunninghamiana* (king palm), *Syagrus romanzoffiana* (queen palm), *Linum usitatissimum* (flax), *Brassica juncea, Manihot esculenta* (cassava), *Lycopersicon esculentum* (tomato), *Lactuca saliva* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale, Taxus baccata, Taxus brevifolia, Artemisia annua, Cannabis saliva, Camptotheca acuminate, Catharanthus roseus, Vinca rosea, Cinchona officinalis, Coichicum autumnale, Veratrum califormica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis,* Chrysanthemum parthenium, Coleus forskohlii, Tanacetum parthenium, *Parthenium argentatum* (guayule), *Hevea* spp. (rubber), *Mentha spicata* (mint), *Mentha piperita* (mint), *Bixa orellana, Alstroemeria* spp., *Rosa* spp. (rose), *Dianthus caryophyllus* (carnation), *Petunia* spp. (petunia), *Poinsettia pulcherrima* (poinsettia), *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass), *Phleum pratense* (timothy), and conifers. Of interest are plants grown for energy production, so called energy crops, such as cellulose-based energy crops like *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (eucalyptus), *Triticosecale* spp. (triticum-wheat X rye), and Bamboo; and starch-based energy crops like *Zea mays* (corn) and *Manihot esculenta*

(cassaya); and sucrose-based energy crops like *Saccharum* sp. (sugarcane) and *Beta vulgaris* (sugarbeet); and biofuel-producing energy crops like *Glycine max* (soybean), *Brassica napus* (canola), *Helianthus annuus* (sunflower), *Carthamus tinctorius* (safflower), *Jatropha curcas* (Jatropha), *Ricinus communis* (castor), *Elaeis guineensis* (African oil palm), *Elaeis oleifera* (American oil palm), *Cocos nucifera* (coconut), *Camelina sativa* (wild flax), *Pongamia pinnata* (Pongam), *Olea europaea* (olive), *Linum usitatissimum* (flax), *Crambe abyssinica* (Abyssinian-kale), and *Brassica juncea*.

Throughout this disclosure, various information sources are referred to and incorporated by reference. The information sources include, for example, scientific journal articles, patent documents, textbooks, and World Wide Web browser-inactive page addresses. The reference to such information sources is solely for the purpose of providing an indication of the general state of the art at the time of filing. While the contents and teachings of each and every one of the information sources can be relied on and used by one of skill in the art to make and use embodiments of the invention, any discussion and comment in a specific information source should in no way be considered as an admission that such comment was widely accepted as the general opinion in the field.

The discussion of the general methods given herein is intended for illustrative purposes only. Other alternative methods and embodiments will be apparent to those of skill in the art upon review of this disclosure, and are to be included within the spirit and purview of this application.

It should also be understood that the following examples are offered to illustrate, but not limit, the invention.

EXAMPLES

Example 1

Identification and Isolation of an Acetohydroxyacid Synthase from *Nannochloropsis gaditana*

The applicants of the present application identified and isolated a nucleic acid molecule encoding a novel acetohydroxyacid synthase from chloroplast DNA content of the microalga *Nannochloropsis gaditana* CCMP1894 strain. The algal strain was obtained from the Provasoli-Guillard National Center for Marine Algae and Microbiota (NCMA, Maine, U.S.A.), which is formerly the National Center for Culture of Marine Phytoplankton (CCMP). The coding sequence of this novel gene, named SGI-Ng110602, together with its 503-bp upstream regulatory sequence, is provided in the Sequence Listing as SEQ ID NO: 2.

A homology search for the nucleotide sequence of the SGI-Ng110602 gene was conducted using the DDBJ/GenBank/EMBL database. Sequence identity and similarity were also determined using GenomeQuest™ software (Gene-IT, Worcester Mass. USA). In a BLASTX homology analysis, the nucleotide sequence of the SGI-Ng110602 gene was determined to encode acetohydroxyacid synthase; e.g. the deduced amino acid sequence of the SGI-Ng110602 gene was found to be 66%-67% identical with AHAS genes previously identified for several marine microorganisms. In fact, the deduced polypeptide of SGI-Ng110602 has the greatest sequence identity with an acetohydroxyacid synthase large subunit encoded by the chloroplast genomic content of the marine alga *Aureococcus anophageferens* strain CCMP1984, having GeneBank accession number ACS36845 (67.24% sequence identity over a 580/592 polypeptide alignment) (Ong et al., *J. Phycol.* 46:602-615, 2010). In addition, the SGI-Ng110602 polypeptide displayed 66.72% sequence identity with another chloroplast-encoded AHAS gene previously identified for the marine microalga *Aureoumbra lagunensis* strain CCMP1507, having GeneBank accession number ACS36933 (66.95% sequence identity over the entire 592-amino acid polypeptide) (Ong et al., *J. Phycol.* 46:602-615, 2010).

Further sequence analysis revealed that the amino acid sequence of the SGI-Ng110602 gene contains several conserved domains and motifs that have been previously reported to be important for an AHAS enzymatic activity as well as for the physiological functions of an anabolic AHAS. For example, each of the seven conserved motifs, which are characteristic of AHAS enzymes previously reported by Bedbrood et al. (U.S. Pat. No. 5,605,011), were also found present in the amino acid sequence of SGI-Ng110602 polypeptide (see, e.g., the sequence alignment of FIG. 1 and Sequence Listing). In addition, an amino acid motif, RFDDR, which has been previously reported to be conserved in the β-domain of several anabolic AHASs, was also identified in the sequence of SGI-Ng110602 polypeptide from *N. gaditana*. This conserved motif is widely believed to be a determinant of the FAD-dependent characteristic of anabolic AHASs (see, e.g. Le and Choi, 2005, supra; Dugglebby and Pang, 2000, supra).

Taken together, these results indicate that the SGI-Ng110602 encodes an acetohydroxyacid synthase from *Nannochloropsis gaditana*.

Example 2

Construction of Modified *N. gaditana* AHAS Genes

In order to create novel mutant alleles of the *N. gaditana* AHAS gene with reduced sensitivity to AHAS inhibitors that can be used as selectable markers for subsequent transformation experiments, the applicants of the present application introduced several point mutations in the coding sequence of the *N. gaditana* AHAS gene.

*Nannochloropsis gaditana* AHAS K173T Mutant.

Applicants engineered a K173T mutation in the *N. gaditana* AHAS polypeptide by altering its coding sequence using the technique of "splicing by overlap extension by the polymerase chain reaction" (SOE-PCR) as described in Ho et al. (*Gene* 77, 1:51-9, 1989), with minor modifications. The first set of PCRs generated two fragments—a 5' half product and a 3' half product—using total *N. gaditana* genomic DNA as template. The 5' fragment was generated using primers oSGI-JU-78 (5'-CGGTACCCGGGGATCCa-gagtggctcccaacatatc-3'; SEQ ID NO:17) and oSGI-JU-75 (5'-cttctaaccctacatcagttggaatatcaattaaaac-3'; SEQ ID NO: 14); and the 3' fragment was generated using primers oSGI-JU-76 (5'-gatattccaactgatgtagggttagaagaaatagttc-3'; SEQ ID NO: 15) and oSGI-JU-79 (5'-CGACTCTAGAG-GATCacaccactttcaagaggagc-3'; SEQ ID NO:18). Each of the two primers oSGI-JU-78 and oSGI-JU-79 had a 15 base extension that added sequence adjacent to the BamHI site of pUC19 to allow for IN-FUSION® (CLONETECH LABORATORIES, INC., MOUNTAIN VIEW, CA) (Clonetech Laboratories, Inc., Mountain View, Calif.) cloning into pUC19 vector. Primers oSGI-JU-75 and oSGI-JU-76 were designed to overlap each other to allow for SOE-PCR and to introduce nucleotide changes that result in the K173T mutation. The resulting PCR products were fused together in a final PCR reaction utilizing primers oSGI-JU-78 and oSGI- JU-79. This final PCR product was cloned into a BamHI pre-digested pUC19 vector. The resulting plasmid was named pSGI-JU-32. The sequence of the entire K173T-mutated AHAS gene in the resulting plasmid, named pSGI-JU-32, was verified by sequencing and the presence of the K173T-encoding mutation was thereby confirmed.

*Nannochloropsis gaditana* AHAS G114S Mutant

The G114S mutation was generated in the *N. gaditana* AHAS polypeptide by altering its coding sequence using a '2-fragment IN-FUSION® (Clonetech Laboratories, Inc., Mountain View, Calif.)' cloning procedure (Clontech Laboratories, Inc., Mountain View, Calif.). The first fragment contained the nucleotide sequence upstream of the G114 codon of the *N. gaditana* AHAS gene and was amplified from *N. gaditana* genomic DNA using primers oSGI-JU-78 (5% CGGTACCCGGGGATCCagagtggctcccaacatatc-3'; SEQ ID NO: 17) and oSGI-JU-108 (5% tacctgaccagtaat-taaaatcattg-3'; SEQ ID NO: 23). The second fragment contained the nucleotide sequence of the *N. gaditana* AHAS gene starting 15-bp upstream of the G114 codon, the G114S mutation and the remaining 3' half of the gene. This fragment was amplified from *N. gaditana* genomic DNA using primers oSGI-JU-109 (5'-attactggtcaggtatcgagagca attggaacagatgc-3'; SEQ ID NO: 24) and oSGI-JU-79 (5'-GACTCTAGAGGATCacaccactttcaagaggagc-3'; SEQ ID NO: 18). The nucleotide sequence of the primer oSGI-JU-109 introduced the G114S mutation, and also contained 15 bases immediately preceding the codon G114, which were needed for the IN-FUSION® (Clontech Laboratories, Inc., Mountain View, Calif.) cloning system to ligate the two fragments together. Each of the primers oSGI-JU-78 and oSGI-JU-79 had a 15 base extension that added sequence adjacent to the BamHI site of pUC19 to allow for IN-FUSION® (Clontech Laboratories, Inc., Mountain View, Calif.) cloning into pUC19. The sequence of the entire G114S-mutated AHAS gene in the resulting clone, named pSGI-JU-40, was verified by sequencing and the presence of the G114S-encoding mutation was thereby confirmed.

*Nannochloropsis gaditana* AHAS W494S Mutant

The W494S mutation was introduced in the *N. gaditana* AHAS polypeptide by altering its coding sequence using the 2-fragment IN-FUSION® (Clontech Laboratories, Inc., Mountain View, Calif.) cloning procedure as described above. The first fragment contained the nucleotide sequence upstream of the W494 codon of the *N. gaditana* AHAS gene and was amplified from *N. gaditana* genomic DNA using primers oSGI-JU-78 (5'-CGGTACCCGGGGATCCagagtggctcccaacatatc-3'; SEQ ID NO: 17) and oSGI-JU-110 (5'-ttgtcgtaccataccttgccaac-3'; SEQ ID NO: 25). The second fragment contained the nucleotide sequence of the *N. gaditana* AHAS gene starting 15-bp upstream of the W494 codon, the W494S mutation and the remaining 3' half of the gene. This fragment was amplified from *N. gaditana* genomic DNA using primers oSGI-JU-111 (5'-ggtatggtacgacaactgcaacagtctttttatgatgaaag-3'; SEQ ID NO: 26) and oSGI-JU-79 (5'-CGACTCTAGAGGATCacaccacittcaagaggagc-3'; SEQ ID NO: 18). The nucleotide sequence of the primer oSGI-JU-111 introduced the W494S mutation, and also contained 15 bases immediately preceding the codon W494, which were needed for the IN-FUSION® (Clontech Laboratories, Inc., Mountain View, Calif.) cloning system to ligate the two fragments together. Primers oSGI-JU-78 and oSGI-JU-79 each had a 15-base extension that added sequence adjacent to the BamHI site of pUC19 to allow for IN-FUSION® (Clontech Laboratories, Inc., Mountain View, Calif.) cloning into pUC19. The entire W494S-mutated AHAS gene in the resulting plasmid, name pSGI-JU-41, was verified by sequencing and the presence of the W4945-encoding mutation was thereby confirmed.

*Nannochloropsis gaditana* AHAS W494L Mutant The W494L mutation was introduced in the *N. gaditana* AHAS polypeptide by altering its coding sequence using the '2-fragment IN-FUSION® (Clontech Laboratories, Inc., Mountain View, Calif.) cloning procedure as described above. The first fragment contained the nucleotide sequence upstream of the W494 codon of the *N. gaditana* AHAS gene and was amplified from *N. gaditana* genomic DNA using primers oSGI-JU-78 (5'-CGGTACCCGGGGATCCagagtgctccaacatatc-3'; SEQ ID NO: 17) and oSGI-JU-110 (5'-ttgtcgtaccataccttgccaac-3'; SEQ ID NO: 25). The second fragment contained the nucleotide sequence of the *N. gaditana* AHAS gene starting 15 bp upstream of the W494 codon, the W494L mutation and the remaining 3' half of the gene. This fragment was amplified from *N. gaditana* genomic DNA using primers oSGI-JU-112 (5'-ggtatggtacgacaatcgcaacagtcttttatgatgaaag-3'; SEQ ID NO: 26) and oSGI-JU-79 (CGACTCTAGAGGATCacaccactttcaagaggagc; SEQ ID NO: 18). The primer oSGI-JU-112 introduced the W494L mutation, and also contained 15 bases immediately preceding the codon W494, which were needed for the IN-FUSION® (Clontech Laboratories, Inc., Mountain View, Calif.) cloning system to ligate the two fragments together. Each of the two primers oSGI-JU-78 and oSGI-JU-79 had a 15 base extension that added sequence adjacent to the BamHI site of pUC19 to allow for IN-FUSION® (Clontech Laboratories, Inc., Mountain View, Calif.) cloning into pUC19. The sequence of the entire W494L-mutated AHAS gene in the resulting clone, named pSGI-JU-42, was verified by sequencing and the presence of the W494L-encoding mutation was confirmed.

*Nannochloropsis gaditana* AHAS D297N Mutant

The D297N mutation was introduced in the *N. gaditana* AHAS polypeptide by altering its coding sequence using the '2-fragment IN-FUSION® (Clontech Laboratories, Inc., Mountain View, Calif.) cloning procedure as described above. The first fragment contained the nucleotide sequence upstream of the D297 codon of the *N. gaditana* AHAS gene and was amplified from *N. gaditana* genomic DNA using primers o SGI-JU-78 (CGGTACCCGGGGATCCagagtgctcccaacatatc; SEQ ID NO: 17) and oSGI-JU-150 (atcaaatcttgcacctattgcta; SEQ ID NO: 31). The second fragment contained the nucleotide sequence of the *N. gaditana* AHAS gene starting 15 bp upstream of the D297 codon, the D297N mutation and the remaining 3' half of the gene. This fragment was amplified from *N. gaditana* genomic DNA using primers oSGI-JU-151 (ggtgcaagatttgatAaCcgggttactggtaaacttgaag; SEQ ID NO: 32) and oSGI-JU-79 (CGACTCTAGAGGATCacaccactttcaagaggagc; SEQ ID NO: 18). The primer oSGI-JU-151 introduced the D297N mutation, an MspI restriction site, and contained 15 bases immediately preceding the codon D297 of the gene, which were needed for the IN-FUSION® (Clontech Laboratories, Inc., Mountain View, Calif.) cloning system to ligate the two fragments together. Each of the primers oSGI-JU-78 and oSGI-JU-79 had a 15 base extension that added sequence adjacent to the BamHI site of pUC19 to allow for IN-FUSION® (Clontech Laboratories, Inc., Mountain View, Calif.) cloning into pUC19. The sequence of the entire D297 N-mutated AHAS gene in the resulting clone, named pSGI-X-48, was verified by sequencing and the presence of the D297N-encoding mutation was confirmed.

Example 3

Isolation of AHAS Genes from Herbicide-Resistant Nannochloropsis Cells

The present applicants observed that the growth of Nannochloropsis sp. is strongly inhibited by the herbicidal compound metsulfuron methyl (MSM, Sigma-Aldrich, CAS #74223-64-6). This compound has been previously reported to be a potent inhibitor of AHAS activity in several organisms. The applicants performed additional testing to determine that 30 µM of MSM could be used to effectively suppress wild-type growth.

Applicants subsequently identified eighteen (18) mutant isolates of the Nannochloropsis gaditana CCMP1894 strain that showed high levels of resistance to the herbicidal compound MSM. In fact, cells of each of the 18 isolates grew efficiently in growth media containing the herbicide MSM at concentrations where wild-type growth was found to be significantly impaired. The sequences of the endogenous AHAS gene from each of these MSM-resistant isolates were PCR-amplified and sequenced to determine the mutations responsible for the resistance. For this purpose, the AHAS gene sequence from each isolate was amplified as two overlapping fragments by a colony-PCR procedure. Amplification of the 5' fragments was performed by using two primers oSGI-JU-85 (5'-AAACAAGCAATTCT-TAACTAAACG-3'; SEQ ID NO: 22) and oSGI-JU-77 (5'-GCGTCATATAAAGGAGTTACTG-3'; SEQ ID NO: 16); and the PCR products were subsequently end-sequenced with the primers oSGI-JU-85 and oSGI-JU-80 (5'-AAATG-GTCGTCCTGGTCCAG-3'; SEQ ID NO: 19), respectively. Similarly, amplification of the 3' fragments was performed by using the primers oSGI-JU-81 (5'-CGCCTCTCAAGCA-CAAATTC-3'; SEQ ID NO: 20) and oSGI-JU-84 (5'-ACACCACTTTCAAGAGGAGCTG-3'; SEQ ID NO: 21); and the PCR products were subsequently isolated, sequenced, and compared to the nucleotide sequence of the wild-type N. gaditana AHAS gene described in Example 1 and set forth in the Sequence Listing as SED ID NO: 2).

Sequence comparison analyses of the AHAS genes isolated from all 18 MSM-resistant cell lines of Nannochloropsis gaditana revealed that the amino acid sequence of each of the MSM-resistant AHAS proteins had one of the following substitutions: A122V, A36S, A36T, and D297n. The sequence analysis result is summarized in Table 2. Nine of the eighteen MSM-resistant AHAS proteins had a mutation at the position Ala36 in their polypeptide sequences. Of those nine, five contained an A36T substitution and four contained an A36S substitution. Eight of the resistant proteins had a mutation at the position Asp297 to asparagine (D297N). One resistant protein had a mutation at Ala122 to valine (A122V). It was noted that the residues A36, A122, and D297 of N. gaditana AHAS were found located within the conserved motifs A, C, and E of Arabidopsis thaliana AHASL as reported previously by, for example, Bedbrook et al. (U.S. Pat. No. 5,605,011). In fact, amino acid residues in the AHAS polypeptides from several other organisms that correspond to the residues A36, A122, and D297 of N. gaditana AHAS had been previously shown to be highly conserved. Substitutions or alterations at these positions had also been shown previously to confer resistance to several herbicidal compounds (for review, see, e.g., Powles and Yu, Annual Rev Plant Biol 61:317-347, 2010; Duggleby and Pang, 2000, supra; U.S. Pat. No. 5,605,011; US Pat. Appl. No. US20100287641). The finding that all of the eighteen AHAS genes isolated from MSM-resistant Nannochloropsis cells had a mutation at positions previously reported to result in resistance to AHAS inhibitors further supported that this gene indeed encoded an AHAS large subunit from Nannochloropsis.

At the nucleotide level, when compared to the DNA sequence of the wild-type N. gaditana AHAS coding sequence (SEQ ID NO: 2), each of the MSM-resistant AHAS coding sequences was found to contain one of the following nucleotide substitutions: C365T (this nucleotide change corresponds to the A122V amino acid substitution described above), G106A (this nucleotide change corresponds to the A36T amino acid substitution described above), G106T (this nucleotide change corresponds to the A36S amino acid substitution), or G889A (this nucleotide change corresponds to the D297N amino acid substitution described above). A summary of the altered codons found in the AHAS sequences of the MSM-resistant Nannochloropsis cells is provided in Table 2.

As discussed above, because of the degeneracy of the genetic code, other mutations in the AHAS coding sequence can also encode the A122V, A36S, A36T, and D297N amino acid substitutions.

TABLE 2

Point mutations identified in the AHAS gene of MSM-resistant Nannochloropsis gaditana cells.

| Strain ID | Nucleotide change | Codon change* | Amino acid change |
|---|---|---|---|
| D1 | G889A | GAT->AAT | D297N |
| D2 | G106A | GCA->ACA | A36T |
| D3 | G106A | GCA->ACA | A36T |
| D4 | G106A | GCA->ACA | A36T |
| D5 | G889A | GAT->AAT | D297N |
| D6 | G106A | GCA->ACA | A36T |
| D7 | G106A | GCA->ACA | A36T |
| D8 | C365T | GCT->GTT | A122V |
| E1 | G889A | GAT->AAT | D297N |
| E2 | G889A | GAT->AAT | D297N |
| E3 | G106T | GCA->TCA | A36S |
| E4 | G106T | GCA->TCA | A36S |
| F1 | G889A | GAT->AAT | D297N |
| F2 | G106T | GCA->TCA | A36S |
| F3 | G889A | GAT->AAT | D297N |
| F4 | G889A | GAT->AAT | D297N |
| F5 | G106T | GCA->TCA | A36S |
| F6 | G889A | GAT->AAT | D297N |

Example 4

Identification and Isolation of Genes Encoding AHAS Large Subunits from Nannochloropsis occulata and Nannochloropsis salina This Example discloses experimental details of the identification and isolation of AHAS genes encoding AHAS large subunits from two different Nannochloropsis species, n. occulata and N. salina, as well as their respective promoter regions, by using a PCR-based strategy. The PCR primers used in this experiment were designed based on the nucleotide sequences corresponding to conserved domains and motifs identified in the N. gaditana AHAS coding sequence, as disclosed in Example 1.

The amplification of each of the AHAS genes of n. occulata and N. salina was performed using total genomic DNA that was prepared from cells of either n. occulata (CCPM525) or N. salina (CCMP537), both of which were obtained from the National Center for Culture of Marine Phytoplankton (CCMP, Maine, U.S.A.)

Isolation, Subcloning, and Sequence Analysis of an AHAS Gene from *Nannochloropsis salina*

Genomic DNA was prepared from cells of *N. salina* CCMP537 strain. The *N. salina* AHAS gene was amplified from *N. salina* genomic DNA using the two following primers: oSGI-JU-78 (5'-CGGTACCCGGGGATCCagagtg-gctcccaacatatc-3'; SEQ ID NO: 17) and oSGI-JU-79 (5'-gatattccaactgatgtagggttagaagaaatagttc-3'; SEQ ID NO: 18). Each of the primers oSGI-JU-78 and oSGI-JU-79 had a 15 base extension that added sequence adjacent to the BamHI site of pUC19 to allow for IN-FUSION® (Clontech Laboratories, Inc., Mountain View, Calif.) cloning into pUC 19. The AHAS gene from *N. salina* was cloned into pUC 19 to generate pSGI-JU-43. The nucleotide sequences of the entire insert from five independent clones was sequenced and a consensus sequence was obtained and a clone that matched the consensus sequence was labeled pSGI-JU-43. The entire coding sequence of this novel gene, named SGI-Ns 110809, together with its 503-bp upstream regulatory sequence, is disclosed in the Sequence Listing as SEQ ID NO: 4. The nucleotide sequences for *N. gaditana* AHAS and *N. salina* AHAS were found to be very similar, which helps explain why the primers oSGI-JU-78 and oSGI-JU-79, which were designed using *N. gaditana* sequence, could amplify the *N. salina* AHAS. In fact, the sequence homologies between the two genes were ~98% identical at the nucleotide level and ~99% identical at the amino acid level. In addition, each of the seven conserved motifs characteristic of AHAS enzymes previously reported by Bedbrood et al. (U.S. Pat. No. 5,605,011), as well as the RFDDR (SEQ ID NO:34) motif, previously reported to be conserved in anabolic AHASs (see, e.g. Le and Choi, 2005, supra; Dugglebby and Pang, 2000, supra), were also identified in the sequence of the SGI Ns110809 protein (SEQ ID NO: 3). See, the sequence alignment of FIG. 1.

Isolation, Subcloning, and Sequence Analysis of an AHAS Gene from *N. oculata*

Genomic DNA was prepared from cells of *N. salina* CCPM525 strain. Initially, the sequence of a short fragment of the *N. oculata* AHAS gene was obtained by using PCR techniques and degenerate primers. The forward primer used was either oSGI-JU-113 (5'-ATHGGNACNGAYGCNTTC-CAAGA-3'; SEQ 1N NO: 28) or oSGI-JU-115 (5'-ATHG-GNACNGAYGCNTTTCAAGA-3'; SEQ ID NO: 29). The reverse primer used was oSGI-JU-117 (5'-GTNCCRTG-CATNCCTAGCAT-3'; SEQ ID NO: 30). The resulting PCR products were cloned into linearized pCR®-Blunt vector (Invitrogen, Carlsbad, Calif.) and the sequence of the insert was determined. Based on thus obtained sequence, a "GenomeWalker™" kit (Clontech Laboratories, Inc. Palo Alto, Calif.) was subsequently deployed to obtain the entire coding sequence as well as 238-bp of upstream regulatory sequence. The coding sequence of this novel gene, named SGI-No110817, together with its 238-bp upstream regulatory sequence, is disclosed in the Sequence Listing as SEQ ID NO: 6. Applicants found that the nucleotide sequence for *N. oculata* AHAS was highly similar to those for *N. gaditana* AHAS and *N. salina* AHAS described above, i.e., 87% and 86% sequence identity, respectively, at the nucleotide level over the entire lengths. At the amino acid level, the sequence of SGI-No110817 (SEQ ID NO: 5) and each of the two *N. gaditana* AHAS and *N. salina* AHAS polypeptides were approximately-92% identical. The sequence of the 238-bp immediately preceding the *N. oculata* AHAS gene start codon is also disclosed in the Sequence Listing as SEQ ID NO: 13.

Example 5

Construction of Recombinant Expression Vectors Suitable for Heterologous Gene Expression in *Nannochloropsis*

Vector construction: Each expression cassette typically includes an AHAS-coding sequence which is operably linked to regulatory elements suitable for expression in a target host cell. The regulatory elements typically include a promoter sequence and a terminator sequence. For expression in algal cell and plant cell, preferred promoters include viral CaMV 35S promoters from cauliflower mosaic virus (Chow et al, *Plant Cell Rep.*, 18:778-780, 1999; Jarvis and Brown, *Curr. Genet.*, 317-321, 1991; Lohuis and Miller, *Plant J.*, 13:427-435) and SV40 promoters from simian virus (Gan et al., *J. Appl. Phycol.*, 151 345-349, 2003; Qin et al., *Hydrobiologia* 398-399, 469-472, 1999). Terminator sequence is typically a terminator sequence from SV40. Techniques for making such promoter-gene-terminator constructs and subsequent sequence confirmation are well known in the art. The following examples are offered by way of illustrations and not by way of limitation.

a) Recombinant Vectors for Expression of Heterologous Genes in the Plastid

These plastid vectors are designed and constructed to enable the introduction of heterologous sequences of interest to be expressed in the plastid. A plastid-targeting vector typically contains two expression cassettes. The first expression cassette includes an AHAS coding sequence carrying a mutation that confers resistance to an AHAS inhibitor. The AHAS coding sequence is typically placed under control of its own promoter. In some instances, the AHAS sequence upstream of the mutation is also altered such that alternative codons are used while encoding for the same protein. Such altered sequences are generated by the Reverse Translate software, which is a codon-optimization software that can be found on the World Wide Web at bioinformatics.org/sms2/rev_trans.html. In some other instances, codon optimization is done manually by altering the third degenerate bases of codons according to the degeneracy of the genetic code. A second expression cassette typically contains a heterologous promoter sequence derived from the psbA or psbD genes of Scenesdemus dimorphus (PCT Appl. No. WO2011034863), which is operably linked with the heterologous gene sequence and a homologous terminator sequence derived from an AHAS gene of *Nannochloropsis*. Prior to algal transformation, each of these plastid-targeting vectors is restriction digested to release the above described expression cassettes from the vector backbone (i.e. pUC19). *Nannochloropsis* cells are transformed with linearized DNA. The homologous AHAS sequence upstream of the engineered mutation and the homologous AHAS terminator sequence help target the integration to the AHAS locus of the plastid genome.

b) Recombinant Vectors for Expression of Heterologous Genes in the Nucleus (i.e., Ectopic Integration)

These vectors are designed and constructed to enable the introduction of heterologous sequences of interest to be expressed from the nuclear genome. For a nucleus-integrated *Nannochloropsis* AHAS sequence to be functional, the 5' end of the gene is typically modified to include a translational start codon and a nucleotide sequence encoding a chloroplast transit peptide (CTP) to create a CTP-AHAS chimeric sequence. A nucleus-targeting vector typically contains two expression cassettes. In a first expression cassette, a CTP-AHAS chimeric sequence is operably linked to a viral promoter region and terminator sequence, both derived from simian virus (SV40), which have been previously reported to be functional in *Nannochloropsis* cells. Introduced adjacent to the first expression cassette is a second expression cassette that contains a second heterologous coding sequence operably linked to a second promoter and terminator sequence active in *Nannochloropsis* (i.e. 35S from cauliflower mosaic virus). The resulting CTP-AHAS chimeric gene and/or the heterologous gene are sometimes codon-optimized to reflect the codon bias of the *Nannochloropsis* genome. The expression cassettes are released from the vector backbone (i.e. pUC19) by restriction digestion and purified prior to being transformed into *Nannochloropsis* cells.

c) Nuclear Vectors for Expression of a Heterologous Gene Via Homologous Recombination (i.e., Targeted Integration)

These recombinant vectors are used for introduction of a heterologous nucleic acid sequence to be expressed from a specific location on the nuclear genome of a host cell. The nuclear vectors of Example 5(b) above are modified such that both the promoter:CTP-AHAS:terminator cassette and the promoter:heterologous gene:terminator cassette are flanked by sequences having homology to a target locus on the *Nannochloropsis* genome which allow for homologous recombination of the expression cassette into the *Nannochloropsis* genome. The expression cassettes are released from the vector backbone (i.e. pUC19) by restriction digestion and purified prior to being transformed into *Nannochloropsis* cells.

In some experiments, the transformation systems of the present invention are used to introduce foreign genes into *Nannochloropsis* cells via co-transformation, as described in more detail in Example 6 of the present disclosure. In these experiments, the foreign genes are placed under control of various viral promoters and *Nannochloropsis* promoters, and an appropriate terminator (e.g., SV40 terminator region). In one particular experiment, the present applicants have produced and introduced into *Nannochloropsis* cells a synthetic gene that encodes a green fluorescence protein from, for example, jellyfish *Aequorea macrodactyla* (Xia et al., *Mar. Biotechnol.*, 4 (2):155-62, 2002). Expression cassettes containing foreign genes are sometimes introduced into *Nannochloropsis* cells by direct inclusion within the transformation vector containing a modified-AHAS gene as a selectable marker.

Example 6

Genetic Transformation of a *Nannochloropsis* Species with the Recombinant AHASs This example demonstrates the transformation of an algal strain with a gene encoding an AHAS polypeptide that is modified to a mutant form which is capable of conferring resistance to an AHAS inhibitor.

Nuclear Transformation:

Recombinant nucleic acid molecules used in this experiment are vector constructs each including a mutated AHAS-encoding nucleotide sequence as described in Examples 2 and 5 in which the AHAS sequence is operably linked to a promoter and terminator sequence active in *Nannochloropsis*. In this experiment, the vector construct is not designed for integration into the chloroplast genome but is rather for ectopic insertion into the nuclear genome. For a nucleus-integrated *Nannochloropsis* AHAS sequence to be functional in the chloroplast, the 5' end of the gene is typically modified to include a translational start codon and a nucleotide sequence encoding a chloroplast transit peptide (CTP) to create a CTP-AHAS chimeric sequence. The transit peptide helps direct the AHAS protein to the chloroplast. For this purpose, a nucleotide sequence encoding a chloroplast transit peptide (CT') derived from chlorophyll a/b protein (Lamppa et al., 1988, supra; Kavanagh et al, 1988, supra) and an translational start codon is inserted immediately upstream of the coding sequence of the AHAS gene. The resulting CTP-AHAS chimeric gene is also codon-optimized to reflect the codon bias of the *Nannochloropsis* nuclear genome. The CTP-AHAS chimeric gene and regulatory sequences are flanked by nucleic acid sequences having homology to a target locus on the *Nannochloropsis* genome for homologous recombination of the gene into the *Nannochloropsis* nuclear genome. All DNA manipulations are carried out essentially as described by Sambrook et al. (1989, supra) and Cohen et al. (1998, supra).

Transformations are carried out with algal cells of the *Nannochloropsis gaditana* strain CM1894. Cells are grown to log phase ($1-5 \times 10^7$ cells/mL) at 25° C. in L1-Si+10× N&P medium i.e., L1 media (Guillard and Hargraves, *Phycologia* 32:234-236, 1993) without silica and with 10× concentration of nitrate and phosphate, 1% $CO_2$, 100 µE light on a 16:8 light dark cycle with a an orbital shaker set at 110 rpm. Cells are harvested by centrifugation at 2,500×g at 25° C. for 10 min. The supernatant is decanted and cells are washed three times with 50 mL of 385 mM Sorbitol then resuspended at $1 \times 10^{10}$ cells/mL in 385 mM Sorbitol. One hundred microliter of this cell suspension is mixed with linearized DNA (in a maximum volume of 10 µL) and transferred to a pre-chilled electroporation cuvette (0.2 cm gap). Electroporation is performed with an electroporator that is typically set at 50 µF capacitance, 500 S2 resistance and voltage of 2.2 kV. After electroporation, 1 mL of 385 mM Sorbitol is added to the cuvette then the suspension is transferred to a 15 mL tube containing 10 mL L1-Si+10× N&P medium. Cells are recovered at room temperature under low light for 1-2 days. After recovery, cells are collected by centrifugation at 2,500×g at 25° C. for 10 min then resuspended in 500 µL L1-Si+10×N&P medium. 250 µL of cell suspension are plated onto each L1-Si+10×N&P plates containing herbicide at appropriate selective concentrations, which are typically 30 µM metsulfuron methyl (MSM, Sigma-Aldrich).

Chloroplast Transformation

For chloroplast transformation of algal cells, a particle bombardment procedure is deployed as described in Cohen et al. (*Method. Enzymol.* 297; 192-208, 1998) with minor modifications. In a typical chloroplast transformation experiment, *Nannochloropsis* cells are cultured at 30° C. in L1-Si+10×N&P medium, 1% $CO_2$, 100 µE light on a 16:8 light dark cycle with an orbital shaker set at 110 rpm. In most experiments, selection plates are L1-Si+10×N&P medium agar plates with herbicide resistance selection. When the herbicide MSM is used, the typical herbicide concentration is 30 µM. Each plate typically has approximately $1 \times 10^{8-9}$ algal cells. DNA coated particles are delivered to the cells using a Biolistic® PDS-1000/He particle delivery system (Bio-Rad, Hercules, Calif.). In some other experiments, algal cells are transformed after plating on L1-Si+10×N&P plates without selection then transferred to plates with selection after recovery of 2-3 days under low light conditions.

Example 7

Characterization of Recombinant *Nannochloropsis* Cells

In most *Nannochloropsis* transformation experiments where a fluorescence reporter gene is included in the transformation vector, fluorescence microscopy techniques are deployed for the rapid identification of transformed cells and subsequent characterization of the transgenic cells.

In addition, a colony PCR technique was deployed to identify and/or confirm cell lines that were successfully transformed. For colony PCR analysis, *Nannochloropsis* cells from a single colony or 0.5 µL of culture are typically used per 25 µL of PCR reaction.

To identify strains that contain the CTP-AHAS chimeric gene inserted into the nuclear genome, a primer pair is used in which one primer typically anneals to the CTP-encoding nucleotide sequence while the other primer anneals within the AHAS coding segment. Desired clones are those that yield a PCR product of the expected size for the CTP-AHAS recombinant gene.

To identify strains containing a mutated AHAS gene that is integrated into the chloroplast or nucleus, colony PCR analysis is typically performed with a primer pair that is designed such that the primers flank the mutation introduced. The PCR product then is purified and sequenced to confirm the presence of the mutation introduced. Whenever possible, primers can also be designed such that the desired mutation introduces or destroys a cut site of a restriction enzyme. In this case, digestion or lack of digestion of the PCR product with this restriction enzyme is used to confirm the introduction of the mutation.

To identify strains that contain heterologous nucleotide sequences inserted into the nucleus or chloroplast, a primer pair is used where both primers typically anneal within the heterologous nucleotide sequence. Desired clones are those that yield a PCR product of the expected size for the heterologous sequence.

To identify strains having deletions of an endogenous sequence in their genome, such as by homologous recombination, a primer pair is used where either one or both primers anneal within the sequence that would be displaced. Desired clones are those that do not yield a PCR product of the expected size for the endogenous sequence. Clones in which the endogenous locus gives weak-intensity PCR products relative to the control reaction are also subjected to further characterization.

Southern blot techniques are sometimes also deployed for the characterization of transformed *Nannochloropsis* cells, by using common protocols and procedures described in, e.g. Sambrook et al. (1989, supra). Southern hybridization blots are prepared using DNA isolated from parental *N. gaditana* strain CCMP 1894 cells and several putative algal transformants in order to confirm the presence of transformation vector DNA sequences within the transformed cells. Genomic DNA, including both chloroplast and nuclear contents, is isolated using a Meta-G-Nome DNA Isolation Kit (Epicentre Biotechnologies, Madison, Wis.), digested with various restriction enzymes, separated by electrophoresis through agarose gels (0.8%-1.2% w/v), and then transferred to nylon membranes by alkaline capillary transfer technique.

When a recombinant vector as described in Example 5 is used as starting DNA material, detection of vector DNA in transformed cells is typically carried out by use of a hybridization probe that contains a nucleotide sequence complementary to a heterologous nucleotide sequence included in the recombinant vector and hence introduced into the algal transformants. A DIG-labeled probe is generated via PCR with specific primers and a nucleotide mix that includes DIG-labeled 11-UTP, using the "Genius" DIG-based system (Boehringer Mannheim Biochemicals GmbH, Germany). Pre-hybridization of the membrane is typically carried out at 68° C. for 1 h in the hybridization buffer supplied in the Genius kit. Hybridization is typically carried out at 68° C. for 18 h in hybridization buffer containing a pre-denatured probe. The membranes are then washed twice for 5 min with 50 mL 2×SSC/0.1% SDS and twice for 15 min in 50 mL 0.1×SSC/0.1% SDS. Chemiluminescent detection of hybridizing DNA is performed as described in the Genius kit instructions. Since hybridization probe is designed to specifically anneal to a heterologous nucleotide sequence introduced into the algal transformants, genomic DNA from non-transformed *N. gaditana* strain CCMP1894 cells typically does not hybridize to such probe. Conversely, DNA derived from algal cell lines that are successfully transformed with recombinant vectors hybridizes to such probe and are thereby identified for further characterization.

Example 8

Transformation of Recombinant Vectors that Contain Additional Heterologous DNA Molecules This section describes exemplary transformation methods using a recombinant vector constructed as described in Example 5 to produce via co-transformation algal strains that contain additional foreign DNA molecules which are not linked to a selectable marker gene.

Co-transformation of an algal strain is achieved by simultaneous introduction of a recombinant vector containing a mutated AHAS-gene having a reduced sensitivity to an AHAS inhibitor, and an additional vector containing an additional foreign nucleic acid molecule to be expressed in the algal cell. The vectors are co-precipitated on the gold particles as described in Example 6, using approximately 2.5 µg of each vector DNA. After the bombardment of target cells with the plasmid-coated gold particles, recombinant strains are selected on herbicide-containing agar plates as described in Example 6. The presence of the second, non-selected recombinant vector inserted in the genome is then confirmed and further characterized by PCR analyses or by Southern blot hybridization. High co-transformation frequencies (ranging from, e.g., 5-90%) are typically achieved. This co-transformation method is typically used to introduce additional recombinant nucleic acid molecules that do not carry a selectable marker.

The transformation systems described above represent a significant advance in the ability to genetically engineer microorganisms, particularly microalgae including *Nannochloropsis*. The availability of two independent transformation systems, along with the high co-transformation efficiencies that occur, should allow stacking of multiple commercially relevant traits in engineered strains. Furthermore, the apparent presence of homologous recombination in this microalga should allow the development of gene knockout procedures in order to identify the functions of unknown genes and to eliminate undesirable traits in production strains.

Example 9

Functional In Vitro AHAS Bioassays

Expression and Purification of Recombinant AHAS:
Nucleic acid molecules encoding full-length AHAS polypeptides or predicted AHAS domains as disclosed in the present application are separately cloned into a suitable *E. coli* expression vector containing a selectable antibiotic resistant marker, such as ampicillin or kanamycin resistant genes. Individual plasmids are used to transform *E. coli* competent cells. For each construct, a single colony is inoculated in LB medium supplemented with an appropriate antibiotic and grows overnight at 37° C. The following day, fresh media are inoculated with 1% of overnight culture and grown at 37° C. to logarithmic phase, or until optical density of the culture at 600 nm reached 0.7-0.8. Sometimes, expression of recombinant AHAS polypeptides is induced by addition of 0.5 mM isopropyl-β-d-thiogalactopyranoside (IPTG) and additional incubation for overnight at 18° C. The recombinant *E. coli* cells expressing the recombinant AHAS polypeptides are harvested by centrifugation at 3000×g for 15 min at 4° C. Each cell pellet is suspended in an appropriate lysis buffer, for example buffer-A (20 mM sodium phosphate, pH 8.0, 0.5 M NaCl and 20 mM imidazole) containing 1% (v/v) Triton X-100 and a protease inhibitor cocktail, followed by sonication. Expression of the recombinant AHAS proteins is confirmed by Western dot blot analyses and/or SDS-PAGE analyses. AHAS proteins are then purified by a variety of common protein purification techniques, including sulfate ammonium precipitation and DEAE-Sepharose column fractionation (see, e.g., Sambrook and Russell, 2001, supra). The protein concentration for all samples is determined by Bradford assay following the instruction manual of the Bradford reagent (Bio-Rad, USA). Purified AHAS proteins are tested in in vitro AHAS bioassays as described below with appropriate controls.

Microplate Assay for AHAS Activity

The AHAS enzymatic activity is measured according to the method of Singh et al. (1988, supra) with some minor modifications. All chemicals are dissolved in dimethyl sulfoxide (DMSO) at a concentration of 2 mM. Four microliters of chemical solution (final concentration 40 µM) is added to individual wells of the 96-well microplate containing 156 µl of reaction buffer (final concentration of 100 mM potassium phosphate, pH 7.5, 1 mM ThDP, 10 mM $MgCl_2$, 50 µM FAD, and 0.5 µg of purified AHAS extract in a 200 µl reaction mixture), and the mixture is pre-incubated at 37° C. for 10 min. Reactions are initiated by adding 40 µl of 375 mM pyruvate (final 75 mM). After incubation at 37° C. for 1 h, the reaction is terminated by the addition of 30 µl of 4 M $H_2SO_4$. The reaction mixture was further incubated at 65° C. for 15 min to decarboxylate the reaction product, acetolactate. One hundred microliters of reaction product is mixed with 90 µl of 0.5% (w/v) creatine and 90 µl of 5% (w/v) α-naphtol solution in 2.5 M NaOH (freshly prepared), and is then incubated at 65° C. for 15 min. The absorbance of the red-colored complex is measured at 525 nm. One unit (U) of activity is defined as the amount of enzyme that is required for the production of 1 µmol of acetolactate per minute under the assay conditions described above.

Example 10

Transformation of Plant, Plant Cell, and Tissues

Vector construction: Each of the coding regions of the AHAS genes of the invention is connected independently with appropriate promoter and terminator sequences for expression in plants. Such sequences are well known in the art and may include a viral CaMV 35S promoter, a rice actin promoter or a maize ubiquitin promoter for expression in monocots, the *Arabidopsis* UBQ3 promoter or for expression in dicots, and the NOS or OCS terminators from *Agrobacterium*. Techniques for producing and confirming promoter-gene-terminator constructs also are well known in the art. The following examples are offered by way of illustrations and not by way of limitation.

Production of the Recombinant AHAS in Transformed Plants

Expression cassettes that include either full-length or truncated forms of the AHAS proteins as described above are made in suitable shuttle vectors by routine procedures, using a CaMV 35S promoter (Howell and Hull, Virology, 1978) and a ubiquitin promoter (Christensen et al., *Plant Mol. Biol.* 1992). Preferably, the codon usage of the open reading frame is adapted to that of the host plant so as to optimize expression efficiency. Plant cells, including e.g. barley, wheat, triticale, corn, cotton, and rice cells, are then transformed with the resulting recombinant vectors.

Barley, wheat, triticale, corn cells are stably transformed by either *Agrobacterium*-mediated transformation or by electroporation using wounded and enzyme-degraded embryogenic callus, as described in, e.g., Henzel et al. (*Inter. J. of Plant Genomics*, 2009); PCT Appl. No. WO 92/09696 and U.S. Pat. No. 5,641,664.

Cotton cells are stably transformed by *Agrobacterium*-mediated transformation as described by, e.g., Umbeck et al., 1987, and U.S. Pat. No. 5,004,863.

Rice cells are stably transformed by essentially following the method described by Hiei et al., *Plant J.* August; 6(2):271-82, 1994, and PCT Appl. No. WO 92/09696.

Regenerated transformed corn, cotton and rice plants are selected by Northern blot, Southern blot, ELISA, and herbicide-tolerance effect, or a combination of these techniques. Progeny plants containing heterologous AHAS polypeptides according to the present invention show improved tolerance to herbicides compared to untransformed control plants with appropriate segregation of herbicide tolerance and the transformed phenotype. Protein and RNA measurements show that increased herbicide tolerance is linked with higher expression of the heterologous AHAS protein in the plants.

*Agrobacterium*-Mediated Transformation of Maize Cell with the AHAS-Encoded Sequences of the Invention Maize embryos are isolated from the 8-12 DAP ears, and those embryos of 0.8-1.5 mm in size are used for transformation. Embryos are plated with the scutellum side up on a suitable incubation media, and optionally incubated overnight at 25° C. in the dark. Embryos are then contacted with an *Agrobacterium* strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in suitable selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

Transformation of Maize Cells with the AHAS-Encoded Sequences of the Invention by Using Aerosol Beam Technology.

Maize embryos are isolated from the 8-12 DAP ears, and those embryos of 0.8-1.5 mm in size are used for transformation. Embryos are plated scutellum side-up on a suitable incubation media, such as DN62A5S media (3.98 g/L N6 Salts; 1 mL/L of 1000× Stock N6 Vitamins; 800 mg/L L-Asparagine; 100 mg/L Myo-inositol; 1.4 g/L L-Proline; 100 mg/L Casaminoacids; 50 g/L sucrose; 1 mL/L of 1 mg/mL Stock 2,4-D), and incubated overnight at 25° C. in the dark. The resulting explants are transferred to mesh squares (30-40 per plate), then transferred onto osmotic media for 30-45 minutes, and subsequently transferred to a beaming plate (see, for example, PCT Appl. No. WO200138514 and U.S. Pat. No. 5,240,842).

Recombinant DNA constructs designed to express the sequences of the invention in plant cells are accelerated into plant tissue using an aerosol beam accelerator, using conditions essentially as described in PCT Appl. No. WO200138514. After beaming, embryos are incubated for 30 min on osmotic media, and then placed onto incubation media overnight at 25° C. in the dark. To avoid damaging beamed explants, they are incubated for at least 24 hours prior to transfer to recovery media. Embryos are then spread onto recovery period media, for 5 days, 25° C. in the dark, transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Example 11

Additional Assays for AHAS Activity and Herbicide-Tolerance Activity in Transgenic Plants The ability of a recombinant AHAS protein to confer herbicide tolerance to a plant cell, plant part, or whole plant is often assessed in a number of ways. One way well known in the art is to spray transgenic seedlings with a herbicidal compound that is known to target AHAS as described in, for example, U.S. Pat. No. 5,633,437. Typically, transgenic seeds are planted in an appropriate soil mix. Pots are placed on a heating mat and the soil temperature is increased from about 65° F. to about 90° F. At the 2-3 leaf stage, seedlings are treated with test herbicides using a linear track laboratory sprayer calibrated to deliver about 42.5 GPA. Plants are watered by sub-irrigation after herbicide application. Observations of percent control are typically made at around 21 days after herbicide application. The results are reported as percent (%) control where 100% injury is equal to complete control as determined by the absence of growth. All treatments are replicated four times in a randomized complete block design. In some cases, additional tests are performed at much higher herbicide application rates to determine the extent of resistance.

Alternatively, in vitro AHAS enzyme assays are sometimes performed on ground tissues of transgenic plants to determine if resistance in the transgenic plants is due to the modulated AHAS activity itself. See, e.g. U.S. Pat. No. 5,633,437 and U.S. Pat. Appl. No. 20110053777A1. Typically, such in vitro assays are performed as follows. Five grams of fresh green leaf tissue are ground to a powder in a mortar in the presence of liquid nitrogen. The powder is then extracted with 100 mL of buffer containing 50 mM N-[2-hydroxyethyl]piperazine-N'-[3-propanesulfonic acid], (EPPS); pH 7.2; 5 mM $MgCl_2$; 2 mM EDTA; 1 mM valine; 1 mM leucine; 10% glycerol; 10 mM pyruvate; 5 mM Dithiothreitol; 1% polyvinyl polypyrrolidone (PVPP) and 10 µM flavin adenine dinucleotide and filtered through cheesecloth. The filtrate is then centrifuged at 15,000×g for 15 min. The supernatant resulting from centrifugation of the crude extract is brought to 40% ammonium sulfate. The ammonium sulfate pellet is not frozen and is resuspended in standard buffer used for $I_{50}$ determinations and then gel-filtered through the same buffer. This preparation is used for determinations of $K_m$ for pyruvate and $I_{50}$. The $K_m$ is equal to the substrate concentration at which the initial reaction velocity is half maximal and also referred to as the Michaelis-Menten constant. The $K_m$ is determined using Lineweaver-Burke double-reciprocal plots. The $I_{50}$ values by various AHAS inhibitors are also determined on both sensitive enzymes and insensitive enzymes. $I_{50}$ is the concentration in which 50% inhibition is observed and is determined from linear regression analysis of the linear portion of the dose/response curve. Typically, the insensitive form of AHAS enzymes is unimpaired with respect to pyruvate, as compared to the corresponding wild-type AHAS.

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention as described and claimed herein.

All publications and patent applications mentioned in this specification are herein incorporated by reference to the same extent as if each individual publication or patent application was specifically can individually indicated to be incorporated by reference. Throughout this disclosure, various information sources are referred to and are, where specifically noted, incorporated by reference. The information sources include, for example, World Wide Web browser-inactive page addresses. The reference to such information sources is solely for the purpose of providing an indication of the general state of the art at the time of filing. While the contents and teachings of each and every one of the information sources can be relied on and used by one of skill in the art to make and use embodiments of the invention, any discussion and comment in a specific information source should in no way be considered as an admission that such comment was widely accepted as the general opinion in the field.

Headings within the application are solely for the convenience of the reader, and do not limit in any way the scope of the invention or its embodiments.

What is claimed is:

1. An isolated nucleic acid molecule comprising
a nucleic acid sequence encoding an acetohydroxyacid synthase (AHAS) exhibiting 90% or greater identity to an amino acid sequence selected from the group consisting of SEQ ID NO: 1, SEQ ID NO: 3, and SEQ ID NO: 5;
wherein the AHAS has at least one amino acid substitution at an amino acid position selected from the group consisting of R9, G35, A36, L38, I56, G114, A116, A122, I171, K173, I186, N194, A234, M272, D296, D297, P319, K337, S348, P352, F361, E364, V367, V491, W494, F498, D500, P567, and G568 of SEQ ID NO: 1, 3, or 5;
and further wherein said AHAS has reduced sensitivity to an AHAS inhibitor compared to the AHASs encoded by SEQ ID NO 1, 3 or 5.

2. An isolated polypeptide encoded by a nucleic acid molecule according to claim 1.

3. A nucleic acid molecule according to claim 1, wherein said at least one amino acid substitution is at an amino acid position selected from the group consisting of A36, G114, A122, D297, and W494, of SEQ ID NO: 1, 3, or 5.

4. A recombinant nucleic acid construct comprising a nucleic acid molecule according to claim 1 operably linked to a heterologous nucleic acid sequence.

5. The recombinant nucleic acid construct of claim 4, wherein said heterologous nucleic acid sequence is a heterologous promoter.

6. The recombinant nucleic acid construct of claim 4, wherein said heterologous nucleic acid sequence encodes a transit peptide.

7. A host cell comprising a nucleic acid molecule according to claim 1.

8. The host cell according to claim 7, wherein said nucleic acid molecule is integrated into the genome of said host cell via homologous recombination or ectopic insertion.

9. The host cell according to claim 7, wherein said nucleic acid molecule is integrated into a chloroplast genome or nuclear genome of said host cell.

10. The host cell according to claim 7, wherein said host cell is an algal cell, a bacterial cell, a fungal cell, or a plant cell.

11. The host cell according to claim 7, wherein said host cell is a *Nannochloropsis* cell.

12. The host cell according to claim 7, wherein said nucleic acid molecule further comprises a second heterologous nucleic acid sequence to be expressed by said host cell, said second heterologous nucleic acid sequence encoding a reporter protein.

13. A host organism comprising the host cell of claim 7.

14. A biological sample, biomass, or progeny derived from a host organism according to claim 13.

15. A method for modulating sensitivity of a cell to an AHAS inhibitor, said method comprising introducing into said cell a nucleic acid molecule according to claim 1, wherein said nucleic acid molecule confers reduced sensitivity of said cell to said AHAS inhibitor as compared to a control cell.

16. The method of claim 15, said method further comprising a step of selecting cells that have been successfully transformed with said nucleic acid molecule by culturing said cells in a growth medium containing at least one AHAS inhibitor that is inhibitory to the growth of untransformed cells.

17. The method of claim 15, said method further comprising a step of regenerating from said transformed cell a transformed organism.

18. The method of claim 15, wherein said nucleic acid molecule is integrated into the genome of said host cell via homologous recombination or ectopic insertion.

19. The method of claim 15, wherein said nucleic acid molecule is integrated into a chloroplast genome or nuclear genome of said host cell.

20. The method of claim 15, wherein said host cell is an algal cell, a bacterial cell, a fungal cell, or a plant cell.

21. The method of claim 15, wherein said host cell is a *Nannochloropsis* cell.

22. The method of claim 15, wherein said nucleic acid molecule further comprises a second heterologous nucleic acid sequence to be expressed by said host cell said second heterologous nucleic acid sequence encoding a reporter protein.

23. The nucleic acid molecule of claim 3, wherein the amino acid substitution is selected from the group consisting of: A36T, A36S, A122V, and D297N.

* * * * *